(12) United States Patent
Bhattacharya et al.

(10) Patent No.: US 7,585,869 B2
(45) Date of Patent: Sep. 8, 2009

(54) SUBSTITUTED HETEROCYLCES FOR THE TREATMENT OF ABNORMAL CELL GROWTH

(75) Inventors: Samit Kumar Bhattacharya, Groton, CT (US); Jinshan Chen, Clinton, CT (US); Richard Damian Connell, East Lyme, CT (US); John Charles Kath, Waterford, CT (US); Goss S. Kauffman, Ledyard, CT (US); Blaise S. Lippa, Mystic, CT (US); Joel Morris, East Lyme, CT (US)

(73) Assignee: Pfizer, Inc., New York, NY (US)

( * ) Notice: Subject to any disclaimer, the term of this patent is extended or adjusted under 35 U.S.C. 154(b) by 523 days.

(21) Appl. No.: 10/849,707

(22) Filed: May 20, 2004

(65) Prior Publication Data

US 2004/0242604 A1    Dec. 2, 2004

Related U.S. Application Data

(60) Provisional application No. 60/473,817, filed on May 27, 2003.

(51) Int. Cl.
*A61K 31/517*    (2006.01)
*C07D 239/94*    (2006.01)

(52) U.S. Cl. .................................. 514/266.22; 544/293
(58) Field of Classification Search ............. 514/266.2, 514/266.22, 266.23, 266.24; 544/284, 293
See application file for complete search history.

(56) References Cited

U.S. PATENT DOCUMENTS

| | | | | |
|---|---|---|---|---|
| 5,821,246 A | 10/1998 | Brown et al. | ................. | 514/253 |
| 6,284,764 B1 * | 9/2001 | Kath et al. | ............... | 514/266.2 |
| 6,465,449 B1 * | 10/2002 | Kath et al. | ................... | 514/183 |
| 6,541,481 B2 * | 4/2003 | Kath et al. | ............... | 514/260.1 |
| 6,867,201 B2 * | 3/2005 | Kath et al. | ................... | 514/183 |
| 6,903,217 B2 * | 6/2005 | Bacque et al. | .............. | 546/180 |

FOREIGN PATENT DOCUMENTS

| | | | |
|---|---|---|---|
| WO | 9609294 | | 3/1996 |
| WO | 9906378 | | 2/1999 |
| WO | 99-37635 | * | 7/1999 |
| WO | 0121594 | | 3/2001 |
| WO | 2004006846 | | 1/2004 |

* cited by examiner

*Primary Examiner*—James O Wilson
*Assistant Examiner*—Tamthom N Truong
(74) *Attorney, Agent, or Firm*—Scully, Scott, Murphy & Presser, P.C.

(57) ABSTRACT

The invention relates to compounds of formula 1

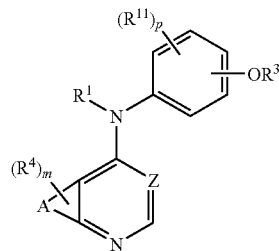

and to pharmaceutically acceptable salts, prodrugs and solvates thereof, wherein $R^1$, $R^3$, $R^4$, $R^{11}$, N, Z, A, m and p are as defined herein. The invention also relates to methods of treating abnormal cell growth in mammals by administering the compounds of formula 1 and to pharmaceutical compositions for treating such disorders which contain the compounds of formula 1. The invention also relates to methods of preparing the compounds of formula 1.

15 Claims, No Drawings

SUBSTITUTED HETEROCYLCES FOR THE TREATMENT OF ABNORMAL CELL GROWTH

BACKGROUND OF THE INVENTION

This invention relates to novel bicyclic derivatives that are useful in the treatment of abnormal cell growth, such as cancer, in mammals. This invention also relates to a method of using such compounds in the treatment of abnormal cell growth in mammals, especially humans, and to pharmaceutical compositions containing such compounds.

It is known that a cell may become cancerous by virtue of the transformation of a portion of its DNA into an oncogene (i.e., a gene which, on activation, leads to the formation of malignant tumor cells). Many oncogenes encode proteins that are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are enzymes which span the cell membrane and possess an extracellular binding domain for growth factors such as epidermal growth factor, a transmembrane domain, and an intracellular portion which functions as a kinase to phosphorylate specific tyrosine residues in proteins and hence to influence cell proliferation. Other receptor tyrosine kinases include c-erbB-2, c-met, tie-2, PDGFr, FGFr, and VEGFR. It is known that such kinases are frequently aberrantly expressed in common human cancers such as breast cancer, gastrointestinal cancer such as colon, rectal or stomach cancer, leukemia, and ovarian, bronchial or pancreatic cancer. It has also been shown that epidermal growth factor receptor (EGFR), which possesses tyrosine kinase activity, is mutated and/or overexpressed in many human cancers such as brain, lung, squamous cell, bladder, gastric, breast, head and neck, esophageal, gynecological and thyroid tumors.

Accordingly, it has been recognized that inhibitors of receptor tyrosine kinases are useful as selective inhibitors of the growth of mammalian cancer cells. For example, erbstatin, a tyrosine kinase inhibitor, selectively attenuates the growth in athymic nude mice of a transplanted human mammary carcinoma which expresses epidermal growth factor receptor tyrosine kinase (EGFR) but is without effect on the growth of another carcinoma which does not express the EGF receptor. Thus, the compounds of the present invention, which are selective inhibitors of certain receptor tyrosine kinases, are useful in the treatment of abnormal cell growth, in particular cancer, in mammals. In addition to receptor tyrosine kinases, the compounds of the present invention can also display inhibitory activity against a variety of other non-receptor tyrosine kinases (eg: lck, src, abl) or serine/threonine kinases (e.g.: cyclin dependent kinases).

Various other compounds, such as styrene derivatives, have also been shown to possess tyrosine kinase inhibitory properties. More recently, five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties. Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose. Other patent applications that refer to anti-cancer compounds are U.S. patent application Ser. Nos. 09/488,350 (filed Jan. 20, 2000) and 09/488,378 (filed Jan. 20, 2000), both of which are incorporated herein by reference in their entirety.

SUMMARY OF THE INVENTION

The present invention relates to compounds of Formula 1

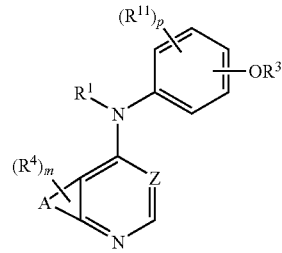

or a pharmaceutically acceptable salt, solvate or prodrug thereof, wherein:

Z is $CR^1$, C—CN, or N;

A represents a fused 5, 6 or 7-membered ring optionally containing 1 to 4 heteroatoms which may be the same or different and which are selected from —$N(R^1)$—, O, and $S(O)_j$, wherein j is an integer from 0 to 2, the fused ring containing a total of 1, 2 or 3 double bonds inclusive of the bond in the pyridine or pyrimidine ring to which it is fused wherein the $R^1$ group attached to the nitrogen is absent if a double bond includes the foregoing optional nitrogen moiety —$N(R^1)$—, with the proviso that the fused ring does not form part of a purine and that the fused ring does not contain two adjacent O or $S(O)_j$ atoms, and wherein the carbon atoms of the A moiety are optionally substituted with 0 to 3 $R^4$ groups;

each $R^1$ and $R^2$ is independently selected from H and $C_1$-$C_6$ alkyl;

m is an integer from 0 to 3;

p is an integer from 0 to 4;

$R^3$ is phenyl or a 4 to 6-membered heterocyclic, wherein said heterocyclic group is optionally fused to a benzene ring or a $C_5$-$C_8$ cycloalkyl group, and the foregoing $R^3$ groups, including any optional fused rings referred to above, are optionally substituted by 1 to 5 $R^9$ groups;

$R^4$ is —-$(CR^1R^2)_qX(CR^1R^2)_rR^5$ wherein q is an integer from 0 to 5, and r is an integer from 0 to 5, X can be absent or represents —$N(R^{14})$—, —NH—, O, CO, —$N(R^{14})CO$—, —$CON(R^{14})$—, —C(O)(cis or trans alkene)-, $NR^1C(O)$(cis or trans alkene)-, C(O)(alkyne)—, $NR^1C(O)$(alkyne)-, —$N(R^{14})C(O)N(R^{14})$—, —$N(R^{14})S(O)_j$—, —$S(O)_jN(R^{14})$—, $S(O)_j$, wherein j is an integer from 0 to 2;

$R^5$ is $R^{12}$, $C(O)NR^6R^7$, $C_3$-$C_8$ cycloalkyl, or 4 to 10 membered heterocyclic, wherein 1 or 2 ring carbon atoms of the heterocyclic group are optionally substituted with an oxo (=O) moiety and sulfur containing heterocyclic groups are optionally substituted with on S with 1-2 oxo (=O) moieties, the cycloalkyl, and heterocyclic moieties of the foregoing $R^5$ groups are optionally substituted with 1 to 5 substituents independently selected from halo, cyano, nitro, trifluoromethyl, trifluoromethoxy, $C_1$-$C_6$ alkyl, $C_2$-$C_6$ alkenyl, $C_2$-$C_6$ alkynyl, hydroxy, —$(CR^1R^2)_qX(CR^1R^2)_rR^{12}$ wherein q is an integer from 0 to 5, and r is an integer from 0 to 5, X can be absent or represents —$N(R^{14})$—, —NH—, O, CO, —$N(R^{14})$ CO—, —$CON(R^{14})$—, —$N(R^{14})C(O)N(R^{14})$—, —$N(R^{14})S(O)_j$—, —$S(O)_jN(R^{14})$—, $S(O)_j$, wherein j is an integer from 0 to 2;

each $R^6$, $R^{6a}$ and $R^7$ are independently selected from H, $C_1$-$C_{10}$ alkyl, —$(CR^1R^2)_t(C_6$-$C_{10}$ aryl), and —$(CR^1R^2)_t$(4 to 10 membered heterocyclic), wherein t is an integer from 0 to 5, 1 or 2 ring carbon atoms of the heterocyclic group are optionally substituted with an oxo (=O) moiety, the alkyl, aryl and heterocyclic moieties of the foregoing $R^6$ and $R^7$ groups are optionally substituted with 1 to 5 substituents independently selected from halo, cyano, nitro, —$NR^1R^2$ trifluoromethyl, trifluoromethoxy, $C_1$-$C_6$ alkyl, $C_2$-$C_6$ alkenyl, $C_2$-$C_6$ alkynyl, hydroxy, $C_1$-$C_6$ alkoxy, —$(CR^1R^2)_qW(CR^1R^2)_rR^{15}$ wherein q is an integer from 0 to 5, and r is an integer from 0 to 5, W can be absent or represents $N(R^{14})$, O, alkyne, cis or trans alkene, CO, —$N(R^{14})CO$—, —$CON(R^{14})$—, —$N(R^{14})C(O)N(R^{14})$—, —$N(R^{14})S(O)_j$—, —$S(O)_jN(R^{14})$—, $S(O)_j$, wherein j is an integer from 0 to 2;

or $R^6$ and $R^7$, or $R^{6a}$ and $R^7$, when attached to the same nitrogen atom, can be taken together to form a 4 to 10 membered heterocyclic ring which may include 1 to 3 additional hetero moieties, in addition to the nitrogen to which said $R^6$, $R^{6a}$, and $R^7$ are attached, selected from N, $N(R^1)$, O, and S, provided two O atoms, two S atoms or an O and S atom are not attached directly to each other, and the foregoing $R^6$ and $R^7$ ring groups are optionally substituted with 1 to 5 substituents independently selected from halo, cyano, nitro, —$NR^1R^2$, trifluoromethyl, trifluoromethoxy, $C_1$-$C_6$ alkyl, $C_2$-$C_6$ alkenyl, $C_2$-$C_6$ alkynyl, hydroxy, $C_1$-$C_6$ alkoxy, —$(CR^1R^2)_qW(CR^1R^2)_rR^{15}$ wherein q is an integer from 0 to 5, and r is an integer from 0 to 5, W can be absent or represents $N(R^{14})$, O, alkyne, cis or trans alkene, CO, —$N(R^{14})CO$—, —$CON(R^{14})$—, —$N(R^{14})C(O)N(R^{14})$—, —$N(R^{14})S(O)_j$—, —$S(O)_jN(R^{14})$—, $S(O)_j$, wherein j is an integer from 0 to 2;

each $R^8$ is independently selected from halo, cyano, nitro, trifluoromethoxy, trifluoromethyl, azido, hydroxy, $C_3$-$C_8$ cyclic alkyl, $C_1$-$C_6$ alkoxy, $C_1$-$C_{10}$ alkyl, $C_2$-$C_6$ alkenyl, $C_2$-$C_6$ alkynyl, —$C(O)R^6$, —$C(O)OR^6$, —$OC(O)R^6$, —$NR^6C(O)R^7$, —$NR^6SO_2NR^7R^1$, —$NR^6C(O)NR^7R^2$, —$NR^6C(O)OR^7$, —$C(O)NR^6R^7$, —$NR^6R^7$, —$SO_2NR^6R^7$, —$S(O)_j(C_1$-$C_6$ alkyl) wherein j is an integer from 0 to 2, —$(CR^1R^2)_t(C_6$-$C_{10}$ aryl), —$(CR^1R^2)_t$(4 to 10 membered heterocyclic), —$(CR^1R^2)_qC(O)(CR^1R^2)_t(C_6$-$C_{10}$ aryl), —$(CR^1R^2)_qC(O)(CR^1R^2)_t$(4 to 10 membered heterocyclic), —$(CR^1R^2)_tO(CR^1R^2)_q(C_6$-$C_{10}$ aryl), —$(CR^1R^2)_tO(CR^1R^2)_q$(4 to 10 membered heterocyclic), —$(CR^1R^2)_qS(O)_j(CR^1R^2)_t(C_6$-$C_{10}$ aryl), and —$(CR^1R^2)_qS(O)_j(CR^1R^2)_t$(4 to 10 membered heterocyclic), wherein j is 0, 1 or 2, q and t are each independently an integer from 0 to 5, 1 or 2 ring carbon atoms of the heterocyclic moieties of the foregoing $R^8$ groups are optionally substituted with an oxo (=O) moiety, and the alkyl, alkenyl, alkynyl, aryl and heterocyclic moieties of the foregoing $R^8$ groups are optionally substituted with 1 to 3 substituents independently selected from halo, cyano, nitro, trifluoromethyl, trifluoromethoxy, azido, —$OR^6$, —$C(O)R^6$, —$C(O)OR^6$, —$OC(O)R^6$, —$NR^6C(O)R^7$, —$C(O)NR^6R^7$, —$NR^6R^7$, —$NR^6OR^7$, $C_1$-$C_6$ alkyl, $C_2$-$C_6$ alkenyl, $C_2$-$C_6$ alkynyl, —$(CR^1R^2)_t(C_6$-$C_{10}$ aryl), and —$(CR^1R^2)_t$(4 to 10 membered heterocyclic), wherein t is an integer from 0 to 5;

each $R^9$ is independently selected from trifluoromethyl, $C_3$-$C_8$ cyclic alkyl, $C_1$-$C_{10}$ alkyl, $C_2$-$C_6$ alkenyl, $C_2$-$C_6$ alkynyl, —$C(O)R^6$, —$C(O)OR^6$, —$C(O)NR^6R^7$, —$SO_2NR^6R^7$, —$S(O)_j(C_1$-$C_6$ alkyl) wherein j is an integer from 0 to 2, —$(CR^1R^2)_t(C_6$-$C_{10}$ aryl), —$(CR^1R^2)_t$(4 to 10 membered heterocyclic), —$(CR^1R^2)_qC(O)(CR^1R^2)_t(C_6$-$C_{10}$ aryl), —$(CR^1R^2)_qC(O)(CR^1R^2)_t$(4 to 10 membered heterocyclic), —$(CR^1R^2)_hO(CR^1R^2)_q(C_6$-$C_{10}$ aryl), —$(CR^1R^2)_hO(CR^1R^2)_q$(4 to 10 membered heterocyclic), —$(CR^1R^2)_qS(O)_j(CR^1R^2)_t(C_6$-$C_{10}$ aryl), and —$(CR^1R^2)_qS(O)_j(CR^1R^2)_t$(4 to 10 membered heterocyclic), wherein j is 0, 1 or 2, q and t are each independently an integer from 0 to 5, h is an integer from 1 to 5, 1 or 2 ring carbon atoms of the heterocyclic moieties of the foregoing $R^9$ groups are optionally substituted with an oxo (=O) moiety, and the alkyl, alkenyl, alkynyl, aryl and heterocyclic moieties of the foregoing $R^9$ groups are optionally substituted with 1 to 3 substituents independently selected from halo, cyano, nitro, trifluoromethyl, trifluoromethoxy, azido, —$OR^6$, —$C(O)R^6$, —$C(O)OR^6$, —$OC(O)R^6$, —$NR^6C(O)R^7$, —$C(O)NR^6R^7$, —$NR^6R^7$, —$NR^6OR^7$, $C_1$-$C_6$ alkyl, $C_2$-$C_6$ alkenyl, $C_2$-$C_6$ alkynyl, —$(CR^1R^2)_t(C_6$-$C_{10}$ aryl), and —$(CR^1R^2)_t$(4 to 10 membered heterocyclic), wherein t is an integer from 0 to 5;

each $R^{10}$ is independently selected from halo, cyano, nitro, trifluoromethoxy, trifluoromethyl, azido, hydroxy, $C_3$-$C_8$ cyclic alkyl, $C_1$-$C_6$ alkoxy, $C_1$-$C_6$ amino, $C_1$-$C_{10}$ alkyl, $C_2$-$C_6$ alkenyl, $C_2$-$C_6$ alkynyl, —$C(O)R^1$, —$C(O)OR^1$, —$OC(O)R^1$, —$NR^1C(O)R^2$, —$NR^1SO_2NR^2R^1$, —$NR^1C(O)NR^1R^2$, —$NR^1C(O)OR^2$, —$C(O)NR^1R^2$, —$NR^1R^2$, —$SO_2NR^1R^2$, —$S(O)_j(C_1$-$C_6$ alkyl) wherein j is an integer from 0 to 2, —$(CR^1R^2)_t(C_6$-$C_{10}$ aryl), —$(CR^1R^2)_t$(4 to 10 membered heterocyclic), —$(CR^1R^2)_qC(O)(CR^1R^2)_t(C_6$-$C_{10}$ aryl), —$(CR^1R^2)_qC(O)(CR^1R^2)_t$(4 to 10 membered heterocyclic), —$(CR^1R^2)_qO(CR^1R^2)_q(C_6$-$C_{10}$ aryl), —$(CR^1R^2)_tO(CR^1R^2)_q$(4 to 10 membered heterocyclic), —$(CR^1R^2)_qS(O)_j(CR^1R^2)_t(C_6$-$C_{10}$ aryl), and —$(CR^1R^2)_qS(O)_j(CR^1R^2)_t$(4 to 10 membered heterocyclic), wherein j is 0, 1 or 2, q and t are each independently an integer from 0 to 5, 1 or 2 ring carbon atoms of the heterocyclic moieties of the foregoing $R^{10}$ groups are optionally substituted with an oxo (=O) moiety, and the alkyl, alkenyl, alkynyl, aryl and heterocyclic moieties of the foregoing $R^{10}$ groups are optionally substituted with 1 to 3 $R^1$ substituents;

each $R^{11}$ is independently selected from the substituents provided in the definition of $R^8$ except $R^{11}$ is not azido;

$R^{12}$ is $R^6$, —$OR^6$, —$OC(O)R^6$, —$OC(O)NR^6R^7$, —$OCO_2R^6$, —$S(O)_jR^6$, —$S(O)_jNR^6R^7$, —$NR^6R^7$, —$NR^6C(O)R^7$, —$NR^6SO_2R^7$, —$NR^6C(O)NR^{6a}R^7$, —$NR^6SO_2NR^{6a}R^7$, —$NR^6CO_2R^7$, CN, —$C(O)R^6$, or halo, wherein j is an integer from 0 to 2;

$R^{14}$ is H, $R^{15}$, —$C(O)R^{15}$, —$SO_2R^{15}$, —$C(O)NR^1R^{10}$, —$SO_2NR^1R^{10}$, —$C(O)NR^{16}R^{17}$, —$SO_2NR^{16}R^{17}$, or —$CO_2R^{15}$;

$R^{15}$ is $R^{18}$, —$(CR^1R^2)_t(C_6$-$C_{10}$ aryl), —$(CR^1R^2)_t$(4 to 10 membered heterocyclic), wherein t is an integer from 0 to 5, 1 or 2 ring carbon atoms of the heterocyclic group are optionally substituted with an oxo (=O) moiety, and the aryl and heterocyclic moieties of the foregoing $R^{15}$ groups are optionally substituted with 1 to 3 $R^{10}$ substituents;

$R^{16}$ and $R^{17}$ in addition to the nitrogen to which said $R^{16}$ and $R^{17}$ are attached form a 4 to 10 membered heterocyclic ring which may include 1 to 3 additional hetero moieties, selected from N, $N(R^1)$, O, and S, provided two O atoms, two S atoms or an O and S atom are not attached directly to each other, and the 4 to 10 membered heterocyclic ring is optionally substituted with 1 to 5 substituents independently selected from halo, cyano, nitro, —$NR^1R^2$, trifluoromethyl, trifluoromethoxy, $C_1$-$C_6$ alkyl, $C_2$-$C_6$ alkenyl, $C_2$-$C_6$ alkynyl, hydroxy, and $C_1$-$C_6$ alkoxy;

$R^{18}$ is $C_1$-$C_6$ alkyl wherein each carbon not bound to a N or O atom, or to $S(O)_j$, wherein j is an integer from 0 to 2, is optionally substituted with $R^{10}$;

and wherein any of the above-mentioned substituents comprising a $CH_3$ (methyl), $CH_2$ (methylene), or CH (methine) group, which is not attached to a halogen, SO or $SO_2$ group or to a N, O or S atom, is optionally substituted with a group selected from hydroxy, halo, $C_1$-$C_4$ alkyl, $C_1$-$C_4$ alkoxy and —$NR^1R^2$.

The term "halo", as used herein, unless otherwise indicated, includes fluoro, chloro, bromo or iodo. Preferred halo groups are fluoro and chloro.

The term "alkyl", as used herein, unless otherwise indicated, includes saturated monovalent hydrocarbon radicals having straight, cyclic (including mono- or multi-cyclic moieties) or branched moieties. It is understood that for said alkyl group to include cyclic moieties it must contain at least three carbon atoms.

The term "cycloalkyl", as used herein, unless otherwise indicated, includes saturated monovalent hydrocarbon radicals having cyclic (including mono- or multi-cyclic) moieties.

The term "alkenyl", as used herein, unless otherwise indicated, includes alkyl groups, as defined above, having at least one carbon-carbon double bond.

The term "alkynyl", as used herein, unless otherwise indicated, includes alkyl groups, as defined above, having at least one carbon-carbon triple bond.

The term "aryl", as used herein, unless otherwise indicated, includes an organic radical derived from an aromatic hydrocarbon by removal of one hydrogen, such as phenyl or naphthyl.

The term "alkoxy", as used herein, unless otherwise indicated, includes —O-alkyl groups wherein alkyl is as defined above.

The term "4 to 10 membered heterocyclic", as used herein, unless otherwise indicated, includes aromatic and non-aromatic heterocyclic groups containing one or more heteroatoms each selected from O, S and N, wherein each heterocyclic group has from 4 to 10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The term "Me" means methyl, "Et" means ethyl, and "Ac" means acetyl.

In the definition of $X^1$ above, the —$(CR^1R^2)_m$— and other similar moieties, as indicated above, may vary in their definition of $R^1$ and $R^2$ for each iteration of the subscript (ie, m, k, etc) above 1. For example when m is 2 the moiety —$(CR^1R^2)_m$— may include —$CH_2C(Me)(Et)$.

The phrase "pharmaceutically acceptable salt(s)", as used herein, unless otherwise indicated, includes salts of acidic or basic groups that may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salts with various amino acids, in addition to the acids mentioned above.

In one embodiment of the invention, the $R^3$ of the compound of formula 1 is a 6-membered heterocyclic or phenyl.

In another embodiment of the invention, the $R^3$ of the compound of formula 1, is a 6-membered heterocyclic.

In another embodiment of the invention, the $R^3$ of the compound of formula 1 is phenyl.

In a preferred embodiment of the invention, the $R^3$ of the compound of formula 1 is

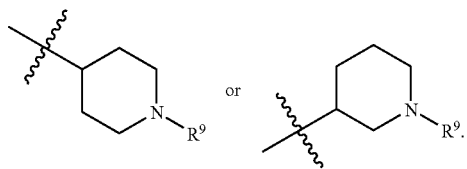

In a particularly preferred embodiment of the invention, the $R^9$ of the compound of formula 1 is independently selected from —$C(O)R^6$, or —$C(O)NR^6R^7$, p is selected from the group consisting of 1, and $R^{11}$ is selected from the group consisting of OMe, F, Cl, Br, and Me.

In another embodiment of the invention, the $R^6$ and $R^7$ of the compound of formula 1 is independently selected from $C_5$-$C_{10}$ alkyl, —$(CR^1R^2)_t(C_6$-$C_{10}$ aryl), and —$(CR^1R^2)_h$(4 to 10 membered heterocyclic) and h is an integer from 1 to 5; and $R^6$ and $R^7$, when attached to the same nitrogen atom, can be taken together to form a 5 to 10 membered heterocyclic ring.

In another embodiment of the invention, the $R^3$ of the compound of formula 1 is

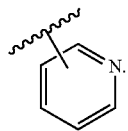

In a preferred embodiment the invention, the $R^3$ of the compound of formula 1 is

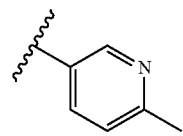

In another preferred embodiment of the invention, the compound of formula 1, wherein p is 1, and $R^{11}$ is selected from the group consisting of OMe, F, Cl, Br, and Me; and $R^3$ is

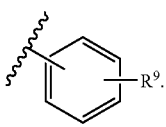

In another particularly preferred embodiment of the invention, the compound of formula 1, wherein $R^8$ is —C(O)NR$^6$R$^7$.

In another preferred embodiment of the invention, the compound of formula 1, wherein $R^3$ is

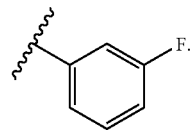

In another embodiment of the invention, the compound of formula 1, wherein A represents a fused 5 or 6-membered ring.

In another embodiment of the invention, the compound of formula 1, wherein A represents a fused 6-membered ring optionally containing 1 to 2 heteroatoms.

In another embodiment of the invention, the compound of formula 1, wherein A represents a fused 6-membered ring optionally containing 1 heteroatom.

In another embodiment of the invention, the compound of formula 1, wherein A represents a fused 6-membered ring containing 1 heteroatom.

In another preferred embodiment of the invention, the compound of formula 1, wherein Z represents N, A represents phenyl or pyridine wherein the pyridine nitrogen is located at the 5 or 7 position.

In another preferred embodiment of the invention, the compound of formula 1, wherein $R^4$ is —X(CR$^1$R$^2$)$_r$R$^5$, wherein r is an integer from 0 to 5, X can be absent or represents —N(R$^{14}$)—, —NH—, O, CO, —N(R$^{14}$)CO—, —CON(R$^{14}$)—, —N(R$^{14}$)C(O)N(R$^{14}$)—, —N(R$^{14}$)S(O)$_j$—, wherein j is an integer from 0 to 2, and $R^5$ represents NR$^6$R$^7$, NR$^1$(R$^{14}$), C(O)N(R$^1$)(R$^{14}$), —N(R$^{14}$)C(O)N(R$^1$)(R$^{14}$), —N(R$^1$)(R$^{14}$)S(O)$_j$R$^1$, —OR$^6$, —OC(O)R$^6$, —OC(O)NR$^6$R$^7$, —OCO$_2$R$^6$, —S(O)$_j$R$^6$, —S(O)$_j$NR$^6$R$^7$, —NR$^6$R$^7$, —NR$^6$C(O)R$^7$, —NR$^6$SO$_2$R$^7$, —NR$^6$C(O)NR$^{6a}$R$^7$, —NR$^6$SO$_2$NR$^{6a}$R$^7$, —NR$^6$CO$_2$R$^7$, CN, —C(O)R$^6$, wherein j is an integer from 0 to 2, $C_1$-$C_{10}$ alkyl, or $C_3$-$C_8$ cycloalkyl, In another preferred embodiment of the invention, the compound of formula 1 wherein m is an integer between 1 and 2.

In another embodiment of the invention, the compound of formula 1 wherein Z represents N, m is an integer between 1 and 2 and $R^4$ is optionally located at the 6 and or 7 position.

In another preferred embodiment of the invention, the compound of formula 1 wherein p is 1, and $R^{11}$ is selected from the group consisting of OMe, F, Cl, Br, and Me; and $R^3$ is

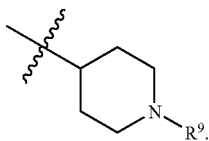

In another particularly preferred embodiment of the invention, the compound of formula 1 wherein $R^9$ is independently selected from —C(O)R$^6$, —C(O)OR$^6$, —C(O)NR$^6$R$^7$, or —SO$_2$NR$^6$R$^7$.

In another embodiment of the invention, a compound according to formula 1 selected from the group consisting of:

Cyclobutyl-{4-[4-(6-methoxy-quinazolin-4-ylamino)-2-methyl-phenoxy]-piperidin-1-yl}-methanone;

4-[4-(6-Methoxy-quinazolin-4-ylamino)-2-methyl-phenoxy]-piperidine-1-carboxylic acid (2,6-difluoro-phenyl)-amide;

1-{4-[4-(6-Methoxy-quinazolin-4-ylamino)-2-methyl-phenoxy]-piperidin-1-yl}-3,3-dimethyl-butan-1-one;

2-Cyclopropyl-1-{4-[4-(6-methoxy-quinazolin-4-ylamino)-2-methyl-phenoxy]-piperidin-1-yl}-ethanone;

4-[4-(6-Methoxy-quinazolin-4-ylamino)-2-methyl-phenoxy]-piperidine-1-carboxylic acid tert-butyl-amide;

4-[4-(6-Methoxy-quinazolin-4-ylamino)-2-methyl-phenoxy]-piperidine-1-carboxylic acid cyclopentylamide;

4-[4-(6-Methoxy-quinazolin-4-ylamino)-2-methyl-phenoxy]-piperidine-1-carboxylic acid (4-methoxy-phenyl)-amide;

4-[4-(6,7-Dimethoxy-quinazolin-4-ylamino)-2-methyl-phenoxy]-piperidine-1-carboxylic acid (2,6-difluoro-phenyl)-amide;

4-[4-(6,7-Dimethoxy-quinazolin-4-ylamino)-2-methyl-phenoxy]-piperidine-1-carboxylic acid (4-methoxy-phenyl)-amide;

{4-[4-(6,7-Dimethoxy-quinazolin-4-ylamino)-2-methyl-phenoxy]-piperidin-1-yl}-morpholin-4-yl-methanone;

4-[4-(6,7-Dimethoxy-quinazolin-4-ylamino)-2-methyl-phenoxy]-piperidine-1-carboxylic acid (2,5-difluoro-phenyl)-amide;

4-[4-(6,7-Dimethoxy-quinazolin-4-ylamino)-2-methyl-phenoxy]-piperidine-1-carboxylic acid cyclopentylamide;

1-{4-[4-(6,7-Dimethoxy-quinazolin-4-ylamino)-2-methyl-phenoxy]-piperidin-1-yl}-3,3-dimethyl-butan-1-one;

{4-[4-(6,7-Dimethoxy-quinazolin-4-ylamino)-2-methyl-phenoxy]-piperidin-1-yl}-(3-methoxy-phenyl)-methanone;

Cyclopentyl-{4-[4-(6,7-dimethoxy-quinazolin-4-ylamino)-2-methyl-phenoxy]-piperidin-1-yl}-methanone;

2-Cyclopentyl-1-{4-[4-(6,7-dimethoxy-quinazolin-4-ylamino)-2-methyl-phenoxy]-piperidin-1-yl}-ethanone;

{4-[4-(6,7-Dimethoxy-quinazolin-4-ylamino)-2-methyl-phenoxy]-piperidin-1-yl}-(tetrahydro-furan-2-yl)-methanone;
4-[4-(6,7-Dimethoxy-quinazolin-4-ylamino)-2-methyl-phenoxy]-N-(2,2-dimethyl-propyl)-benzamide;
4-[4-(6,7-Dimethoxy-quinazolin-4-ylamino)-2-methyl-phenoxy]-N-pentyl-benzamide;
N-Cyclohexyl-4-[4-(6,7-dimethoxy-quinazolin-4-ylamino)-2-methyl-phenoxy]-benzamide;
4-[4-(6,7-Dimethoxy-quinazolin-4-ylamino)-2-methyl-phenoxy]-N-(4-methoxy-phenyl)-benzamide;
4-[4-(6,7-Dimethoxy-quinazolin4-ylamino)-2-methyl-phenoxy]-N-(2-fluoro-phenyl)-benzamide;
{4-[4-(6,7-Dimethoxy-quinazolin-4-ylamino)-2-methyl-phenoxy]-phenyl-piperidin-1-yl-methanone;
4-[4-(6,7-Dimethoxy-quinazolin-4-ylamino)-2-methyl-phenoxy]-N-(2-piperidin-1-yl-ethyl)-benzamide;
3-[4-(6,7-Dimethoxy-quinazolin-4-ylamino)-2-methyl-phenoxy]-N-(2,2-dimethyl-propyl)-benzamide;
3-[4-(6,7-Dimethoxy-quinazolin-4-ylamino)-2-methyl-phenoxy]-N-pentyl-benzamide;
N-Cyclohexyl-3-[4-(6,7-dimethoxy-quinazolin-4-ylamino)-2-methyl-phenoxy]-benzamide;
3-[4-(6,7-Dimethoxy-quinazolin-4-ylamino)-2-methyl-phenoxy]-N-(4-methoxy-phenyl)-benzamide;
3-[4-(6,7-Dimethoxy-quinazolin-4-ylamino)-2-methyl-phenoxy]-N-(2-fluoro-phenyl)-benzamide;
{3-[4-(6,7-Dimethoxy-quinazolin-4-ylamino)-2-methyl-phenoxy]-phenyl}-piperidin-1-yl-methanone;
3-[4-(6,7-Dimethoxy-quinazolin-4-ylamino)-2-methyl-phenoxy]-N-(2-piperidin-1-yl-ethyl)-benzamide;
3-[4-(6,7-Dimethoxy-quinazolin-4-ylamino)-2-methyl-phenoxy]-N-(1,1-dimethyl-propyl)-benzamide;
4-[4-(6,7-Dimethoxy-quinazolin-4-ylamino)-2-methyl-phenoxy]-N-(1,1-dimethyl-propyl)-benzamide;
4-[4-(6,7-Dimethoxy-quinazolin-4-ylamino)-2-methyl-phenoxy]-piperidine-1-carboxylic acid o-tolyl-amide;
4-[4-(6,7-Dimethoxy-quinazolin-4-ylamino)-2-methyl-phenoxy]-piperidine-1-carboxylic acid (4-chloro-phenyl)-amide;
4-[4-(6,7-Dimethoxy-quinazolin-4-ylamino)-2-methyl-phenoxy]-piperidine-1-carboxylic acid (2-chloro-phenyl)-amide;
4-[4-(6,7-Dimethoxy-quinazolin-4-ylamino)-2-methyl-phenoxy]-piperidine-1-carboxylic acid (2-methoxy-phenyl)-amide;
4-[4-(6,7-Dimethoxy-quinazolin-4-ylamino)-2-methyl-phenoxy]-piperidine-1-carboxylic acid (2-fluoro-phenyl)-amide;
4-[4-(6,7-Dimethoxy-quinazolin-4-ylamino)-2-methyl-phenoxy]-piperidine-1-carboxylic acid (4-fluoro-phenyl)-amide;
4-[4-(6,7-Dimethoxy-quinazolin-4-ylamino)-2-methyl-phenoxy]-piperidine-1-carboxylic acid (3-trifluoromethyl-phenyl)-amide;
4-[4-(6,7-Dimethoxy-quinazolin-4-ylamino)-2-methyl-phenoxy]-piperidine-1-carboxylic acid (2,5-difluoro-phenyl)-amide;
4-[4-(6,7-Dimethoxy-quinazolin-4-ylamino)-2-methyl-phenoxy]-piperidine-1-carboxylic acid (3-fluoro-phenyl)-amide;
4-[4-(6,7-Dimethoxy-quinazolin-4-ylamino)-2-methyl-phenoxy]-piperidine-1-carboxylic acid (2-trifluoromethyl-phenyl)-amide;
4-[4-(6,7-Dimethoxy-quinazolin-4-ylamino)-2-methyl-phenoxy]-piperidine-1-carboxylic acid (2,6-dichloro-phenyl)-amide;
4-[4-(6,7-Dimethoxy-quinazolin-4-ylamino)-2-methyl-phenoxy]-piperidine-1-carboxylic acid (4-trifluoromethyl-phenyl)-amide;
4-[4-(6,7-Dimethoxy-quinazolin-4-ylamino)-2-methyl-phenoxy]-piperidine-1-carboxylic acid (2,6-dimethyl-phenyl)-amide;
4-[4-(6,7-Dimethoxy-quinazolin-4-ylamino)-2-methyl-phenoxy]-piperidine-1-carboxylic acid (4-dimethylamino-phenyl)-amide;
4-[4-(6,7-Dimethoxy-quinazolin-4-ylamino)-2-methyl-phenoxy]-piperidine-1-carboxylic acid (3,5-difluoro-phenyl)-amide;
Cyclopentyl-{4-[2-methyl-4-(6-pyrrolidin-1-yl-pyrido[3,4-d]pyrimidin-4-ylamino)-phenoxy]-piperidin-1-yl}-methanone;
Cyclopentyl-(4-{2-methyl-4-[6-(4-methyl-piperazin-1-yl)-pyrido[3,4-d]pyrimidin-4-ylamino]-phenoxy}-piperidin-1-yl)-methanone;
Cyclopentyl-{4-[4-(6-dimethylamino-pyrido[3,4-d]pyrimidin-4-ylamino)-2-methyl-phenoxy]-piperidin-1-yl}-methanone;
3-[2-Methyl-4-(6-morpholin-4-yl-pyrido[3,4-d]pyrimidin-4-ylamino)-phenoxy]-benzoic acid tert-butyl ester;
3-{2-Methyl-4-[6-(2-morpholin-4-yl-ethylamino)-pyrido[3,4-d]pyrimidin-4-ylamino]-phenoxy}-benzoic acid tert-butyl ester;
3-{2-Methyl-4-[6-(4-methyl-piperazin-1-yl)-pyrido[3,4-d]pyrimidin-4-ylamino]-phenoxy}-benzoic acid tert-butyl ester;
3-[2-Methyl-4-(6-pyrrolidin-1-yl-pyrido[3,4-d]pyrimidin-4-ylamino)-phenoxy]-benzoic acid tert-butyl ester;
Cyclopentyl-{4-[2-methyl-4-(6-morpholin-4-yl-pyrido[3,4-d]pyrimidin-4-ylamino)-phenoxy]-piperidin-1-yl}-methanone;
N-Cyclohexyl-3-[4-(6-dimethylamino-pyrido[3,4-d]pyrimidin-4-ylamino)-2-methyl-phenoxy]-benzamide;
3-[4-(6-Dimethylamino-pyrido[3,4-d]pyrimidin-4-ylamino)-2-methyl-phenoxy]-N-(2,2-dimethyl-propyl)-benzamide;
2-Cyclopentyl-1-{4-[4-(6-dimethylamino-pyrido[3,4-d]pyrimidin-4-ylamino)-2-methyl-phenoxy]-piperidin-1-yl}-ethanone;
4-[2-Methyl-4-(6-morpholin-4-yl-pyrido[3,4-d]pyrimidin-4-ylamino)-phenoxy]-piperidine-1-carboxylic acid (2,6-difluoro-phenyl)-amide;
4-{2-Methyl-4-[6-(4-methyl-piperazin-1-yl)-pyrido[3,4-d]pyrimidin-4-ylamino]-phenoxy}-piperidine-1-carboxylic acid (2,6-difluoro-phenyl)-amide;
4-[4-(6-Dimethylamino-pyrido[3,4-d]pyrimidin-4-ylamino)-2-methyl-phenoxy]-piperidine-1-carboxylic acid (2,6-difluoro-phenyl)-amide;
4-[2-Methyl-4-(6-pyrrolidin-1-yl-pyrido[3,4-d]pyrimidin-4-ylamino)-phenoxy]-piperidine-1-carboxylic acid (2,6-difluoro-phenyl)-amide;
Cyclopentyl-(4-{2-methyl-4-[6-(2-morpholin-4-yl-ethylamino)-pyrido[3,4-d]pyrimidin-1-ylamino]-phenoxy}-piperidin-1-yl)-methanone;
2-Cyclopentyl-1-{4-[2-methyl-4-(6-morpholin-4-yl-pyrido[3,4-d]pyrimidin-4-ylamino)-phenoxy]-piperidin-1-yl}-ethanone;
2-Cyclopentyl-1-(4-{2-methyl-4-[6-(4-methyl-piperazin-1-yl)-pyrido[3,4-d]pyrimidin-4-ylamino]-phenoxy}-piperidin-1-yl)-ethanone;
2-Cyclopentyl-1-{4-[2-methyl-4-(6-pyrrolidin-1-yl-pyrido[3,4-d]pyrimidin-4-ylamino)-phenoxy]-piperidin-1-yl}-ethanone;

2-Cyclopentyl-1-(4-{2-methyl-4-[6-(2-morpholin-4-yl-ethylamino)-pyrido[3,4-d]pyrimidin-4-ylamino]-phenoxy}-piperidin-1-yl)-ethanone;
N-(2-Fluoro-phenyl)-3-[2-methyl-4-(6-morpholin-4-yl-pyrido[3,4-d]pyrimidin-4-ylamino)-phenoxy]-benzamide;
N-Cyclohexyl-3-[2-methyl-4-(6-morpholin-4-yl-pyrido[3,4-d]pyrimidin-4-ylamino)-phenoxy]-benzamide;
N-tert-Butyl-3-[2-methyl-4-(6-morpholin-4-yl-pyrido[3,4-d]pyrimidin-4-ylamino)-phenoxy]-benzamide;
N-(1,1-Dimethyl-propyl)-3-[2-methyl-4-(6-morpholin-4-y-pyrido[3,4-d]pyrimidin-4-ylamino)-phenoxy]-benzamide;
N-(2,2-Dimethyl-propyl)-3-[2-methyl-4-(6-morpholin-4-yl-pyrido[3,4-d]pyrimidin-4-ylamino)-phenoxy]-benzamide;
N-Cyclohexyl-3-{2-methyl-4-[6-(2-morpholin-4-yl-ethylamino)-pyrido[3,4-d]pyrimidin-4-ylamino]-phenoxy}-benzamide;
4-[4-(6-Dimethylamino-pyrido[3,4-d]pyrimidin-4-ylamino)-2-methyl-phenoxy]-benzoic acid tert-butyl ester;
4-[2-Methyl-4-(6-morpholin-4-yl-pyrido[3,4-d]pyrimidin-4-ylamino)-phenoxy]-benzoic acid tert-butyl ester;
4-{2-Methyl-4-[6-(2-morpholin-4-yl-ethylamino)-pyrido[3,4-d]pyrimidin-4-ylamino]-phenoxy}-benzoic acid tert-butyl ester;
4-{2-Methyl-4-[6-(4-methyl-piperazin-1-yl)-pyrido[3,4-d]pyrimidin-4-ylamino]-phenoxy}-benzoic acid tert-butyl ester;
4-[2-Methyl-4-(6-pyrrolidin-1-yl-pyrido[3,4-d]pyrimidin-4-ylamino)-phenoxy]-benzoic acid tert-butyl ester;
N-tert-Butyl-3-{2-methyl-4-[6-(2-morpholin-4-yl-ethylamino)-pyrido[3,4-d]pyrimidin-4-ylamino]-phenoxy}-benzamide;
N-(2-Fluoro-phenyl)-3-{2-methyl-4-[6-(2-morpholin-4-yl-ethylamino)-pyrido[3,4-d]pyrimidin-4-ylamino]-phenoxy}-benzamide;
N-(1,1-Dimethyl-propyl)-3-{2-methyl-4-[6-(2-morpholin-4-yl-ethylamino)-pyrido[3,4-d]pyrimidin-4-ylamino]-phenoxy}-benzamide;
N-(2,2-Dimethyl-propyl)-3-{2-methyl-4-[6-(2-morpholin-4-yl-ethylamino)-pyrido[3,4-d]pyrimidin-4-ylamino]-phenoxy}-benzamide;
N-Cyclohexyl-3-{2-methyl-4-[6-(4-methyl-piperazin-1-yl)-pyrido[3,4-d]pyrimidin-4-ylamino]-phenoxy}-benzamide;
N-tert-Butyl-3-{2-methyl-4-[6-(4-methyl-piperazin-1-yl)-pyrido[3,4-d]pyrimidin-4-ylamino]-phenoxy}-benzamide;
N-(2-Fluoro-phenyl)-3-{2-methyl-4-[6-(4-methyl-piperazin-1-yl)-pyrido[3,4-d]pyrimidin-4-ylamino]-phenoxy}-benzamide;
N-(1,1-Dimethyl-propyl)-3-{2-methyl-4-[6-(4-methyl-piperazin-1-yl)-pyrido[3,4-d]pyrimidin-4-ylamino]-phenoxy}-benzamide;
N-(2,2-Dimethyl-propyl)-3-{2-methyl-4-[6-(4-methyl-piperazin-1-yl)-pyrido[3,4-d]pyrimidin-4-ylamino]-phenoxy}-benzamide;
N-Cyclohexyl-3-[2-methyl-4-(6-pyrrolidin-1-yl-pyrido[3,4-d]pyrimidin-4-ylamino)-phenoxy]-benzamide;
N-tert-Butyl-3-[2-methyl-4-(6-pyrrolidin-1-yl-pyrido[3,4-d]pyrimidin-4-ylamino)-phenoxy]-benzamide;
N-(2-Fluoro-phenyl)-3-[2-methyl-4-(6-pyrrolidin-1-yl-pyrido[3,4-d]pyrimidin-4-ylamino)-phenoxy]-benzamide;
N-(1,1-Dimethyl-propyl)-3-[2-methyl-4-(6-pyrrolidin-1-yl-pyrido[3,4-d]pyrimidin-4-ylamino)-phenoxy]-benzamide;
N-(2,2-Dimethyl-propyl)-3-[2-methyl-4-(6-pyrrolidin-1-yl-pyrido[3,4-d]pyrimidin-4-ylamino)-phenoxy]-benzamide;
N-Cyclohexyl-4-[2-methyl-4-(6-morpholin-4-yl-pyrido[3,4-d]pyrimidin-4-ylamino)-phenoxy]-benzamide;
N-(2-Fluoro-phenyl)-4-[2-methyl-4-(6-morpholin-4-yl-pyrido[3,4-d]pyrimidin-4-ylamino)-phenoxy]-benzamide;
N-tert-Butyl-4-[2-methyl-4-(6-morpholin-4-yl-pyrido[3,4-d]pyrimidin-4-ylamino)-phenoxy]-benzamide;
N-(1,1-Dimethyl-propyl)-4-[2-methyl-4-(6-morpholin-4-yl-pyrido[3,4-d]pyrimidin-4-ylamino)-phenoxy]-benzamide;
N-(2,2-Dimethyl-propyl)-4-[2-methyl-4-(6-morpholin-4-yl-pyrido[3,4-d]pyrimidin-4-ylamino)-phenoxy]-benzamide;
N-Cyclohexyl-4-[4-(6-dimethylamino-pyrido[3,4-d]pyrimidin-4-ylamino)-2-methyl-phenoxy]-benzamide;
4-[4-(6-Dimethylamino-pyrido[3,4-d]pyrimidin-4-ylamino)-2-methyl-phenoxy]-N-(2-fluoro-phenyl)-benzamide;
N-tert-Butyl-4-[4-(6-dimethylamino-pyrido[3,4-d]pyrimidin-4-ylamino)-2-methyl-phenoxy]-benzamide;
4-[4-(6-Dimethylamino-pyrido[3,4-d]pyrimidin-4-ylamino)-2-methyl-phenoxy]-N-(1,1-dimethyl-propyl)-benzamide;
4-[4-(6-Dimethylamino-pyrido[3,4-d]pyrimidin-4-ylamino)-2-methyl-phenoxy]-N-(2,2-dimethyl-propyl)-benzamide;
N-Cyclohexyl-4-{2-methyl-4-[6-(2-morpholin-4-yl-ethylamino)-pyrido[3,4-d]pyrimidin-4-ylamino]-phenoxy}-benzamide;
N-(2-Fluoro-phenyl)-4-{2-methyl-4-[6-(2-morpholin-4-yl-ethylamino)-pyrido[3,4-d]pyrimidin-4-ylamino]-phenoxy}-benzamide;
N-tert-Butyl-4-{2-methyl-4-[6-(2-morpholin-4-yl-ethylamino)-pyrido[3,4-d]pyrimidin-4-ylamino]-phenoxy}-benzamide;
N-(1,1-Dimethyl-propyl)-4-{2-methyl-4-[6-(2-morpholin-4-yl-ethylamino)-pyrido[3,4-d]pyrimidin-4-ylamino]-phenoxy}-benzamide;
N-(2,2-Dimethyl-propyl)-4-{2-methyl-4-[6-(2-morpholin-4-yl-ethylamino)-pyrido[3,4-d]pyrimidin-4-ylamino]-phenoxy}-benzamide;
N-Cyclohexyl-4-{2-methyl-4-[6-(4-methyl-piperazin-1-yl)-pyrido[3,4-d]pyrimidin-4-ylamino]-phenoxy}-benzamide;
N-(2-Fluoro-phenyl)-4-{2-methyl-4-[6-(4-methyl-piperazin-1-yl)-pyrido[3,4-d]pyrimidin-4-ylamino]-phenoxy}-benzamide;
N-tert-Butyl-4-{2-methyl-4-[6-(4-methyl-piperazin-1-yl)-pyrido[3,4-d]pyrimidin-4-ylamino]-phenoxy}-benzamide;
N-(1,1-Dimethyl-propyl)-4-{2-methyl-4-[6-(4-methyl-piperazin-1-yl)-pyrido[3,4-d]pyrimidin-4-ylamino]-phenoxy}-benzamide;
N-(2,2-Dimethyl-propyl)-4-{2-methyl-4-[6-(4-methyl-piperazin-1-yl)-pyrido[3,4-d]pyrimidin-4-ylamino]-phenoxy}-benzamide;
N-Cyclohexyl-4-[2-methyl-4-(6-pyrrolidin-1-yl-pyrido[3,4-d]pyrimidin-4-ylamino)-phenoxy]-benzamide;
N-(2-Fluoro-phenyl)-4-[2-methyl-4-(6-pyrrolidin-1-yl-pyrido[3,4-d]pyrimidin-4-ylamino)-phenoxy]-benzamide;
N-tert-Butyl-4-[2-methyl-4-(6-pyrrolidin-1-yl-pyrido[3,4-d]pyrimidin-4-ylamino)-phenoxy]-;
N-(1,1-Dimethyl-propyl)-4-[2-methyl-4-(6-pyrrolidin-1-yl-pyrido[3,4-d]pyrimidin-4-ylamino)-phenoxy]-benzamide;

N-(2,2-Dimethyl-propyl)-4-[2-methyl-4-(6-pyrrolidin-1-yl-pyrido[3,4-d]pyrimidin-4-ylamino)-phenoxy]-benzamide;

[3-Methyl-4-(piperidin-4-yloxy)-phenyl]-(6-morpholin-4-yl-pyrido[3,4-d]pyrimidin-4-yl)-amine;

Cyclopentyl-{4-[2-methyl-4-(6-methylamino-pyrido[3,4-d]pyrimidin-4-ylamino)-phenoxy]-piperidin-1-yl}-methanone;

{4-[2-Methyl-4-(6-morpholin-4-yl-pyrido[3,4-d]pyrimidin-4-ylamino)-phenoxy]-piperidin-1-yl}-morpholin-4-yl-methanone;

{4-[2-Methyl-4-(6-morpholin-4-yl-pyrido[3,4-d]pyrimidin-4-ylamino)-phenoxy]-piperidin-1-yl}-(tetrahydro-furan-2-yl)-methanone;

4-[2-Methyl-4-(6-morpholin-4-yl-pyrido[3,4-d]pyrimidin-4-ylamino)-phenoxy]-piperidine-1-carboxylic acid (4-methoxy-phenyl)-amide (3-Methoxy-phenyl)-{4-[2-methyl-4-(6-morpholin-4-yl-pyrido[3,4-d]pyrimidin-4-ylamino)-phenoxy]-piperidin-1-yl}-methanone;

4-[2-Methyl-4-(6-morpholin-4-yl-pyrido[3,4-d]pyrimidin-4-ylamino)-phenoxy]-piperidine-1-carboxylic acid tert-butylamide;

4-[2-Methyl-4-(6-morpholin-4-yl-pyrido[3,4-d]pyrimidin-4-ylamino)-phenoxy]-piperidine-1-carboxylic acid p-tolylamide;

4-[2-Methyl-4-(6-morpholin-4-yl-pyrido[3,4-d]pyrimidin-4-ylamino)-phenoxy]-piperidine-1-carboxylic acid (2,5-difluoro-phenyl)-amide;

2-Dimethylamino-1-{4-[2-methyl-4-(6-morpholin-4-yl-pyrido[3,4-d]pyrimidin-4-phenoxy]-piperidin-1-yl}-ethanone;

4-[2-Methyl-4-(6-morpholin-4-yl-pyrido[3,4-d]pyrimidin-4-ylamino)-phenoxy]-piperidine-1-carboxylic acid (2,4-difluoro-phenyl)-amide;

4-[2-Methyl-4-(6-morpholin-4-yl-pyrido[3,4-d]pyrimidin-4-ylamino)-phenoxy]-piperidine-1-carboxylic acid cyclopentylamide;

3,3-Dimethyl-1-{4-[2-methyl-4-(6-morpholin-4-yl-pyrido[3,4-d]pyrimidin-4-ylamino)-phenoxy]-piperidin-1-yl}-butan-1-one;

4-[2-Methyl-4-(6-morpholin-4-yl-pyrido[3,4-d]pyrimidin-4-ylamino)-phenoxy]-piperidine-1-carboxylic acid (3,5-difluoro-phenyl)-amide;

4-[4-(6-Dimethylamino-pyrido[3,4-d]pyrimidin-4-ylamino)-2-methyl-phenoxy]-piperidine-1-carboxylic acid tert-butylamide;

{4-[4-(6-Dimethylamino-pyrido[3,4-d]pyrimidin-4-ylamino)-2-methyl-phenoxy]-piperidin-1-yl}-(3-methoxy-phenyl)-methanone;

4-[4-(6-Dimethylamino-pyrido[3,4-d]pyrimidin-4-ylamino)-2-methyl-phenoxy]-piperidine-1-carboxylic acid (3,5-difluoro-phenyl)-amide;

N,N-6,6-Dimethyl-N-4-[3-methyl-4-(piperidin-4-yloxy)-phenyl]-pyrido[3,4-d]pyrimidine-4,6-diamine;

4-[4-(6-Dimethylamino-pyrido[3,4-d]pyrimidin-4-ylamino)-2-methyl-phenoxy]-piperidine-1-carboxylic acid tert-butyl ester;

{4-[4-(6-Dimethylamino-pyrido[3,4-d]pyrimidin-4-ylamino)-2-methyl-phenoxy]-piperidin-1-yl}-morpholin-4-yl-methanone;

4-[4-(6-Dimethylamino-pyrido[3,4-d]pyrimidin-4-ylamino)-2-methyl-phenoxy]-piperidine-1-carboxylic acid (4-methoxy-phenyl)-amide;

4-[4-(6-Dimethylamino-pyrido[3,4-d]pyrimidin-4-ylamino)-2-methyl-phenoxy]-piperidine-1-carboxylic acid cyclopentylamide;

4-[4-(6-Dimethylamino-pyrido[3,4-d]pyrimidin-4-ylamino)-2-methyl-phenoxy]-piperidine-1-carboxylic acid (2,4-difluoro-phenyl)-amide;

4-[4-(6-Dimethylamino-pyrido[3,4-d]pyrimidin-4-ylamino)-2-methyl-phenoxy]-piperidine-1-carboxylic acid p-tolylamide;

4-[4-(6-Dimethylamino-pyrido[3,4-d]pyrimidin-4-ylamino)-2-methyl-phenoxy]-piperidine-1-carboxylic acid (2,5-difluoro-phenyl)-amide;

1-{4-[4-(6-Dimethylamino-pyrido[3,4-d]pyrimidin-4-ylamino)-2-methyl-phenoxy]-piperidin-1-yl}-3,3-dimethyl-butan-1-one;

4-[4-(6-Dimethylamino-pyrido[3,4-d]pyrimidin-4-ylamino)-2-methyl-phenoxy]-piperidine-1-carboxylic acid (3,5-dichloro-phenyl)-amide;

{4-[4-(6-Dimethylamino-pyrido[3,4-d]pyrimidin-4-ylamino)-2-methyl-phenoxy]-piperidin-1-yl}-(tetrahydro-furan-2-yl)-methanone;

N-6-Methyl-N-4-[3-methyl-4-(piperidin-4-yloxy)-phenyl]-pyrido[3,4-d]pyrimidine-4,6-diamine;

4-[2-Methyl-4-(6-methylamino-pyrido[3,4-d]pyrimidin-4-ylamino)-phenoxy]-piperidine-1-carboxylic acid (2,6-difluoro-phenyl)-amide;

N-(2,2-Dimethyl-propyl)-4-[2-methyl-4-(6-methylamino-pyrido[3,4-d]pyrimidin-4-ylamino)-phenoxy]-benzamide;

4-[2-Chloro-4-(6-methylamino-pyrido[3,4-d]pyrimidin-4-ylamino)-phenoxy]-piperidine-1-carboxylic acid (2,6-difluoro-phenyl)-amide;

4-[2-Chloro-4-(6-dimethylamino-pyrido[3,4-d]pyrimidin-4-ylamino)-phenoxy]-piperidine-1-carboxylic acid (2,6-difluoro-phenyl)-amide;

4-[4-(6-Azetidin-1-yl-pyrido[3,4-d]pyrimidin-4-ylamino)-2-chloro-phenoxy]-piperidine-1-carboxylic acid (2,6-difluoro-phenyl)-amide;

4-[2-Chloro-4-(6-pyrrolidin-1-yl-pyrido[3,4-d]pyrimidin-4-ylamino)-phenoxy]-piperidine-1-carboxylic acid (2,6-difluoro-phenyl)-amide;

4-[2-Chloro-4-(6-piperidin-1-yl-pyrido[3,4-d]pyrimidin-4-ylamino)-phenoxy]-piperidine-1-carboxylic acid (2,6-difluoro-phenyl)-amide;

4-[4-(6-Dimethylamino-pyrido[3,4-d]pyrimidin-4-ylamino)-2-methoxy-phenoxy]piperidine-1-carboxylic acid (2,6-difluoro-phenyl)-amide;

4-[4-(6-Azetidin-1-yl-pyrido[3,4-d]pyrimidin-4-ylamino)-2-methoxy-phenoxy]-piperidine-1-carboxylic acid (2,6-difluoro-phenyl)-amide;

4-{4-[6-(Ethyl-methyl-amino)-pyrido[3,4-d]pyrimidin-4-ylamino]-2-methoxy-phenoxy}-piperidine-1-carboxylic acid (2,6-difluoro-phenyl)-amide;

4-[2-Methoxy-4-(6-pyrrolidin-1-yl-pyrido[3,4-d]pyrimidin-4-ylamino)-phenoxy]-piperidine-1-carboxylic acid (2,6-difluoro-phenyl)-amide;

4-[2-Methoxy-4-(6-piperidin-1-yl-pyrido[3,4-d]pyrimidin-4-ylamino)-phenoxy]-piperidine-1-carboxylic acid (2,6-difluoro-phenyl)-amide;

4-[2-Methoxy-4-(6-morpholin-4-yl-pyrido[3,4-d]pyrimidin-4-ylamino)-phenoxy]-piperidine-1-carboxylic acid (2,6-difluoro-phenyl)-amide;

{4-[2-Chloro-4-(6-methylamino-pyrido[3,4-d]pyrimidin-4-ylamino)-phenoxy]-piperidin-1-yl}-cyclopentyl-methanone;

{4-[2-Chloro-4;-(6-dimethylamino-pyrido[3,4-d]pyrimidin-4-ylamino)-phenoxy]-piperidin-1-yl}-cyclopentyl-methanone;

{4-[4-(6-Azetidin-1-yl-pyrido[3,4-d]pyrimidin-4-ylamino)-2-chloro-phenoxy]-piperidin-1-yl}-cyclopentyl-methanone;
{4-[2-Chloro-4-(6-cyclopropylamino-pyrido[3,4-d]pyrimidin-4-ylamino)-phenoxy]-piperidin-1-yl}-cyclopentyl-methanone;
(4-{2-Chloro-4-[6-(ethyl-methyl-amino)-pyrido[3,4-d]pyrimidin-4-ylamino]-phenoxy}-piperidin-1-yl)-cyclopentyl-methanone;
{4-[2-Chloro-4-(6-isopropylamino-pyrido[3,4-d]pyrimidin-4-ylamino)-phenoxy]-piperidin-1-yl}-cyclopentyl-methanone;
(4-{2-Chloro-4-[6-(2-hydroxy-ethylamino)-pyrido[3,4-d]pyrimidin-4-ylamino]-phenoxy}-piperidin-1-yl)-cyclopentyl-methanone;
{4-[2-Chloro-4-(6-pyrrolidin-1-yl-pyrido[3,4-d]pyrimidin-4-ylamino)-phenoxy]-piperidin-1-yl}-cyclopentyl-methanone;
{4-[2-Chloro-4-(6-diethylamino-pyrido[3,4-d]pyrimidin-4-ylamino)-phenoxy]-piperidin-1-yl}-cyclopentyl-methanone;
(4-{2-Chloro-4-[6-(2-methoxy-ethylamino)-pyrido[3,4-d]pyrimidin-4-ylamino]-phenoxy}-piperidin-1-yl)-cyclopentyl-methanone;
{4-[2-Chloro-4-(6-piperidin-1-yl-pyrido[3,4-d]pyrimidin-4-ylamino)-phenoxy]-piperidin-1-yl}-cyclopentyl-methanone;
{4-[2-Chloro-4-(6-morpholin-4-yl-pyrido[3,4-d]pyrimidin-4-ylamino)-phenoxy]-piperidin-1-yl}-cyclopentyl-methanone;
2-{4-[3-Chloro-4-(1-cyclopentanecarbonyl-piperidin-1-yloxy)-phenylamino]-pyrido[3,4-d]pyrimidin-6-ylamino}-acetamide;
(4-{2-Chloro-4-[6-(2-methanesulfonyl-ethylamino)-pyrido[3,4-d]pyrimidin-4-ylamino]-phenoxy}-piperidin-1-yl)-cyclopentyl-methanone;
Cyclopentyl-{4-[2-methoxy-4-(6-methylamino-pyrido[3,4-d]pyrimidin-4-ylamino)-phenoxy]-piperidin-1-yl}-methanone;
Cyclopentyl-(4-[4-(6-dimethylamino-pyrido[3,4-d]pyrimidin-4-ylamino)-2-methoxy-phenoxy]-piperidin-1-y}-methanone;
{4-[4-(6-Azetidin-1-yl-pyrido[3,4-d]pyrimidin-4-ylamino)-2-methoxy-phenoxy]-piperidin-1-yl}-cyclopentyl-methanone;
Cyclopentyl-{4-[4-(6-cyclopropylamino-pyrido[3,4-d]pyrimidin-4-ylamino)-2-methoxy-phenoxy]-piperidin-1-yl}-methanone;
Cyclopentyl-(4-{4-[6-(ethyl-methyl-amino)-pyrido[3,4-d]pyrimidin-4-ylamino]-2-methoxy-phenoxy}-piperidin-1-yl)-methanone;
Cyclopentyl-{4-[4-(6-isopropylamino-pyrido[3,4-d]pyrimidin-4-ylamino)-2-methoxy-phenoxy]-piperidin-1-yl}-methanone;
Cyclopentyl-(4-{4-[6-(2-hydroxy-ethylamino)-pyrido[3,4-d]pyrimidin-4-ylamino]-2-methoxy-phenoxy}-piperidin-1-yl)-methanone;
Cyclopentyl-{4-[2-methoxy-4-(6-pyrrolidin-1-yl-pyrido[3,4-d]pyrimidin-4-ylamino)-phenoxy]-piperidin-1-yl}-methanone;
Cyclopentyl-{4-[4-(6-diethylamino-pyrido[3,4-d]pyrimidin-4-ylamino)-2-methoxy-phenoxy]-piperidin-1-yl}-methanone;
Cyclopentyl-(4-{2-methoxy-4-[6-(2-methoxy-ethylamino)-pyrido[3,4-d]pyrimidin-4-ylamino]-phenoxy}-piperidin-1-yl)-methanone;
Cyclopentyl-{4-[2-methoxy-4-(6-piperidin-1-yl-pyrido[3,4-d]pyrimidin-4-ylamino)-phenoxy]-piperidin-1-yl}-methanone;
Cyclopentyl-{4-[2-methoxy-4-(6-morpholin-4-yl-pyrido[3,4-d]pyrimidin-4-ylamino)-phenoxy]-piperidin-1-yl}-methanone;
Cyclopentyl-(4-{4-[6-(2-methanesulfonyl-ethylamino)-pyrido[3,4-d]pyrimidin-4-ylamino]-2-methoxy-phenoxy}-piperidin-1-yl)-methanone and the pharmaceutically acceptable salts, prodrugs and solvates of the foregoing compounds.

In another embodiment of the invention, a compound according to claim 1 selected from the group consisting of:
N6,N6-Dimethyl-N4-[3-methyl-4-(6-methyl-pyridin-3-yloxy)-phenyl]-quinazoline-4,6-diamine;
(6-{5-[(2-Methanesulfonyl-ethylamino)-methyl]-furan-2-yl}-quinazolin-4-yl)-[3-methyl-4-(6-methyl-pyridin-3-yloxy)-phenyl]-amine;
N-{4-[3-Methyl-4-(6-methyl-pyridin-3-yloxy)-phenylamino]-quinazolin-6-yl}-acrylamide;
[3-Methyl-4-(6-methyl-pyridin-3-yloxy)-phenyl]-(6-morpholin-4-yl-quinazolin-4-yl)-amine;
N4-[4-(3-Fluoro-phenoxy)-3-methoxy-phenyl]-N6,N6-dimethyl-quinazoline-4,6-diamine;
[4-(3-Fluoro-phenoxy)-3-methoxy-phenyl]-(6-{5-[(2-methanesulfonyl-ethylamino)-methyl]-furan-2-yl}-quinazolin-4-yl)-amine;
N-{4-[4-(3-Fluoro-phenoxy)-3-methoxy-phenylamino]-quinazolin-6-yl}-acrylamide;
[4-(3-Fluoro-phenoxy)-3-methoxy-phenyl]-(6-morpholin-4-yl-quinazolin-4-yl)-amine;
4-[4-(6-Dimethylamino-quinazolin-4-ylamino)-2-methyl-phenoxy]-N-(2,2-dimethyl-propyl)-benzamide;
N-(2,2-Dimethyl-propyl)-4-[4-(6-{5-[(2-methanesulfonyl-ethylamino)-methyl]-furan-2-yl}-quinazolin-4-ylamino)-2-methyl-phenoxy]-benzamide;
4-[4-(6-Acryloylamino-quinazolin-4-ylamino)-2-methyl-phenoxy]-N-(2,2-dimethyl-propyl)-benzamide;
N-(2,2-Dimethyl-propyl)-4-[2-methyl-4-(6-morpholin-4-yl-quinazolin-4-ylamino)-phenoxy]-benzamide;
N-tert-Butyl-3-[4-(6-dimethylamino-quinazolin-4-ylamino)-2-methyl-phenoxy]-benzamide;
N-tert-Butyl-3-[4-(6-{5-[(2-methanesulfonyl-ethylamino)-methyl]-furan-2-yl}-quinazolin-4-ylamino)-2-methyl-phenoxy]-benzamide;
(6-{2-[(2-Methanesulfonyl-ethylamino)-methyl]-thiazol-4-yl}-quinazolin-4-yl)-[3-methyl-4-(6-methyl-pyridin-3-yloxy)-phenyl]-amine;
{6-[5-(1,1-Dioxo-thiomorpholin-4-ylmethyl)-furan-2-yl]-quinazolin-4-yl}-[3-methyl-4-(6-methyl-pyridin-3-yloxy)-phenyl]-amine;
3-[4-(6-Acryloylamino-quinazolin-4-ylamino)-2-methyl-phenoxy]-N-tert-butyl-benzamide;
N-tert-Butyl-3-[2-methyl-4-(6-morpholin-4-yl-quinazolin-4-ylamino)-phenoxy]-benzamide;
Cyclobutyl-{4-[4-(6-dimethylamino-quinazolin-4-ylamino)-2-methyl-phenoxy]-piperidin-1-yl}-methanone;
Cyclobutyl-{4-[4-(6-{5-[(2-methanesulfonyl-ethylamino)-methyl]-furan-2-yl}-quinazolin-4-ylamino)-2-methyl-phenoxy]-piperidin-1-yl}-methanone;
N-{4-[4-(1-Cyclobutanecarbonyl-piperidin-4-yloxy)-3-methyl-phenylamino]-quinazolin-6-yl}-acrylamide;
Cyclobutyl-{4-[2-methyl-4-(6-morpholin-4-yl-quinazolin-4-ylamino)-phenoxy]-piperidin-1-yl}-methanone;

4-[4-(6-Dimethylamino-quinazolin-4-ylamino)-2-methyl-phenoxy]-piperidine-1-carboxylic acid (2,6-difluoro-phenyl)-amide;

4-[4-(6-{5-[(2-Methanesulfonyl-ethylamino)-methyl]-furan-2-yl}-quinazolin-4-ylamino)-2-methyl-phenoxy]-piperidine-1-carboxylic acid (2,6-difluoro-phenyl)-amide;

4-[4-(6-Acryloylamino-quinazolin-4-ylamino)-2-methyl-phenoxy]-piperidine-1-carboxylic acid (2,6-difluoro-phenyl)-amide;

4-[2-Methyl-4-(6-morpholin-4-yl-quinazolin-4-ylamino)-phenoxy]-piperidine-1-carboxylic acid (2,6-difluoro-phenyl)-amide;

4-[2-Chloro-4-(6-dimethylamino-quinazolin-4-ylamino)-phenoxy]-piperidine-1-carboxylic acid (2,6-difluoro-phenyl)-amide;

4-[2-Chloro-4-(6-{5-[(2-methanesulfonyl-ethylamino)-methyl]-furan-2-yl}-quinazolin-4-ylamino)-phenoxy]-piperidine-1-carboxylic acid (2,6-difluoro-phenyl)-amide;

4-[4-(6-Acryloylamino-quinazolin-4-ylamino)-2-chloro-phenoxy]-piperidine-1-carboxylic acid (2,6-difluoro-phenyl)-amide;

4-[2-Chloro-4-(6-morpholin-4-yl-quinazolin-4-ylamino)-phenoxy]-piperidine-1-carboxylic acid (2,6-difluoro-phenyl)-amide;

N6,N6-Dimethyl-N4-[3-methyl-4-(6-methyl-pyridin-3-yloxy)-phenyl]-pyrido[3,4-d]pyrimidine-4,6-diamine;

6-{5-[(2-Methanesulfonyl-ethylamino)-methyl]-furan-2-yl}-pyrido[3,4-d]pyrimidin-4-yl)-[3-methyl-4-(6-methyl-pyridin-3-yloxy)-phenyl]-amine;

N-{4-[3-Methyl-4-(6-methyl-pyridin-3-yloxy)-phenylamino]-pyrido[3,4-d]pyrimidin-6-yl}-acrylamide;

[3-Methyl-4-(6-methyl-pyridin-3-yloxy)-phenyl]-(6-morpholin-4-yl-pyrido[3,4-d]pyrimidin-4-yl)-amine;

N4-[4-(3-Fluoro-phenoxy)-3-methoxy-phenyl]-N6,N6-dimethyl-pyrido[3,4-d]pyrimidine-4,6-diamine;

4-(3-Fluoro-phenoxy)-3-methoxy-phenyl]-(6-{5-[(2-methanesulfonyl-ethylamino)-methyl]-furan-2-yl}-pyrido[3,4-d]pyrimidin-4-yl)-amine;

N-{4-[4-(3-Fluoro-phenoxy)-3-methoxy-phenylamino]-pyrido[3,4-d]pyrimidin-6-yl}-acrylamide;

[4-(3-Fluoro-phenoxy)-3-methoxy-phenyl]-(6-morpholin-4-yl-pyrido[3,4-d]pyrimidin-4-yl)-amine;

4-[4-(6-Acryloylamino-pyrido[3,4-d]pyrimidin-4-ylamino)-2-methyl-phenoxy]-N-(2,2-dimethyl-propyl)-benzamide;

N-tert-Butyl-3-[4-(6-{5-[(2-methanesulfonyl-ethylamino)-methyl]-furan-2-yl}-pyrido[3,4-d]pyrimidin-4-ylamino)-2-methyl-phenoxy]-benzamide;

3-[4-(6-Acryloylamino-pyrido[3,4-d]pyrimidin-4-ylamino)-2-methyl-phenoxy]-N-tert-butyl-benzamide;

Cyclobutyl-{4-[4-(6-{5-[(2-methanesulfonyl-ethylamino)-methyl]-furan-2-yl}-pyrido[3,4-d]pyrimidin-4-ylamino)-2-methyl-phenoxy]-piperidin-1-yl}-methanone;

N-{4-[4-(1-Cyclobutanecarbonyl-piperidin-4-yloxy)-3-methyl-phenylamino]-pyrido[3,4-d]pyrimidin-6-yl}-acrylamide;

4-[4-(6-{5-[(2-Methanesulfonyl-ethylamino)-methyl]-furan-2-yl}-pyrido[3,4-d]pyrimidin-4-ylamino)-2-methyl-phenoxy]-piperidine-1-carboxylic acid (2,6-difluoro-phenyl)-amide;

4-[4-(6-Acryloylamino-pyrido[3,4-d]pyrimidin-4-ylamino)-2-methyl-phenoxy]-piperidine-1-carboxylic acid (2,6-difluoro-phenyl)-amide;

4-[2-Chloro-4-(6-{5-[(2-methanesulfonyl-ethylamino)-methyl]-furan-2-yl}-pyrido[3,4-d]pyrimidin-4-ylamino)-phenoxy]-piperidine-1-carboxylic acid (2,6-difluoro-phenyl)-amide;

4-[4-(6-Acryloylamino-pyrido[3,4-d]pyrimidin-4-ylamino)-2-chloro-phenoxy]-piperidine-1-carboxylic acid (2,6-difluoro-phenyl)-amide;

6-Dimethylamino-4-[3-methyl-4-(6-methyl-pyridin-3-yloxy)-phenylamino]-quinoline-3-carbonitrile;

6-{5-[(2-Methanesulfonyl-ethylamino)-methyl]-furan-2-yl}-4-[3-methyl-4-(6-methyl-pyridin-3-yloxy)-phenylamino]-quinoline-3-carbonitrile;

N-{3-Cyano-4-[3-methyl-4-(6-methyl-pyridin-3-yloxy)-phenylamino]-quinolin-6-yl}-acrylamide;

4-[3-Methyl-4-(6-methyl-pyridin-3-yloxy)-phenylamino]-6-morpholin-4-yl-quinoline-3-carbonitrile;

6-Dimethylamino-4-[4-(3-fluoro-phenoxy)-3-methoxy-phenylamino]-quinoline-3-carbonitrile;

4-[4-(3-Fluoro-phenoxy)-3-methoxy-phenylamino]-6-{5-[(2-methanesulfonyl-ethylamino)-methyl]-furan-2-yl}-quinoline-3-carbonitrile N-{3-Cyano-4-[4-(3-fluoro-phenoxy)-3-methoxy-phenylamino]-quinolin-6-yl}-acrylamide;

4-[4-(3-Fluoro-phenoxy)-3-methoxy-phenylamino]-6-morpholin-4-yl-quinoline-3-carbonitrile;

4-[4-(3-Cyano-6-dimethylamino-quinolin-4-ylamino)-2-methyl-phenoxy]-N-(2,2-dimethyl-propyl)-benzamide;

4-[4-(3-Cyano-6-{5-[(2-methanesulfonyl-ethylamino)-methyl]-furan-2-yl}-quinolin-4-ylamino)-2-methyl-phenoxy]-N-(2,2-dimethyl-propyl)-benzamide;

4-[4-(6-Acryloylamino-3-cyano-quinolin-4-ylamino)-2-methyl-phenoxy]-N-(2,2-dimethyl-propyl)-benzamide;

4-[4-(3-Cyano-6-morpholin-4-yl-quinolin-4-ylamino)-2-methyl-phenoxy]-N-(2,2-dimethyl-propyl)-benzamide;

N-tert-Butyl-3-[4-(3-cyano-6-dimethylamino-quinolin-4-ylamino)-2-methyl-phenoxy]-benzamide;

N-tert-Butyl-3-[4-(3-cyano-6-{5-[(2-methanesulfonyl-ethylamino)-methyl]-furan-2-y}-quinolin-4-ylamino)-2-methyl-phenoxy]-benzamide;

3-[4-(6-Acryloylamino-3-cyano-quinolin-4-ylamino)-2-methyl-phenoxy]-N-tert-butyl-benzamide;

N-tert-Butyl-3-[4-(3-cyano-6-morpholin-4-yl-quinolin-4-ylamino)-2-methyl-phenoxy]-benzamide;

4-[4-(1-Cyclobutanecarbonyl-piperidin-4-yloxy)-3-methyl-phenylamino]-6-dimethylamino-quinoline-3-carbonitrile;

4-[4-(1-Cyclobutanecarbonyl-piperidin-4-yloxy)-3-methyl-phenylamino]-6-{5-[(2-methanesulfonyl-ethylamino)-methyl]-furan-2-yl}-quinoline-3-carbonitrile;

N-{3-Cyano-4-[4-(1-cyclobutanecarbonyl-piperidin-4-yloxy)-3-methyl-phenylamino]-quinolin-6-yl}-acrylamide;

4-[4-(1-Cyclobutanecarbonyl-piperidin-4-yloxy)-3-methyl-phenylamino]-6-morpholin-4-yl-quinoline-3-carbonitrile;

4-[4-(3-Cyano-6-dimethylamino-quinolin-4-ylamino)-2-methyl-phenoxy]-piperidine-1-carboxylic acid (2,6-difluoro-phenyl)-amide;

4-[4-(3-Cyano-6-{5-[(2-methanesulfonyl-ethylamino)-methyl]-furan-2-yl}-quinolin-4-ylamino)-2-methyl-phenoxy]-piperidine-1-carboxylic acid (2,6-difluoro-phenyl)-amide;

4-[4-(6-Acryloylamino-3-cyano-quinolin-4-ylamino)-2-methyl-phenoxy]-piperidine-1-carboxylic acid (2,6-difluoro-phenyl)-amide;

4-[4-(3-Cyano-6-morpholin-4-yl-quinolin-4-ylamino)-2-methyl-phenoxy]-piperidine-1-carboxylic acid (2,6-difluoro-phenyl)-amide;

4-[2-Chloro-4-(3-cyano-6-dimethylamino-quinolin-4-ylamino)-phenoxy]-piperidine-1-carboxylic acid (2,6-difluoro-phenyl)-amide;

4-[2-Chloro-4-(3-cyano-6-{5-[(2-methanesulfonyl-ethylamino)-methyl]-furan-2-yl}-quinolin-4-ylamino)-phenoxy]-piperidine-1-carboxylic acid (2,6-difluoro-phenyl)-amide;

4-[4-(6-Acryloylamino-3-cyano-quinolin-4-ylamino)-2-chloro-phenoxy]-piperidine-1-carboxylic acid (2,6-difluoro-phenyl)-amide;

4-[2-Chloro-4-(3-cyano-6-morpholin-4-yl-quinolin-4-ylamino)-phenoxy]-piperidine-1-carboxylic acid (2,6-difluoro-phenyl)-amide;

(6,7-Dimethoxy-quinazolin-4-yl)-[3-methyl-4-(6-methyl-pyridin-3-yloxy)-phenyl]-amine;

(6,7-Dimethoxy-quinazolin-4-yl)-[4-(3-fluoro-phenoxy)-3-methoxy-phenyl]-amine;

4-[2-Chloro-4-(6,7-dimethoxy-quinazolin-4-ylamino)-phenoxy]-piperidine-1-carboxylic acid (2,6-difluoro-phenyl)-amide;

[6,7-Bis-(2-methoxy-ethoxy)-quinazolin-4-yl]-[3-methyl-4-(6-methyl-pyridin-3-yloxy)-phenyl]-amine;

[6,7-Bis-(2-methoxy-ethoxy)-quinazolin-4-yl]-[4-(3-fluoro-phenoxy)-3-methoxy-phenyl]-amine;

4-{4-[6,7-Bis-(2-methoxy-ethoxy)-quinazolin-4-ylamino]-2-methyl-phenoxy}-N-(2,2-dimethyl-propyl)-benzamide;

3-{4-[6,7-Bis-(2-methoxy-ethoxy)-quinazolin-4-ylamino]-2-methyl-phenoxy}-N-tert-butyl-benzamide;

(4-{4-[6,7-Bis-(2-methoxy-ethoxy)-quinazolin-4-ylamino]-2-methyl-phenoxy}-piperidin-1-yl)-cyclobutyl-methanone;

4-{4-[6,7-Bis-(2-methoxy-ethoxy)-quinazolin-4-ylamino]-2-methyl-phenoxy}-piperidine-1-carboxylic acid (2,6-difluoro-phenyl)-amide;

4-{4-[6,7-Bis-(2-methoxy-ethoxy)-quinazolin-4-ylamino]-2-chloro-phenoxy}-piperidine-1-carboxylic acid (2,6-difluoro-phenyl)-amide;

[7-Methoxy-6-(3-morpholin-4-yl-propoxy)-quinazolin-4-yl]-[3-methyl-4-(6-methyl-pyridin-3-yloxy)-phenyl]-amine;

[4-(3-Fluoro-phenoxy)-3-methoxy-phenyl]-[7-methoxy-6-(3-morpholin-4-yl-propoxy)-quinazolin-4-yl]-amine;

N-(2,2-Dimethyl-propyl)-4-{4-[7-methoxy-6-(3-morpholin-4-yl-propoxy)-quinazolin-4-ylamino]-2-methyl-phenoxy}-benzamide;

N-tert-Butyl-3-{4-[7-methoxy-6-(3-morpholin-4-yl-propoxy)-quinazolin-4-ylamino]-2-methyl-phenoxy}-benzamide;

Cyclobutyl-(4-{4-[7-methoxy-6-(3-morpholin-4-yl-propoxy)-quinazolin-4-ylamino]-2-methyl-phenoxy}-piperidin-1-yl)-methanone;

4-{4-[7-Methoxy-6-(3-morpholin-4-yl-propoxy)-quinazolin-4-ylamino]-2-methyl-phenoxy}-piperidine-1-carboxylic acid (2,6-difluoro-phenyl)-amide;

4-{2-Chloro-4-[7-methoxy-6-(3-morpholin-4-yl-propoxy)-quinazolin-4-ylamino]-phenoxy}-piperidine-1-carboxylic acid (2,6-difluoro-phenyl)-amide;

(6-Methoxy-pyrido[3,4-d]pyrimidin-4-yl)-[3-methyl-4-(6-methyl-pyridin-3-yloxy)-phenyl]-amine;

[4-(3-Fluoro-phenoxy)-3-methoxy-phenyl]-(6-methoxy-pyrido[3,4-d]pyrimidin-4-yl)-amine;

N-(2,2-Dimethyl-propyl)-4-[4-(6-methoxy-pyrido[3,4-d]pyrimidin-4-ylamino)-2-methyl-phenoxy]-benzamide;

[6-(2-Methoxy-ethoxy)-pyrido[3,4-d]pyrimidin-4-yl]-[3-methyl-4-(6-methyl-pyridin-3-yloxy)-phenyl]-amine;

[4-(3-Fluoro-phenoxy)-3-methoxy-phenyl]-[6-(2-methoxy-ethoxy)-pyrido[3,4-d]pyrimidin-4-yl]-amine;

N-(2,2-Dimethyl-propyl)-4-{4-[6-(2-methoxy-ethoxy)-pyrido[3,4-d]pyrimidin-4-ylamino]-2-methyl-phenoxy}-benzamide;

N-tert-Butyl-3-{4-[6-(2-methoxy-ethoxy)-pyrido[3,4-d]pyrimidin-4-ylamino]-2-methyl-phenoxy}-benzamide;

Cyclobutyl-(4-{4-[6-(2-methoxy-ethoxy)-pyrido[3,4-d]pyrimidin-4-ylamino]-2-methyl-phenoxy}-piperidin-1-yl)-methanone;

4-{4-[6-(2-Methoxy-ethoxy)-pyrido[3,4-d]pyrimidin-4-ylamino]-2-methyl-phenoxy}-piperidine-1-carboxylic acid (2,6-difluoro-phenyl)-amide;

[3-Methyl-4-(6-methyl-pyridin-3-yloxy)-phenyl]-[6-(3-morpholin-4-yl-propoxy)-pyrido[3,4-d]pyrimidin-4-yl]-amine;

[4-(3-Fluoro-phenoxy)-3-methoxy-phenyl]-[6-(3-morpholin-4-yl-propoxy)-pyrido[3,4-d]pyrimidin-4-yl]-amine;

N-(2,2-Dimethyl-propyl)-4-{2-methyl-4-[6-(3-morpholin-4-yl-propoxy)-pyrido[3,4-d]pyrimidin-4-ylamino]-phenoxy}-benzamide;

N-tert-Butyl-3-{2-methyl-4-[6-(3-morpholin-4-yl-propoxy)-pyrido[3,4-d]pyrimidin-4-ylamino]-phenoxy}-benzamide;

Cyclobutyl-(4-{2-methyl-4-[6-(3-morpholin-4-yl-propoxy)-pyrido[3,4-d]pyrimidin-4-ylamino]-phenoxy}-piperidin-1-yl)-methanone;

4-{2-Methyl-4-[6-(3-morpholin-4-yl-propoxy)-pyrido[3,4-d]pyrimidin-4-ylamino]-phenoxy}-piperidine-1-carboxylic acid (2,6-difluoro-phenyl)-amide;

4-{2-Chloro-4-[6-(3-morpholin-4-yl-propoxy)-pyrido[3,4-d]pyrimidin-4-ylamino]-phenoxy}-piperidine-1-carboxylic acid (2,6-difluoro-phenyl)-amide;

6,7-Dimethoxy-4-[3-methyl-4-(6-methyl-pyridin-3-yloxy)-phenylamino]-quinoline-3-carbonitrile;

4-[4-(3-Fluoro-phenoxy)-3-methoxy-phenylamino]-6,7-dimethoxy-quinoline-3-carbonitrile;

4-[4-(3-Cyano-6,7-dimethoxy-quinolin-4-ylamino)-2-methyl-phenoxy]-N-(2,2-dimethyl-propyl)-benzamide;

N-tert-Butyl-3-[4-(3-cyano-6,7-dimethoxy-quinolin-4-ylamino)-2-methyl-phenoxy]-benzamide;

4-[4-(1-Cyclobutanecarbonyl-piperidin-4-yloxy)-3-methyl-phenylamino]-6,7-dimethoxy-quinoline-3-carbonitrile;

4-[4-(3-Cyano-6,7-dimethoxy-quinolin-4-ylamino)-2-methyl-phenoxy]-piperidine-1-carboxylic acid (2,6-difluoro-phenyl)-amide;

4-[2-Chloro-4-(3-cyano-6,7-dimethoxy-quinolin-4-ylamino)-phenoxy]-piperidine-1-carboxylic acid (2,6-difluoro-phenyl)-amide;

6,7-Bis-(2-methoxy-ethoxy)-4-[3-methyl-4-(6-methyl-pyridin-3-yloxy)-phenylamino]-quinoline-3-carbonitrile;

4-[4-(3-Fluoro-phenoxy)-3-methoxy-phenylamino]-6,7-bis-(2-methoxy-ethoxy)-quinoline-3-carbonitrile;

4-{4-[3-Cyano-6,7-bis-(2-methoxy-ethoxy)-quinolin-4-ylamino]-2-methyl-phenoxy}-N-(2,2-dimethyl-propyl)-benzamide;

N-tert-Butyl-3-{4-[3-cyano-6,7-bis-(2-methoxy-ethoxy)-quinolin-4-ylamino]-2-methyl-phenoxy}-benzamide;

4-[4-(1-Cyclobutanecarbonyl-piperidin-4-yloxy)-3-methyl-phenylamino]-6,7-bis-(2-methoxy-ethoxy)-quinoline-3-carbonitrile;

4-{4-[3-Cyano-6,7-bis-(2-methoxy-ethoxy)-quinolin-4-ylamino]-2-methyl-phenoxy}-piperidine-1-carboxylic acid (2,6-difluoro-phenyl)-amide;

4-{2-Chloro-4-[3-cyano-6,7-bis-(2-methoxy-ethoxy)-quinolin-4-ylamino]-phenoxy}-piperidine-1-carboxylic acid (2,6-difluoro-phenyl)-amide;

7-Methoxy-4-[3-methyl-4-(6-methyl-pyridin-3-yloxy)-phenylamino]-6-(3-morpholin-4-yl-propoxy)-quinoline-3-carbonitrile;

4-[4-(3-Fluoro-phenoxy)-3-methoxy-phenylamino]-7-methoxy-6-(3-morpholin-4-yl-propoxy)-quinoline-3-carbonitrile;

4-{4-[3-Cyano-7-methoxy-6-(3-morpholin-4-yl-propoxy)-quinolin-4-ylamino]-2-methyl-phenoxy}-N-(2,2-dimethyl-propyl)-benzamide;

N-tert-Butyl-3-{4-[3-cyano-7-methoxy-6-(3-morpholin-4-yl-propoxy)-quinolin-4-ylamino]-2-methyl-phenoxy}-benzamide;

4-[4-(1-Cyclobutanecarbonyl-piperidin-4-yloxy)-3-methyl-phenylamino]-7-methoxy-6-(3-morpholin-4-yl-propoxy)-quinoline-3-carbonitrile;

4-{4-[3-Cyano-7-methoxy-6-(3-morpholin-4-yl-propoxy)-quinolin-4-ylamino]-2-methyl-phenoxy}-piperidine-1-carboxylic acid (2,6-difluoro-phenyl)-amide;

4-{2-Chloro-4-[3-cyano-7-methoxy-6-(3-morpholin-4-yl-propoxy)-quinolin-4-ylamino]-phenoxy}-piperidine-1-carboxylic acid (2,6-difluoro-phenyl)-amide and the pharmaceutically acceptable salts, prodrugs and solvates of the foregoing compounds.

In another particularly preferred embodiment of the invention, a compound of the formula 1 selected from the group consisting of:

4-[2-Methyl-4-(6-morpholin-4-yl-pyrido[3,4-d]pyrimidin-4-ylamino)-phenoxy]-piperidine-1-carboxylic acid (2,6-difluoro-phenyl)-amide;

4-[4-(6-Dimethylamino-pyrido[3,4-d]pyrimidin-4-ylamino)-2-methyl-phenoxy]-piperidine-1-carboxylic acid (2,6-difluoro-phenyl)-amide;

N-(2,2-Dimethyl-propyl)-4-[2-methyl-4-(6-morpholin-4-yl-pyrido[3,4-d]pyrimidin-4-ylamino)-phenoxy]-benzamide;

4-[4-(6,7-Dimethoxy-quinazolin-4-ylamino)-2-methyl-phenoxy]-piperidine-1-carboxylic acid (2,6-difluoro-phenyl)-amide;

Cyclopentyl-{4-[2-methyl-4-(6-morpholin-4-yl-pyrido[3,4-d]pyrimidin-4-ylamino)-phenoxy]-piperidin-1-yl}-methanone;

N-tert-Butyl-3-[2-methyl-4-(6-morpholin-4-yl-pyrido[3,4-d]pyrimidin-4-ylamino)-phenoxy]-benzamide;

N-(2,2-Dimethyl-propyl)-3-[2-methyl-4-(6-morpholin-4-yl-pyrido[3,4-d]pyrimidin-4-ylamino)-phenoxy]-benzamide;

3-[4-(6-Dimethylamino-pyrido[3,4-d]pyrimidin-4-ylamino)-2-methyl-phenoxy]-N-(2,2-dimethyl-propyl)-benzamide;

4-[4-(6-Methoxy-quinazolin-4-ylamino)-2-methyl-phenoxy]-piperidine-1-carboxylic acid cyclopentylamide;

4-[2-Methyl-4-(6-morpholin-4-yl-pyrido[3,4-d]pyrimidin-4-ylamino)-phenoxy]-piperidine-1-carboxylic acid (4-methoxy-phenyl)-amide;

4-[4-(6-Dimethylamino-pyrido[3,4-d]pyrimidin-4-ylamino)-2-methyl-phenoxy]-piperidine-1-carboxylic acid cyclopentylamide;

4-[4-(6-Dimethylamino-pyrido[3,4-d]pyrimidin-4-ylamino)-2-methyl-phenoxy]-piperidine-1-carboxylic acid (2,5-difluoro-phenyl)-amide;

4-[4-(6-Dimethylamino-pyrido[3,4-d]pyrimidin-4-ylamino)-2-methyl-phenoxy]-piperidine-1-carboxylic acid p-tolylamide;

4-[4-(6-Dimethylamino-pyrido[3,4-d]pyrimidin-4-ylamino)-2-methyl-phenoxy]-N-(2,2-dimethyl-propyl)-benzamide; N-(2,2-Dimethyl-propyl)-4-[2-methyl-4-(6-pyrrolidin-1-yl-pyrido[3,4-d]pyrimidin-4-ylamino)-phenoxy]-benzamide; and, Cyclopentyl-{4-[2-methyl-4-(6-methylamino-pyrido[3,4-d]pyrimidin-4-ylamino)-phenoxy]-piperidin-1-yl}-methanone and the pharmaceutically acceptable salts, prodrugs and solvates of the foregoing compounds.

In another embodiment of the invention, a method for the treatment of abnormal cell growth in a mammal comprising administering to said mammal an amount of a compound of formula 1 that is effective in treating abnormal cell growth.

In another preferred embodiment of the invention, a method wherein said abnormal cell growth is cancer.

In another preferred embodiment of the invention, a method wherein said cancer is selected from lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers.

In another embodiment of the invention, a method for the treatment of abnormal cell growth in a mammal which comprises administering to said mammal an amount of a compound of claim 1 that is effective in treating abnormal cell growth in combination with an anti-tumor agent selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

In another embodiment of the invention, a pharmaceutical composition for the treatment of abnormal cell growth in a mammal comprising an amount of a compound of formula 1 that is effective in treating abnormal cell growth, and a pharmaceutically acceptable carrier.

This invention also relates to a method for the treatment of abnormal cell growth in a mammal, including a human, comprising administering to said mammal an amount of a compound of the formula 1, as defined above, or a pharmaceutically acceptable salt, solvate or prodrug thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a compound of formula 1, or a pharmaceutically acceptable salt, solvate or prodrug thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

This invention also relates to a pharmaceutical composition for the treatment of abnormal cell growth in a mammal, including a human, comprising an amount of a compound of the formula 1, as defined above, or a pharmaceutically acceptable salt, solvate or prodrug thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

The invention also relates to a pharmaceutical composition for the treatment of abnormal cell growth in a mammal, including a human, which comprises an amount of a compound of formula 1, as defined above, or a pharmaceutically acceptable salt, solvate or prodrug thereof, that is effective in treating abnormal cell growth in combination with a pharmaceutically acceptable carrier and an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

This invention also relates to a method for the treatment of a disorder associated with angiogenesis in a mammal, including a human, comprising administering to said mammal an amount of a compound of the formula 1, as defined above, or a pharmaceutically acceptable salt, solvate or prodrug thereof, that is effective in treating said disorder. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi, Yersinia* spp., *Bordetella pertussis*, and group A *Streptococcus*.

This invention also relates to a method of (and to a pharmaceutical composition for) treating abnormal cell growth in a mammal which comprise an amount of a compound of formula 1, or a pharmaceutically acceptable salt, solvate or prodrug thereof, and an amount of one or more substances selected from anti-angiogenesis agents, signal transduction inhibitors, and antiproliferative agents, which amounts are together effective in treating said abnormal cell growth.

A compound of formula 1 may also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present invention include those described in U.S. Provisional Application 60/113,647 (filed Dec. 23, 1998), which is herein incorporated by reference in its entirety.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

Certain functional groups contained within the compounds of the present invention can be substituted for bioisosteric groups, that is, groups that have similar spatial or electronic requirements to the parent group, but exhibit differing or improved physicochemical or other properties. Suitable examples are well known to those of skill in the art, and include, but are not limited to moieties described in Patini et al., Chem. Rev, 1996, 96, 3147-3176 and references cited therein.

The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. The compounds of formula 1 may also exist as tautomers. This invention relates to the use of all such tautomers and mixtures thereof.

The subject invention also includes isotopically-labelled compounds, and the pharmaceutically acceptable salts, solvates and prodrugs thereof, which are identical to those recited in formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$, and $^{38}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of formula 1 of this invention and prodrugs thereof can generally be prepared by carrying out the procedures disclosed in the Schemes and/or in the Examples and Preparations below, by substituting a readily available isotopically labeled reagent for a non-isotopically labeled reagent.

This invention also encompasses pharmaceutical compositions containing and methods of treating bacterial infections through administering prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of formula 1 in the methods and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in combination with the compounds of the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R,3R)1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

3-[4-(4-chloro-phenoxy)-benzenesulfonylamino]-tetrahydro-pyran-3-carboxylic acid hydroxyamide;

(2R,3R)1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and 3-[4-(4-fluoro-phenoxy)-benzenesulfonylamino]-tetrahydro-furan-3-carboxylic acid hydroxyamide;

and pharmaceutically acceptable salts, solvates and prodrugs of said compounds.

The compounds of formula 1, and the pharmaceutically acceptable salts, solvates and prodrugs thereof, can also be used in combination with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

VEGF inhibitors, for example SU-5416 and SU-6668 (Sugen Inc. of South San Francisco, Calif., USA), can also be combined with a compound of formula 1. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with a compound of formula 1. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety.

Other antiproliferative agents that may be used with the compounds of the present invention include inhibitors of the enzyme farnesyl protein transferase and inhibitors of the receptor tyrosine kinase PDGFr, including the compounds disclosed and claimed in the following U.S. patent application Ser. Nos. 09/221,946 (filed Dec. 28, 1998); 09/454,058 (filed Dec. 2, 1999); 09/501,163 (filed Feb. 9, 2000); 09/539,930 (filed Mar. 31, 2000); 09/202,796 (filed May 22, 1997); 09/384,339 (filed Aug. 26, 1999); and 09/383,755 (filed Aug. 26, 1999); and the compounds disclosed and claimed in the following U.S. provisional patent applications: 60/168,207 (filed Nov. 30, 1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety.

DETAILED DESCRIPTION OF THE INVENTION

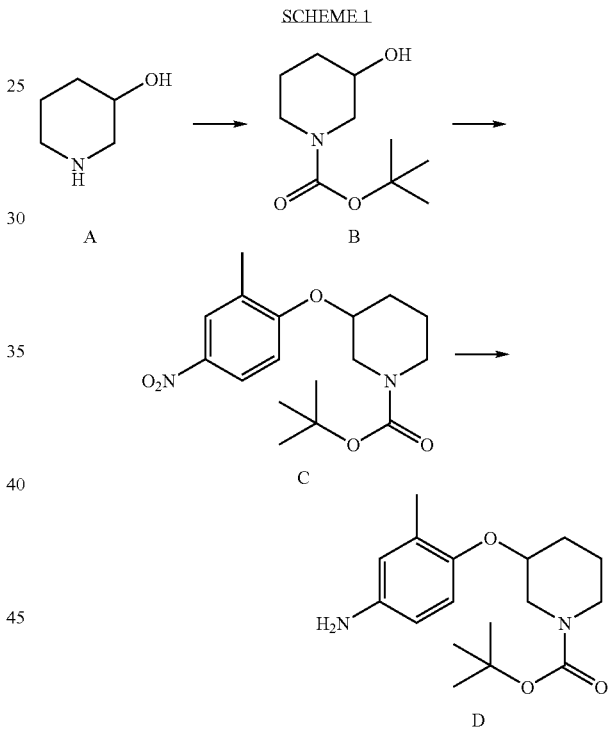

SCHEME 1

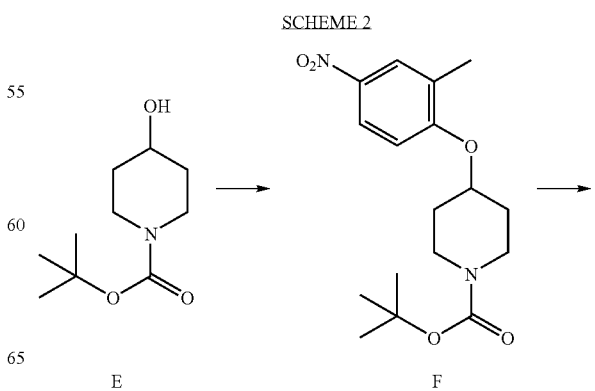

SCHEME 2

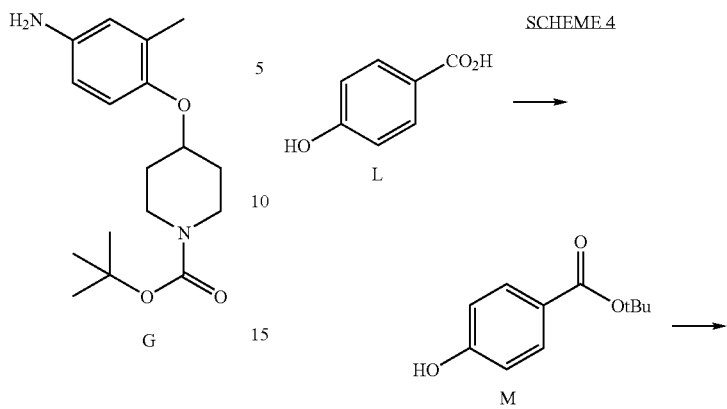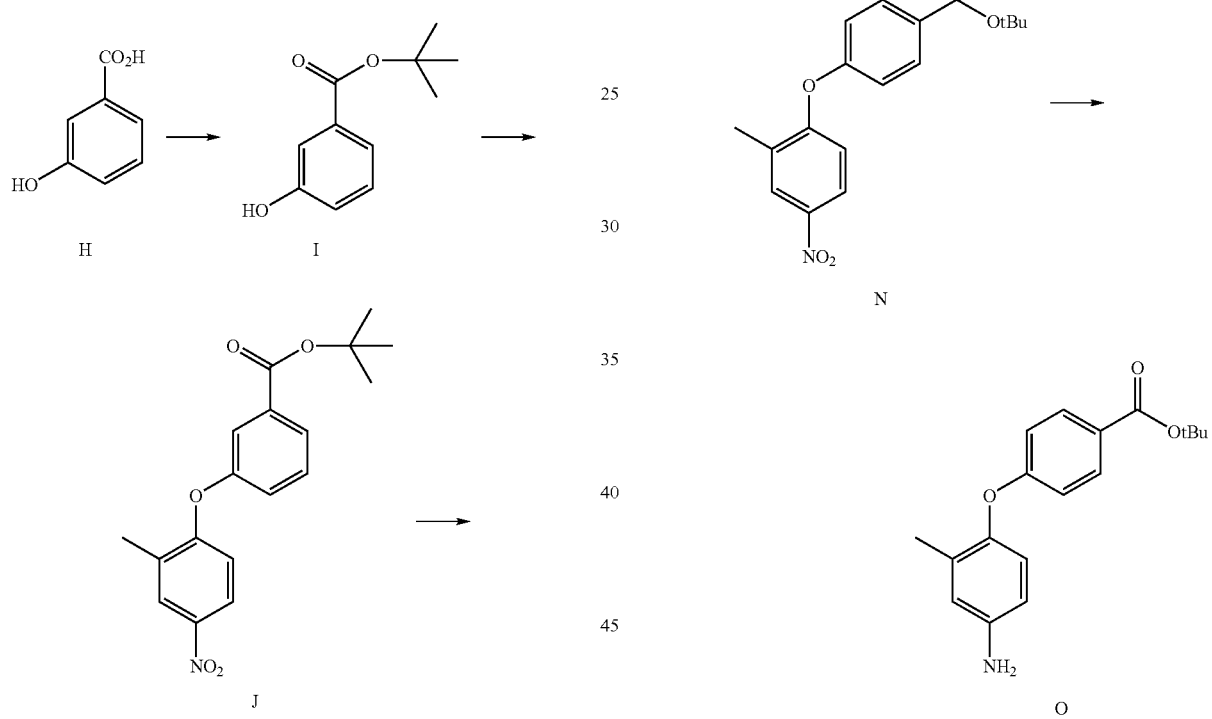

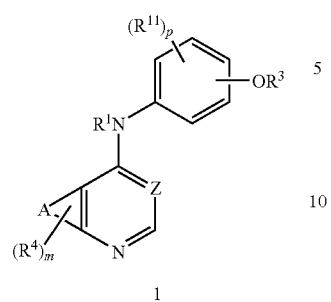
1
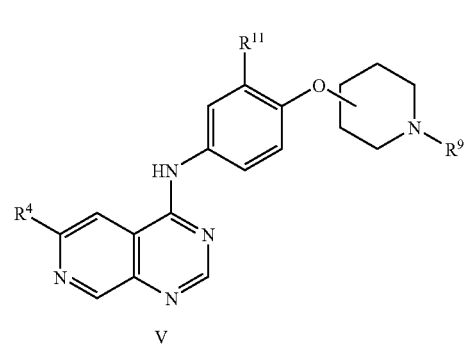
V
SCHEME 6
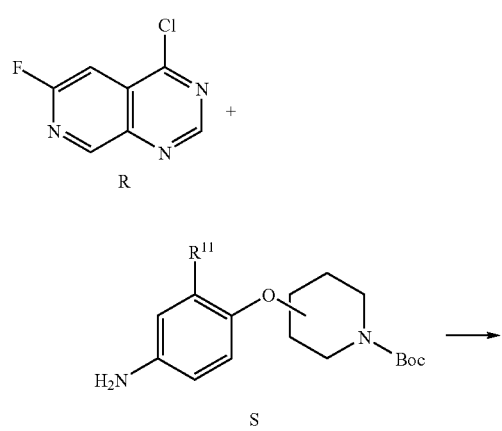
SCHEME 7
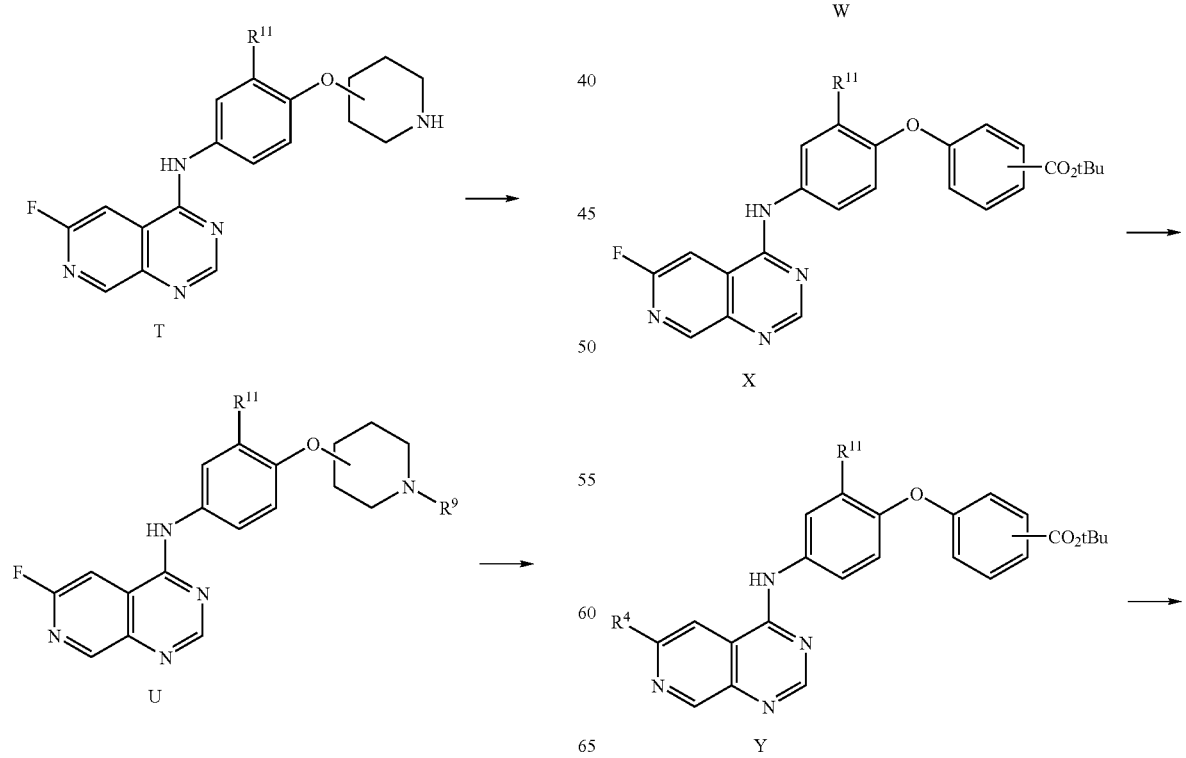

-continued

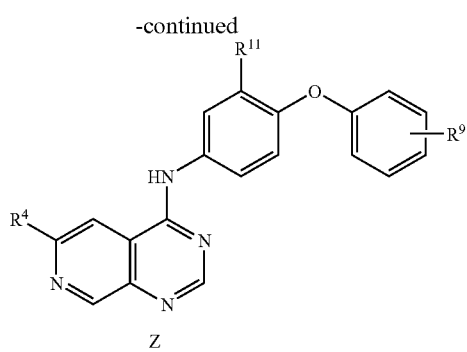

General synthetic methods which may be referred to for preparing the compounds of the present invention are provided in U.S. Pat. No. 5,747,498 (issued May 5, 1998), U.S. patent application Ser. No. 08/953,078 (filed Oct. 17, 1997), WO 98/02434 (published Jan. 22, 1998), WO 98/02438 (published Jan. 22, 1998), WO 96/40142 (published Dec. 19, 1996), WO 96/09294 (published Mar. 6, 1996), WO 97/03069 (published Jan. 30, 1997), WO 95/19774 (published Jul. 27, 1995) and WO 97/13771 (published Apr. 17, 1997). Additional procedures are referred to in U.S. patent application Ser. Nos. 09/488,350 (filed Jan. 20, 2000), 09/488,378 (filed Jan. 20, 2000), WO 99/35132, WO 98/02434, WO 97/30034, WO 96/15118, WO 01/68186, WO 97/38983, WO 02/066445 and WO 00/44728. The foregoing patents and patent applications are incorporated herein by reference in their entirety. Certain starting materials may be prepared according to methods familiar to those skilled in the art and certain synthetic modifications may be done according to methods familiar to those skilled in the art.

Starting materials, the synthesis of which is not specifically described above, are either commercially available or can be prepared using methods well known to those of skill in the art.

In each of the reactions discussed or illustrated in the Schemes above, pressure is not critical unless otherwise indicated. Pressures from about 0.5 atmospheres to about 5 atmospheres are generally acceptable, and ambient pressure, i.e., about 1 atmosphere, is preferred as a matter of convenience.

With reference to Scheme 1 above, the compound of formula B may be prepared from the compound of formula A in a suitably polar solvent, preferably ethanol, through the slow addition of Di-tert-butyldicarbonate at low temperature, preferably −10° C. The temperature is then raised to ambient temperature, preferably 20° C. and stirred for 12-48 hours, preferably 16 hours. The compound of formula C may be prepared from the compound of formula B through the slow addition of a strong base, preferably sodium hydride in a suitably polar non-protic solvent, preferably N,N-dimethylformamide, at low temperature, preferably 0-15° C. After a period of 30 minutes, 2-fluoro-5-nitrotoluene is added slowly and the reaction is stirred for 12-48 hours, preferably 16 hours. The compound of formula D may be prepared from the compound of formula C in a suitably polar solvent, preferably ethanol, through the addition of palladium hydroxide under an atmosphere of hydrogen with a pressure of 1-90 PSI, preferably 45 PSI for a period of 12-48 hours, preferably 16 hours.

With reference to Scheme 2 above, the compound of formula F may be prepared from the compound of formula E through the slow addition of a strong base, preferably sodium hydride in a suitably polar non-protic solvent, preferably N,N-dimethylformamide, at low temperature, preferably 0-15° C. After a period of 30 minutes, 2-fluoro-5-nitrotoluene is added slowly and the reaction is stirred for 1-24 hours, preferably 3 hours. The compound of formula G may be prepared from the compound of formula F in a suitably polar solvent, preferably ethanol, through the addition of palladium hydroxide under an atmosphere of hydrogen with a pressure of 1-90 PSI, preferably 45 PSI for a period of 12-48 hours, preferably 16 hours.

With reference to Scheme 3 above, the compound of formula I may be prepared from the compound of formula H in a polar non-protic solvent, preferably p-dioxane with a suitably strong acid, preferably sulfuric acid, through the addition of isobutene at a low temperature, preferably 0° C. After 2 hours, the temperature is raised to ambient temperature, preferably 20° C. and stirred for 12-48 hours, preferably 16 hours. The compound of formula J may be prepared from the compound of formula I through the slow addition of a strong base, preferably sodium hydride in a suitably polar non-protic solvent, preferably N,N-dimethylformamide, at low temperature, preferably 0-15° C. After a period of 30 minutes, 2-fluoro-5-nitrotoluene is added slowly and the reaction is stirred for 24-64 hours, preferably 50 hours at a temperature between 15° C. and 60° C. The compound of formula K may be prepared from the compound of formula J in a suitably polar solvent, preferably ethanol, through the addition of palladium hydroxide under an atmosphere of hydrogen with a pressure of 1-90 PSI, preferably 45 PSI for a period of 12-48 hours, preferably 16 hours.

With reference to Scheme 4 above, the compound of formula M may be prepared from the compound of formula L in tert-butanol with N,N-dimethylaminopyridine through the slow addition of 1,3-dicyclohexylcarbodiimide at ambient temperature, preferably 20° C., and allowing the reaction to occur over a time period of 1-24 hours, preferably 3.5 hours. The compound of formula N may be prepared from the compound of formula M through the slow addition of a strong base, preferably sodium hydride in a suitably polar non-protic solvent, preferably N,N-dimethylformamide, at low temperature, preferably 0-15° C. After a period of 30 minutes, 2-fluoro-5-nitrotoluene is added slowly and the reaction is heated the reaction is stirred for 12-48 hours, preferably 16 hours at ambient temperature, preferably 20° C. The compound of formula O may be prepared from the compound of formula N in a suitably polar solvent, preferably ethanol, through the addition of palladium hydroxide under an atmosphere of hydrogen with a pressure of 1-90 PSI, preferably 45 PSI for a period of 12-48 hours, preferably 16 hours.

With reference to Scheme 5 above, the compound of formula 1 may be prepared from the compound of formula P through the addition of an aniline such as Q. The reaction is carried out in a suitably polar solvent, preferably a mixture of tert-butanol and dichloroethane at a temperature between 0 and 110° C. for a period of 1-48 hours. In certain cases a base is also added to the reaction, preferably triethylamine. Any compound of formula 1 can be converted into another compound of formula 1 by standard manipulations to the $R^3$ and $R^4$ group. These methods are known to those skilled in the art and include a) removal of a protecting group by methods outlined in T. W. Greene and P. G. M. Wuts, "Protective Groups in Organic Synthesis", Second Edition, John Wiley and Sons, New York, 1991; b) displacement of a leaving group (halide, mesylate, tosylate, etc) with a primary or secondary amine, thiol or alcohol to form a secondary or tertiary amine, thioether or ether, respectively; c) treatment of phenyl (or substituted phenyl) carbamates with primary of secondary amines to form the corresponding ureas as in Thavonekham, B et. al. Synthesis (1997), 10, p 1189; d) treatment of primary and secondary amines with an isocyanate, acid chloride (or other activated carboxylic acid derivative), alkyl/aryl chloroformate or sulfonyl chloride to provide the corresponding urea, amide, carbamate or sulfonamide; e) reductive amination of a primary or secondary amine using $R^1CH(O)$; and h) treatment of alcohols with an isocyanate, acid chloride (or other activated carboxylic acid derivative), alkyl/aryl chloroformate or sulfonyl chloride to provide the corresponding carbamate, ester, carbonate or sulfonic acid ester. Many examples of the above transformations are also found in the cited patents and applications noted above. Representative examples of $R^4$ and $R^3$ conversions within formula 1 are found in schemes 6 and 7.

With reference to Scheme 6 above, the compound of formula T may be prepared from the compound of formula R through the addition of S in a suitably polar solvent, preferably a mixture of tert-butanol and dichloroethane with the addition of a weak base, preferably triethylamine, at a temperature between 0° C. and 110° C., preferably 90° C., for a period of 1-48 hours, preferably 2 hours. The reaction is then cooled to ambient temperature, preferably 20° C., and treated with hydrogen chloride for a period of 30 minutes to 8 hours, preferably 1 hour. In one preferred embodiment of this invention, the compound of the formula U may be prepared from the compound of formula T through the use of an acid chloride, for example cyclopentyl acid chloride, in a non-polar aprotic solvent, preferably methylene chloride, with a weak base, preferably triethylamine, for a period of 0.5-12 hours, preferably 1 hour. Other derivatives defined by $R^9$ are easily accessible by one skilled in the art. The compound of formula V may be prepared from the compound of formula U in a polar aprotic solvent, preferably dimethylsulfoxide, with an amine, for example pyrrolodine, and a weak base, preferably triethylamine. The reaction is heated to 60-130° C., preferably 120° C., for a period of 6-96 hours, preferably 12 hours.

With reference to Scheme 7 above, the compound of formula X may be prepared from the compound of formula R through the addition of W in a suitably polar solvent, preferably a mixture of tert-butanol and dichloroethane with the addition of a weak base, preferably triethylamine, at a temperature between 0° C. and 110° C., preferably 90° C., for a period of 1-48 hours, preferably 5 hours. The compound of formula Y may be prepared from the compound of formula X in a polar aprotic solvent, preferably dimethylsulfoxide, with an amine, for example pyrrolodine, and a weak base, preferably triethylamine. The reaction is heated to 60-130° C., preferably 120° C., for a period of 6-96 hours, preferably 12 hours. The compound of formula Z may be prepared from the compound of formula Y through the addition of a strong acid, preferably trifluoroacetic acid, in a non-polar solvent, preferably methylene chloride, at ambient temperature, preferably 20° C., and allowing the reaction to stir for 2-24 hours, preferably 12 hours. The intermediate free acid is then isolated and dissolved in a polar aprotic solvent, preferably N,N-dimethylformamide, with a weak base, preferably triethylamine, with a nucleophilic amine, for example tert-butylamine, and a suitable coupling reagent, preferably O-(7-azabenzotriazol-1-yl)-N,N,N',N'-tetramethyluronium hexafluorophosphate. The reaction is then stirred at a temperature between 20-110° C., preferably 60° C., for a period of 6-96 hours, preferably 12 hours.

The compounds of the present invention may have asymmetric carbon atoms. Diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

The compounds of formula 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula 1 that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula 1. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product. Since a single compound of the present invention may include more than one acidic or basic moieties, the compounds of the present invention may include mono, di or tri-salts in a single compound.

The compounds of the present invention are potent inhibitors of the erbB family of oncogenic and protooncogenic protein tyrosine kinases, in particular erbB2, and thus are all adapted to therapeutic use as antiproliferative agents (e.g., anticancer) in mammals, particularly in humans. In particular, the compounds of the present invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the skin (e.g., psoriasis) and benign hyperplasia of the prostate (e.g., BPH). It is, in addition, expected that a compound of the present invention may possess activity against a range of leukemias and lymphoid malignancies.

The compounds of the present invention may also be useful in the treatment of additional disorders in which aberrant expression ligand/receptor interactions or activation or signaling events related to various protein tyrosine kinases, are involved. Such disorders may include those of neuronal, glial, astrocytal, hypothalamic, and other glandular, macrophagal, epithelial, stromal, and blastocoelic nature in which aberrant function, expression, activation or signaling of the erbB tyrosine kinases are involved. In addition, the compounds of the present invention may have therapeutic utility in inflammatory, angiogenic and immunologic disorders involving both identified and as yet unidentified tyrosine kinases that are inhibited by the compounds of the present invention.

The in vitro activity of the compounds of formula 1 may be determined by the following procedure.

The c-erbB2 kinase assay is similar to that described previously in Schrang et. al. Anal. Biochem. 211, 1993, p 233-239. Nunc MaxiSorp 96-well plates are coated by incubation overnight at 37° C. with 100 mL per well of 0.25 mg/mL Poly (Glu, Tyr) 4:1 (PGT) (Sigma Chemical Co., St. Louis, Mo.) in PBS (phosphate buffered saline). Excess PGT is removed by aspiration, and the plate is washed three times with wash buffer (0.1% Tween 20 in PBS). The kinase reaction is performed in 50 mL of 50 mM HEPES (pH 7.5) containing 125 mM sodium chloride, 10 mM magnesium chloride, 0.1 mM sodium orthovanadate, 1 mM ATP, 0.48 mg/mL (24 ng/well) c-erbB2 intracellular domain. The intracellular domain of the erbB2 tyrosine kinase (amino acids 674-1255) is expressed as a GST fusion protein in Baculovirus and purified by binding to and elution from glutathione coated beads. The compound in DMSO (dimethylsulfoxide) is added to give a final DMSO concentration of about 2.5%. Phosphorylation was initiated by addition of ATP (adenosine triphosphate) and proceeded for 6 minutes at room temperature, with constant shaking. The kinase reaction is terminated by aspiration of the reaction mixture and subsequent washing with wash buffer (see above). Phosphorylated PGT is measured by 25 minutes of incubation with 50 mL per well HRP-conjugated PY54 (Oncogene Science Inc. Uniondale, N.Y.) antiphosphotyrosine antibody, diluted to 0.2 mg/mL in blocking buffer (3% BSA and 0.05% Tween 20 in PBS). Antibody is removed by aspiration, and the plate is washed 4 times with wash buffer. The colorimetric signal is developed by addition of TMB Microwell Peroxidase Substrate (Kirkegaard and Perry, Gaithersburg, Md.), 50 mL per well, and stopped by the addition of 0.09 M sulfuric acid, 50 mL per well. Phosphotyrosine is estimated by measurement of absorbance at 450 nm. The signal for controls is typically 0.6-1.2 absorbance units, with essentially no background in wells without the PGT substrate and is proportional to the time of incubation for 10 minutes. Inhibitors were identified by reduction of signal relative to wells without inhibitor and $IC_{50}$ values corresponding to the concentration of compound required for 50% inhibition are determined. The compounds exemplified herein which correspond to formula 1 have IC50 values of <10 μM against erbB2 kinase.

The activity of the compounds of formula 1, in vivo, can be determined by the amount of inhibition of tumor growth by a test compound relative to a control. The tumor growth inhibitory effects of various compounds are measured according to the method of Corbett T. H., et al., "Tumor Induction Relationships in Development of Transplantable Cancers of the Colon in Mice for Chemotherapy Assays, with a Note on Carcinogen Structure", Cancer Res., 35, 2434-2439 (1975) and Corbett T. H., et al., "A Mouse Colon-tumor Model for Experimental Therapy", Cancer Chemother. Rep. (Part 2)", 5, 169-186 (1975), with slight modifications. Tumors are induced in the left flank by subcutaneous (sc) injection of 1-5 million log phase cultured tumor cells (murine FRE-ErbB2 cells or human SK-OV3 ovarian carcinoma cells) suspended in 0.1 ml RPMI 1640 medium. After sufficient time has elapsed for the tumors to become palpable (100-150 mm3 in size/5-6 mm in diameter) the test animals (athymic female mice) are treated with test compound (formulated at a concentration of 10 to 15 mg/ml in 5 Gelucire) by the intraperitoneal (ip) or oral (po) route of administration once or twice daily for 7 to 10 consecutive days. In order to determine an anti-tumor effect, the tumor is measured in millimeters with a Vernier caliper across two diameters and the tumor size (mm3) is calculated using the formula: Tumor size (mm3)= (length×[width]2)/2, according to the methods of Geran, R. I., et al. "Protocols for Screening Chemical Agents and Natural Products Against Animal Tumors and Other Biological Systems", Third Edition, Cancer Chemother. Rep., 3, 1-104 (1972). Results are expressed as percent inhibition, according to the formula: Inhibition (%)=(TuW$_{control}$-TuW$_{test}$)/Tu W$_{control}$×100%. The flank site of tumor implantation provides reproducible dose/response effects for a variety of chemotherapeutic agents, and the method of measurement (tumor diameter) is a reliable method for assessing tumor growth rates.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumor substances, for example those selected from, for example, mitotic inhibitors, for example vinblastine; alkylating agents, for example cisplatin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Materials and Methods

Where preparatory HPLC chromatography is referred to in the preparations and examples below, the general conditions used, unless otherwise indicated, are as follows. The column used is a ZORBAX™ RXC18 column (manufactured by Hewlett Packard) of 150 mm distance and 4.6 mm interior diameter. The samples are run on a Hewlett Packard-1100 system. A gradient solvent method is used running 100 percent ammonium acetate/acetic acid buffer (0.2 M) to 100 percent acetonitrile over 20 minutes. The system then proceeds on a wash cycle with 100 percent acetonitrile for 1.5 minutes and then 100 percent buffer solution for 3 minutes. The flow rate over this period is a constant 3 mL/minute.

In the following examples and preparations, "Et" means ethyl, "AC" means acetyl, "Me" means methyl, "ETOAC" or "ETOAc" means ethyl acetate, "THF" means tetrahydrofuran, and "Bu" means butyl.

EXAMPLE 1

3-Hydroxy-piperidine-1-carboxylic acid tert-butyl ester (B): A 3-L flask was charged with A (Scheme 1) (100 g, 0.726 mol), 1.5 L EtOH, and triethylamine (145 g). The solution was cooled to 10° C. and $(BOC)_2O$ was added dropwise as an EtOH solution (500 mL) via addition funnel over 20 min. The ice bath was remover and the reaction was stirred at room temperature overnight. The solvent was then removed in vacuo. The residue was taken up in 2 L $CH_2Cl_2$ and washed with water (×2). The organic phase was dried ($Na_2SO_4$) and concentrated to an oil. The oil was passed through a short plug of silica gel (4:1 EtOAc:hexane), which after concentration and drying gave B (150 g) as a white waxy solid.

3-(2-Methyl-4-nitro-phenoxy)-piperidine-1-carboxylic acid tert-butyl ester (C): A dry 1 L flask was charged with B (64.8 g, 322 mmol) and 475 mL dry DMF. The solution was cooled to 5° C. and NaH (8.5 g, 60% suspension in mineral oil, 354 mmol) was added in two portions over 5 min. The mixture was stirred 30 min at 10-15° C. A DMF solution (125 mL) of 2-fluoro-5-nitrotoluene (48.6 g, 313 mmol) was added dropwise via addition funnel over 20 min at 10-15° C. The reaction was stirred at room temperature overnight and TLC (Rf 3=0.25, 10% EtOAc:hexane) indicated consumption of 2-fluoro-5-nitrotoluene. The reaction was quenched by addition of 20 mL of water. The DMF was removed by rotary evaporation. The residue was taken up in 2 L EtOAc and washed with brine (×1) and water (×1). The organic phase was dried ($Na_2SO_4$) and concentrated to an oil. Purification by silica gel chromatography (10% EtOAc:hexane) gave 96.3 g of C as a yellow-green oil which solidified after vacuum drying.

3-(4-Amino-2-methyl-phenoxy)-piperidine-1-carboxylic acid tert-butyl ester (D): A 4 L stainless steel reactor was charged with $Pd(OH)_2$ (6 g, 20%, wet). Under Ar flow, 250 mL EtOH was added followed by a 2.5 L EtOH solution of C (96.0 g, 285 mmol). The reactor was sealed, purged with $H_2$ for 2-3 min, and hydrogenation was carried out at room temperature and 45 psi $H_2$ for 16 hours. The reaction mixture was filtered through Celite and the filtrate was concentrated to an oil which was further purified by silica gel chromatography (Rf=0.3, 25% EtOAc:hexane) to give 84.3 g of D as a clear, tan oil. $^1$H NMR (300 MHz, DMSO-$d_6$) δ 6.67 (1H, d, J=8.4 Hz), 6.39 (1H, s), 6.34 (1H, dd, J=8.4, 2.7 Hz), 4.57 (2H, br. s), 395-4.12 (1H, m), 3.12-3.62 (4H, m), 2.03 (3H, s), 1.61-1.96 (4H, m), 1.29 (9H, s); LRMS (M−): 305.0.

EXAMPLE 2

4-(2-Methyl-4-nitro-phenoxy)-piperidine-1-carboxylic acid tert-butyl ester (F): To a solution of E (Scheme 2) (66.4 g, 0.32 mol) in DMF (700 mL) was added NaH (16 g, 0.4 mol, 60% suspension in mineral oil) in portions at 5° C. The orange suspension was stirred at 10-15° C. for 30 min and the cooled to 5° C. 2-fluoro-5-nitrotoluene (48.6 g, 0.31 mol) was added in portions and the dark mixture was stirred at room temperature for 3 h. DMF was removed by rotary evaporation. Water (400 mL) was then added to the residue and extraction was carried out with EtOAc (3×400 mL). The combined EtOAc phases were washed with brine, dried (Na$_2$SO$_4$), and concentrated to give a 107 g of F as a yellow solid used without further purification.

4-(4-Amino-2-methyl-phenoxy)-piperidine-1-carboxylic acid tert-butyl ester (G): A 4 L stainless steel reactor was charged with Pd(OH)$_2$ (6 g, 20%, wet). Under Ar flow, 250 mL EtOH was added followed by a 2.5 L EtOH solution of F (110 g, 0.327 mol). The reactor was sealed, purged with H$_2$ for 2-3 min, and hydrogenation was carried out at room temperature and 45 psi H$_2$ for 16 hours. The residue was passed through a short pad of silica gel (EtOAc:hexane 1:1) to give a tan oil. The oil was dissolved in minimum amount of hexane and after cooling, 68 grams of G as a tan solid was collected by filtration. $^1$H NMR (300 MHz, DMSO-d$_6$) δ 6.68 (1H, d, J=8.6 Hz), 6.39 (1H, d, J=2.7 Hz), 6.34 (1H, dd, J=8.6, 2.7 Hz), 4.58 (2H, br. s), 4.14-4.22 (1H, m), 3.60-3.66 (2H, m), 3.13-3.19 (2H, m), 2.06 (3H, s), 1.79-1.86 (2H, m), 1.45-1.49 (2H, m), 1.41 (9H, s); LRMS (M−): 305.0.

EXAMPLE 3

3-Hydroxy-benzoic acid tert-butyl ester (I): A 2 L flask was charged with acid H (Scheme 3) (100 g, 0.72 mol) and 700 mL dioxane. Conc. Sulfuric acid (40 mL) was added and the solution was cooled to 0° C. with an ice bath. Isobutene was bubbled through the reaction solution for 2 h until total volume of isobutene added was ~250 mL. The solution was allowed to slowly warm to room temperature and stirred overnight. Solid NaHCO$_3$ (250 g) was cautiously added and the mixture was stirred for 1 h. Dioxane (~300 mL) was removed by rotary evaporation. Water (500 mL) was added to the residue and extraction with EtOAc (3×500 mL) was carried out. The combined organic phases were washed with a saturated solution of sodium bicarbonate followed by brine, and then was dried with Na$_2$SO$_4$. concentration provided 95 g of I as a crude oil used without further purification.

3-(2-Methyl-4-nitro-phenoxy)-benzoic acid tert-butyl ester (J): Preparation of J was carried out according to the general procedure described for F using 1 (60.5 g, 312 mmol), 450 mL DMF, and 2-fluoro-5-nitrotoluene (37.0 g, 155 mmol). The reaction mixture was stirred at room temperature for 2 days then at 50-60° C. for 2 h. Purification was then identical to that of F. The crude residue of J (73 g) was used without further purification.

3-(4-Amino-2-methyl-phenoxy)-benzoic acid tert-butyl ester (K): Hydrogenation of J was carried out for 2 h at room temperature according to the general procedure described for preparation of G, using J (73 g, 0.22 mol), Pd(OH)$_2$ (6.6 g, 20%, wet) and 1.2 L EtOH. The crude residue was triturated with hexane to give K (44 g) as a pure solid. The mother liquor was concentrated and chromatographed on silica gel (1:3 EtOAc:hexane) to give an oil which on trituration with hexane gave an additional 14.4 g of K. $^1$H NMR (300 MHz, DMSO-d$_6$) δ 7.52 (1H, d, J=7.2 Hz), 7.41 (1H, t, J=8.0 Hz), 7.24 (1H, s), 7.04-7.07 (1H, m), 6.72 (1H, d, J=8.4 Hz), 6.52 (1H, s), 6.44-6.51 (1H, m), 5.04 (2H, br. s), 1.96 (3H, s), 1.52 (9H, s); LMRS (M+): 300.2.

EXAMPLE 4

4-Hydroxy-benzoic acid tert-butyl ester (M): A 5 L flask equipped with a mechanical stirrer was charged with L (100 g, 0.72 mol), tert butyl alcohol (2 L), and 3.4 g DMAP. A solution of DCC (160 g) in dry THF (1 L) was added dropwise via addition funnel over 30 min. and the reaction was stirred 3.5 h at room temperature and then concentrated to remove THF. To the residue was added 1.5 L of diethyl ether followed by oxalic acid (100 g). The solids were filtered and the filtrate was washed with 0.3 M NaHCO$_3$ (×3). The organic phase was dried (Na$_2$SO$_4$) and concentrated to an oil which after vacuum drying gave 135 g of M that was used without further purification.

4-(2-Methyl-4-nitro-phenoxy)-benzoic acid tert-butyl ester (N): Preparation of N was carried out according to the general procedure described for the preparation of C using M (40.0 g, 0.204 mol), 600 mL DMF, NaH (9.8 g, 0.40 mol), and 2-fluoro-5-nitrotoluene (32.0 g, 0.204 mol). The reaction mixture was stirred at room temperature overnight. After an identical purification as described previously for C, crude 17 (70.6 g) was used without further purification.

4-(4-Amino-2-methyl-phenoxy)-benzoic acid tert-butyl ester (O): Hydrogenation of N was carried out for 3 h at room temperature according to the general procedure described for preparation of D, using N (75 g), Pd(OH)$_2$ (7.1 g, 20%, wet), and 1.5 L EtOH. The crude residue was chromatographed on silica gel (5% MeOH:EtOAc) to give 50.6 g of O. $^1$H NMR (300 MHz, DMSO-d$_6$) δ 7.84 (2H, d, J=8.9 Hz), 6.84 (2H, d, J=8.9 Hz), 6.73 (1H, d, J=8.4 Hz), 6.52 (1H, d, J=2.4 Hz), 6.46 (1H, dd, J=8.4, 2.4 Hz), 5.02 (2H, br. s), 1.94 (3H, s), 1.53 (9H, s); LRMS (M+): 300.2.

EXAMPLE 5a (6-Methoxy-quinazolin-4-yl)-[3-methyl-4-(piperidin-4-yloxy)-phenyl]-amine hydrochloride: 6-methoxy-4-chloro-quinazoline (5.20 g, 26.7 mmol) is combined with G (8.20 g, 26.7 mmol) in 1:1 t-butanol/1,2-dichloroethane (80 mL) and heated to reflux. The reaction is monitored by HPLC until complete (approximately 2 hours). The deprotection is done by bubbling HCl$_{anhy}$ through the solution for 5 minutes. The slurry that forms is diluted with toluene (25 mL) and cooled in an ice bath. The solids are filtered and washed with 50 mL ethyl acetate and finally dried in vacuo to provide 10.4 g (84% yield) of (6-Methoxy-quinazolin-4-yl)-[3-methyl-4-(piperidin-4-yloxy)-phenyl]-amine hydrochloride. $^1$H NMR (300 MHz DMSO d$_6$) δ 9.295 (br. s, 1H), 9.192 (br. s, 1H), 8.772 (s, 1H), 8.529 (s, 1H), 7.930 (d, J=9.2 Hz, 1H), 7.679 (dd, J=9.2, 2.4 Hz, 1H), 7.492-7.449 (m, 2H), 7.102-7.069 (m, 1H), 4.700-4.640 (m, 1H), 3.970 (s, 3H), 3.22-3.11 (m, 2H), 3.11-2.98 (m, 2H), 3.970 (s, 3H), 2.172-2.036 (m, 2H), 1.944-1.827 (m, 2H).

2-Cyclopropyl-1-{4-[4-(6-methoxy-quinazolin-4-ylamino)-2-methyl-phenoxy]-piperidin-1-yl}-ethanone: To a suspension of (6-Methoxy-quinazolin-4-yl)-[3-methyl-4-(piperidin-4-yloxy)-phenyl]-amine hydrochloride (108mg, 0.251 mmol) in N,N-dimethylformamide (1.0 mL) was added triethylamine (143 μL, 1.03 mmol) and the preformed acyl imidazolide (0.343 mmol). The acyl imidazolide is prepared by mixing CDI (56 mg, 0.343 mmol), DMF (1 mL) and cyclopropylacetic acid (34 mg, 0.343 mmol) and stirring for one hour at ambient temperature. After addition of the acyl imidazolide, the reaction was stirred at room temperature overnight. The reaction was then filtered through a 0.45 μm PTFE membrane filter and purified by preparatory HPLC. 71.4 mg of 2-Cyclopropyl-1-{4-[4-(6-methoxy-quinazolin-4-ylamino)-2-methyl-phenoxy]-piperidin-1-yl}-ethanone was isolated. $^1$H NMR (300 MHz DMSO d$_6$), δ 9.505 (s, 1H), 8.435 (s, 1H) 7.904 (d, J=9.0, 2.7 Hz, 1H), 7.708 (d, J=9.0 Hz, 1H), 7.552 (dd, J=2.7 Hz, 1H), 7.576-7.511 (m, 2H), 7.480 (dd, J=9.0, 2.7 Hz, 1H), 7.062 (d, J=9.0 Hz, 1H), 4.647-4.600 (m, 1H), 3.951 (s, 3H), 3.951-3.730 (m, 1H), (m, 1H), 3.729-3.645 (m, 1H), 3.442-3.369 (m, 3H), 2.300 (d, J=6.9 Hz, 2H), 2.223 (s, 1H), 1.985-1.882 (m, 2H), 1.692-1.576 (m, 2H) 0.980 (m, 1H), 0.499-0.439 (m, 2H), 0.162-0.113 (m, 2H).

4-[4-(6-Methoxy-quinazolin-4-ylamino)-2-methyl-phenoxy]-piperidine-1-carboxylic acid cyclopentylamide: To a suspension of (6-Methoxy-quinazolin-4-yl)-[3-methyl-4-(piperidin-4-yloxy)-phenyl]-amine hydrochloride (150 mg, 0.251 mmol) in N,N-dimethylformamide (1.5mL) was added triethylamine (143 µL, 1.03 mmol) and cyclopentyl isocyanate (0.343 mmol). The reaction was stirred at room temperature overnight The reaction was then filtered through a 0.45 µm PTFE membrane filter and purified by preparatory HPLC. 36.3 mg of 4-[4-(6-Methoxy-quinazolin-4-ylamino)-2-methyl-phenoxy]-piperidine-1-carboxylic acid cyclopentylamide was isolated. $^1$H NMR (300 MHz, DMSO d$_6$) δ 9.505 (s, 1H), 8.436 (s, 1H), 7.904 (d, J=0.9 Hz, 1H), 7.707 (d, J=3.0 Hz, 1H), 7.498-7.458 (dd, J=9.0, 3.0 Hz, 1H), 7.571-7.513 (m, 2H), 7.045 (d, J=3.0 Hz, 1H), 6.28 (d, J=2.3 Hz, 1H), 4.564-4.514 (m, 1H), 3.962-3.894 (m, 1H), 3.950 (s, 3H), 3.677-3.599 (m, 2H), 3.246-3.163 (m, 2H), 2.216 (s, 3H), 1.928-1.863 (m, 2H), 1.862-1.751 (m, 2H) 1.671-1.518 (m, 4H), 1.517-1.365 (m, 4H).

EXAMPLE 5b (6,7-Dimethoxy-quinazolin-4-yl)-[3-methyl-4-(piperidin-4-yloxy)-phenyl]-amine hydrochloride: To a solution of 1,2-dichloroethane (20 mL) and tert-butylalcohol was added 4-chloro-6,7-dimethoxy-quinazoline (3.0 g, 13.35 mmol) and 4-(4-amino-2-methyl-phenoxy)-piperidine-1-carboxylic acid tert-butyl ester (G) (4.09 g, 13.35 mmol). The reaction was heated at 90° C. for 45 minutes. The reaction was cooled to room temperature then hydrogen chloride gas was bubbled in for 40 minutes. A small amount of methanol was added to dissolve the gummed solids. Ethyl acetate (50 mL) was added and solids crystallized out. The solids were filtered and rinsed with cold 1,2-dichloroethane and ethyl acetate yielding 5.2 g of light yellow solids. $^1$H NMR (400 MHz, DMSO-d$_6$) δ 11.35(s, 1H), 8.99(bs, 1H), 8.90(bs, 1H), 8.74(s, 1H), 8.29(s, 1H), 7.39(d, J=2.49 Hz, 2H), 7.31(s, 1H), 7.09(d, J=8.31 Hz, 1H), 4.67(m, 1H), 3.97(s, 3H), 3.95(s, 3H), 3.17(m, 2H), 3.08(m, 2H), 2.19(s, 3H), 2.09(m, 2H), 1.87(m, 3H), LMRS (M+): 395.3, (M−): 393.4.

Protocol for: 4-[4-(6,7-Dimethoxy-quinazolin-4-ylamino)-2-methyl-phenoxy]-piperidine-1-carboxylic acid (2,6-difluoro-phenyl)-amide, 4-[4-(6,7-Dimethoxy-quinazolin-4-ylamino)-2-methyl-phenoxy]-piperidine-1-carboxylic acid (4-methoxyphenyl)-amide, 4-[4-(6,7-Dimethoxy-quinazolin-4-ylamino)-2-methyl-phenoxy]-piperidine-1-carboxylic acid (tetrahydro-pyran-4-yl)-amide, 4-[4-(6,7-Dimethoxy-quinazolin-4-ylamino)-2-methyl-phenoxy]-piperidine-1-carboxylic acid (2,5-difluoro-phenyl)-amide, 4-[4-(6,7-Dimethoxy-quinazolin-4-ylamino)-2-methyl-phenoxy]-piperidine-1-carboxylic acid cyclopentylamide: To a suspension of (6,7-dimethoxy-quinazolin-4-yl)-[3-methyl-4-(piperidin-4-yloxy)-phenyl]-amine hydrochloride (108 mg, 0.251 mmol) in N,N-dimethylformamide (2 mL) was added triethylamine (116 µL, 0.837 mmol) and the necessary isocyanate (0.279 mmol). The reaction was stirred at room temperature overnight. The reaction was then filtered through a 0.45 µm PTFE membrane filter and purified by preparatory HPLC.

Protocol for: 1-{4-[4-(6,7-Dimethoxy-quinazolin-4-ylamino)-2-methyl-phenoxy]-piperidin-1-yl}-3,3-dimethyl-butan-1-one, {4-[4-(6,7-Dimethoxy-quinazolin-4-ylamino)-2-methyl-phenoxy]-piperidin-1-yl}-(3-methoxy-phenyl)-methanone, Cyclopentyl-{4-[4-(6,7-dimethoxy-quinazolin-4-ylamino)-2-methyl-phenoxy]-piperidin-1-yl}-methanone, 2-Cyclopentyl-1-{4-[4-(6,7-dimethoxy-quinazolin-4-ylamino)-2-methyl-phenoxy]-piperidin-1-yl}-ethanone: To a suspension of (6,7-dimethoxy-quinazolin-4-yl)-[3-methyl-4-(piperidin-4-yloxy)-phenyl]-amine hydrochloride (108 mg, 0.251 mmol) in N,N-dimethylformamide (2 mL) was added triethylamine (116 µL, 0.837 mmol) and the necessary acid chloride (0.279 mmol). The reaction was stirred at room temperature overnight. LC/MS confirmed that starting material was consumed and the correct product had formed. The reaction was then filtered through a 0.45 µm PTFE membrane filter and purified by preparatory HPLC.

{4-[4-(6,7-Dimethoxy-quinazolin-4-ylamino)-2-methyl-phenoxy]-piperidin-1-yl}-(tetrahydro-furan-2-yl)-methanone: To a solution of 1,1'-carbonyldiimidizole (41.38 mg, 0.255 mmol) in N,N-dimethylformamide (1 mL) was added (R)-(+)-tetrahydrofuroic acid (29.6 mg, 0.255 mmol). The reaction was stirred at room temperature for 30 minutes then (6,7-dimethoxy-quinazolin-4-yl)-[3-methyl-4-(piperidin-4-yloxy)-phenyl]-amine hydrochloride was added. The reaction was stirred at room temperature overnight. The following day, the reaction was filtered through a 0.45 µm PTFE membrane filter and purified by preparatory HPLC. $^1$H NMR (300 MHz, DMSO-d$_6$) δ 9.35 (s, 1H), 8.39 (s, 1H), 8.15 (s, 1H), 7.82 (s, 1H), 7.51(d, d, J=8.71 Hz, 2H), 7.16(s, 1H), 7.05(d, J=8.4 Hz, 1H), (t, J=13.06 Hz, 7.15 Hz, 1H), 3.95(s, 3H), 3.93(s, 3H), 3.75(m, 4H), 3.44(m, 2H), 2.21(s, 3H), 2.03(m, 4H), 1.85(m, 2H), 1.70(m, 2H), LMRS (M+): 493.5, (M−): 491.5.

[6,7-Bis-(2-methoxy-ethoxy)-quinazolin-4-yl]-[3-methyl-4-(piperidin-4-yloxy)-phenyl]-amine hydrochloride: To a solution of 1,2-dichloroethane (20 mL) and tert-butylalcohol was added 4-chloro-6,7-bis-(2-methoxy-ethoxy)-quinazoline and 4-(4-amino-2-methyl-phenoxy)-piperidine-1-carboxylic acid tert-butyl ester. The reaction was heated at 90° C. for 1 hour. The reaction was cooled to room temperature then hydrogen chloride gas was bubbled in for 10 minutes. Ethyl acetate (30 mL) was added then cooled to 0° C. for 30 minutes. The solids were filtered and rinsed with ethyl acetate. Light yellow solids were further dried in a vacuum oven yielding the mono hydrochloride salt (1.91 g, 99%). $^1$H NMR (400 MHz, DMSO-d$_6$) δ 11.42(s, 1H), 9.15(bs, 1H), 9.05(bs, 1H), 8.72(s, 1H), 8.40(s, 1H), 7.41(d, J=17.03 Hz, 2H), 7.40(d, J=2.49 Hz, 1H), 7.08(d, J=8.30 Hz, 1H), 4.67(m, 1H), 4.34(t, J=9.14, 4.98 Hz, 2H), 4.27(t, J=8.72, 4.56 Hz, 2H), 3.74(t, J=5.81, 3.32, 4H), 3.16(m, 2H), 3.07(m, 2H), 2.18(s, 3H), 2.10(m, 2H), LRMS (M+): 483.3, (M−): 481.3).

Protocol for: 4-{4-[6,7-Bis-(2-methoxy-ethoxy)-quinazolin-4-ylamino]-2-methyl-phenoxy}-piperidine-1-carboxylic acid (2,6-difluoro-phenyl)-amide, 4-{4-[6,7-Bis-(2-methoxy-ethoxy)-quinazolin-4-ylamino]-2-methyl-phenoxy}-piperidine-1-carboxylic acid (4-methoxy-phenyl)-amide, (4-{4-[6,7-Bis-(2-methoxy-ethoxy)-quinazolin-4-ylamino]-2-methyl-phenoxy}-piperidin-1-yl)-morpholin-4-yl-methanone, 4-{4-[6,7-Bis-(2-methoxy-ethoxy)-quinazolin-4-ylamino]-2-methyl-phenoxy}-piperidine-1-carboxylic acid (2,5-difluoro-phenyl)-amide, 4-{4-[6,7-Bis-(2-methoxy-ethoxy)-quinazolin-4-ylamino]-2-methyl-phenoxy}-piperidine-1-carboxylic acid cyclopentylamide: To a suspension of [6,7-Bis-(2-methoxy-ethoxy)-quinazolin-4-yl]-[3-methyl-4-(piperidin-4-yloxy)-phenyl]-amine hydrochloride (130 mg, 0.251 mmol) in N,N-dimethylformamide was added triethylamine (78 µL, 0.558 mmol) and the necessary isocyanate (0.279 mmol). The reaction was stirred at room temperature overnight. The following day, the reaction was filtered through a 0.45 µM PTFE membrane filter and purified by preparatory HPLC.

Protocol for: 1-(4-{4-[6,7-Bis-(2-methoxy-ethoxy)-quinazolin-4-ylamino]-2-methyl-phenoxy}-piperidin-1-yl)-3,3-dimethyl-butan-1-one, (4-{4-[6,7-Bis-(2-methoxyethoxy)-quinazolin-4-ylamino]-2-methyl-phenoxy}-piperidin-1-yl)-(3-methoxy-phenyl)-methanone, 1-(4-{4-[6,7-Bis-(2-methoxy-ethoxy)-quinazolin-4-ylamino]-2-methyl-phenoxy}-piperidin-1-yl)-2-cyclopentyl-ethanone, (4-{4-[6,7-Bis-(2-methoxy-ethoxy)-quinazolin-4-ylamino]-2-methyl-phenoxy}-piperidin-1-yl)-cyclopentyl-methanone: To a suspension of [6,7-Bis-(2-methoxy-ethoxy)-quinazolin-4-yl]-[3-methyl-4-(piperidin-4-yloxy)-phenyl]-amine hydrochloride (130 mg, 0.251 mmol) in N,N-dimethylformamide was added triethylamine (78 µL, 0.558 mmol) and the relevant acid chloride (0.279 mmol). The reaction was stirred at room temperature overnight. The following day, the reaction was filtered through a 0.45 µM PTFE membrane filter and purified by preparatory HPLC.

(4-{4-[6,7-Bis-(2-methoxy-ethoxy)-quinazolin-4-ylamino]-2-methyl-phenoxy}-piperidin-1-yl)-(tetrahydro-furan-2-yl)-methanone: To a solution of 1,1'-carbonyldiimidizole (35 mg, 0.221 mmol) in N,N-dimethylformamide (2 mL) was added (R)-(+)-tetrahydrofuroic acid (25 mg, 0.221 mmol). The reaction was stirred at room temperature for 30 minutes then [6,7-Bis-(2-methoxy-ethoxy)-quinazolin-4-yl]-[3-methyl-4-(piperidin-4-yloxy)-phenyl]-amine hydrochloride (100 mg, 0.193 mmol) was added. The reaction was then stirred at room temperature overnight. The following day, the reaction was filtered through a 0.45 µm PTFE membrane filter and purified by preparatory HPLC. $^1$H NMR (300 MHz, DMSO-$d_6$) δ 9.38(bs, 1H), 8.39(s, 1H), 8.15(s, 1H), 7.85(s, 1H), 7.52(d, J=8.39 Hz, 1H), 7.19(s, 1H), 7.04(d, J=8.71 Hz, 1H), 4.70(t, J=7.46, 1.55 Hz, 1H), 4.64(t, J=18.66, 3.42 Hz, 1H), 4.84(t, J=4.97, 3.75 Hz, 2H), 3.77(m, 8H), 3.43(m, 2H), 3.38(s, 3H), 3.36(s, 3H), 2.21(s, 3H), 2.05(m, 4H), 1.90(m, 2H), 1.66(m, 2H), LRMS (M+): 581.1, (M−): 579.2.

3-[4-(6,7-Dimethoxy-quinazolin-4-ylamino)-2-methyl-phenoxy]-benzoic acid hydrochloride: To a suspension of 4-chloro-6,7-dimethoxy-quinazoline (3.0 g, 13.35 mmol) in 1,2-dichloroethane (40 mL) and tert-butyl alcohol (40 mL) was added 3-(4-amino-2-methyl-phenoxy)-benzoic acid tert-butyl ester (3.99 g, 13.35 mmol). The reaction was heated at 90° C. for 90 minutes. The reaction was then cooled to room temperature and hydrogen chloride gas was bubbled through the solution for 40 minutes. A small amount of hot methanol was added to solublize the gummed solids. Solids then crashed out upon cooling. The solids were filtered and rinsed with cold ethyl acetate. The solids were further dried at 50° C. in a vacuum oven, yielding light yellow solids as the mono hydrochloride salt (5.79 g, 93%). $^1$H NMR (400 MHz, DMSO-$d_6$) δ 11.39(bs, 1H), 8.82(s, 1H), 8.29(s, 1H), 7.64(d, J=7.06 Hz, 1H), 7.63(s, 1H), 7.55(d, J=8.72 Hz, 1H), 7.50(t, J=15.78, 7.89 Hz, 1H), 7.33(s, 1H), 7.30(s, 1H), 7.08(d, J=8.72 Hz, 1H), 3.98(s, 3H), 3.96(s, 3H), 2.17(s, 3H), LRMS (M+): 732.3, (M−): 430.3.

Protocal for: 3-[4-(6,7-Dimethoxy-quinazolin-4-ylamino)-2-methyl-phenoxy]-N-(2,2-dimethyl-propyl)-benzamide, 3-[4-(6,7-Dimethoxy-quinazolin-4-ylamino)-2-methyl-phenoxy]-N-pentyl-benzamide, 1-{3-[4-(6,7-dimethoxy-quinazolin-4-ylamino)-2-methyl-phenoxy]-phenyl}-2-piperidin-1-yl-ethanone, 3-[4-(6,7-dimethoxy-quinazolin-4-ylamino)-2-methyl-phenoxy]-N-(4-methoxy-phenyl)-benzamide, 3-[4-(6,7-Dimethoxy-quinazolin-4-ylamino)-2-methyl-phenoxy]-N-(2-fluoro-phenyl)-benzamide, {3-[4-(6,7-Dimethoxy-quinazolin-4-ylamino)-2-methyl-phenoxy]-phenyl}-piperidin-1-yl-methanone, 3-[4-(6,7-Dimethoxy-quinazolin-4-ylamino)-2-methyl-phenoxy]-N-(2-piperidin-1-yl-ethyl)-benzamide: To a suspension of 3-[4-(6,7-dimethoxy-quinazolin-4-ylamino)-2-methyl-phenoxy]-benzoic acid hydrochloride (100 mg, 0.235 mmol) in N,N-dimethylformamide (2 mL) was added triethylamine (131 µL, 0.94 mmol) and O-(7-azabenztriazol-1-yl)-N,N,N',N'-tetramethyluronium hexafluorophosphate (178 mg, 0.47 mmol) followed by the relevant amine (0.47 mmol). The reaction was stirred at room temperature overnight. The following day, the reaction was filtered through a 0.45 µm PTFE membrane filter and purified by preparatory HPLC.

4-[4-(6,7-Dimethoxy-quinazolin-4-ylamino)-2-methyl-phenoxy]-benzoic acid hydrochloride: To a suspension of 4-chloro-6,7-dimethoxy-quinazoline (3.0 g, 13.35 mmol) in 1,2-dichloroethane (40 mL) and tert-butyl alcohol (40 mL) was added 4-(4-amino-2-methyl-phenoxy)-benzoic acid tert-butyl ester (3.99 g, 13.35 mmol). The reaction was heated at 90° C. for 90 minutes. The reaction was then cooled to room temperature and hydrogen chloride gas was bubbled through the solution for 40 minutes. A small amount of hot methanol was added to solublize the gummed solids. Solids then crashed out upon cooling. The solids were filtered and rinsed with cold ethyl acetate. The solids were further dried at 50° C. in a vacuum oven, yielding light yellow solids (5.99 g, 96%) as the mono hydrochloride salt. $^1$H NMR (400 MHz, DMSO-$d_6$) δ 8.82(s, 1H), 8.40(s, 1H), 7.93(d, J=9.14 Hz, 2H), 7.67(d, J=2.07 Hz, 1H), 7.37(s, 1H), 7.13(d, J=8.72 Hz, 1H), 6.94(d, J=8.72 Hz, 2H), 3.99(s, 3H), 3.96(s, 3H), 2.14(s, 3H), LRMS (M+): 432.3, (M−): 430.2.

Protocol for: 4-[4-(6,7-Dimethoxy-quinazolin-4-ylamino)-2-methyl-phenoxy]-N-(2,2-dimethyl-propyl)-benzamide, 4-[4-(6,7-Dimethoxy-quinazolin-4-ylamino)-2-methyl-phenoxy]-N-pentyl-benzamide, N-Cyclohexyl-4-[4-(6,7-dimethoxy-quinazolin-4-ylamino)-2-methyl-phenoxy]-benzamide, 4-[4-(6,7-Dimethoxy-quinazolin-4-ylamino)-2-methyl-phenoxy]-N-(4-methoxy-phenyl)-benzamide, 4-[4-(6,7-Dimethoxy-quinazolin-4-ylamino)-2-methyl-phenoxy]-N-(2-fluoro-phenyl)-benzamide, {4-[4-(6,7-Dimethoxy-quinazolin-4-ylamino)-2-methyl-phenoxy]-phenyl}-piperidin-1-yl-methanone, 4-[4-(6,7-Dimethoxy-quinazolin-4-ylamino)-2-methyl-phenoxy]-N-(2-piperidin-1-yl-ethyl)-benzamide: To a suspension of 4-[4-(6,7-dimethoxy-quinazolin-4-ylamino)-2-methyl-phenoxy]-benzoic acid hydrochloride (100 mg, 0.235 mmol) in N,N-dimethylformamide (2 mL) was added triethylamine (131 µL, 0.94 mmol) and O-(7-azabenztriazol-1-yl)-N,N,N',N'-tetramethyluronium hexafluorophosphate (178 mg, 0.47 mmol) followed by the amine (0.47 mmol). The reaction was stirred to room temperature overnight. The following day, the reaction was filtered through a 0.45 µm PTFE membrane filter and purified by preparatory HPLC.

EXAMPLE 6

(6-Fluoro-pyrido[3,4-d]pyrimidin-4-yl)-[3-methyl-4-(piperidin-4-yloxy)-phenyl]-amine A solution of 6-Fluoro-3H-pyrido[3,4-d]pyrimidin-4-one (1.5 g, 9.14 mmol), SOCl$_2$ (10.87 g, 91.4 mmol), and DMF (0.3 mL) in DCE (30 mL) was heated to reflux for 4 h. The reaction was then concentrated and the resulting dark residue was dissolved in t-BuOH/DCE 1:1 (30 mL), NEt$_3$ (1.02 g, 10.0 mmol) and 4-(4-Amino-2-methyl-phenoxy)-piperidine-1-carboxylic acid tert-butyl ester (G) (2.8 g, 9.14 mmol) were added, the resulting solution was heated to reflux for 2 h. The solution was cooled to room temperature then treated with HCl (gas). The title compound T was collected via filtration as a yellow solid (3.66 g, 94%).

LRMS: 354.3 (MH+); $^1$H NMR (DMSO-$d_6$, 400 MHz): δ 9.21 (br. s, 1H), δ 9.11 (br. s, 1H), δ 9.00 (s, 1H), δ 8.87 (s, 1H), δ 8.82 (s, 1H), δ 7.55-7.57 (m, 2H), δ 7.09 (d, J=9.95 Hz, 1H), δ 4.66-4.69 (m, 1H), δ 2.99-3.16 (m, 4H), δ 2.18 (s, 3H), δ 2.08-2.13 (m, 2H), δ 1.86-1.90 (m, 2H).

Cyclopentyl-{4-[4-(6-fluoro-pyrido[3,4-d]pyrimidin-4-ylamino)-2-methyl-phenoxy]-piperidin-1-yl}-methanone: Cyclopentane carbonyl chloride (0.187 g, 1.41 mmol) was added to a solution of (6-Fluoro-pyrido[3,4-d]pyrimidin-4-yl)-[3-methyl-4-(piperidin-4-yloxy)-phenyl]-amine (T) (0.50 g, 1.28 mmol) and NEt$_3$ (0.38 g, 3.84 mmol) in CH$_2$Cl$_2$ (15 mL After 1 h the reaction was quenched with water, the layers were separated and the organic layer was washed with 1N NaOH and water, dried over Na$_2$SO$_4$, and concentrated. Purification by flash column chromatography (CH$_2$Cl$_2$/MeOH, 97/3) afforded the title compound as a yellow solid (0.40 g, 70%). LRMS: 450.3 (MH+); $^1$H NMR (DMSO-d$_6$, 400 MHz): δ 9.90 (s, 1H), δ 8.86 (s, 1H), δ 8.58 (s, 1H), δ 8.19 (s, 1H), δ 7.54-7.56 (m, 2H), δ 7.04 (d, J=9.56 Hz, 1H) δ 4.58-4.61 (m, 1H), δ 3.70-3.72 (m, 2H), δ 3.33-3.44 (m, 2H), δ 2.93-3.008 (m, 1H), δ 2.17 (s, 3H), δ 1.46-1.94 (m, 12H).

4-[4-(6-Fluoro-pyrido[3,4-d]pyrimidin-4-ylamino)-2-methyl-phenoxy]-piperidine-1-carboxylic acid (2,6-difluoro-phenyl)-amide: 2,6-difluorophenyl Isocyanate (0.199 g, 1.28 mmol) was added to a solution of (6-Fluoro-pyrido[3,4-d]pyrimidin-4-yl)-[3-methyl-4-(piperidin-4-yloxy)-phenyl]-amine hydrochloride (T) (500 mg, 1.28 mmol) and NEt$_3$ (0.388 g, 3.84 mmol) in CH$_2$Cl$_2$ (20 mL). After 1 h the reaction was quenched with water, the layers were separated and the organic layer was washed with 1N NaOH and water, dried over Na$_2$SO$_4$, and concentrated. Purification by flash column chromatography (CH$_2$Cl$_2$/MeOH 97:3) afforded the title compound as a yellow solid (0.50 g, 77%). LRMS: 509.2 (MH+); $^1$H NMR (DMSO-d$_6$, 400 MHz): δ 9.90 (s, 1H), δ 8.86 (s, 1H), δ 8.58 (s, 1H), δ 8.28 (s, 1H), δ 8.19 (s, 1H), δ 7.55-7.58 (m, 2H), δ 7.20-7.27 (m, 1H), δ 7.04-7.10 (m, 3H), δ 4.58-4.61 (m, 1H), δ 3.69-3.73 (m, 2H), δ 3.33-3.98 (m, 2H), δ 2.19 (s, 3H), δ 1.91-1.96 (m, 2H), δ 1.60-1.66 (m, 2H).

2-Cyclopentyl-1-{4-[4-(6-fluoro-pyrido[3,4-d]pyrimidin-4-ylamino)-2-methyl-phenoxy]-piperidin-1-yl}-ethanone: The title compound was prepared from (6-Fluoro-pyrido[3,4-d]pyrimidin-4-yl)-[3-methyl-4-(piperidin-4-yloxy)-phenyl]-amine (T) and cyclopentylacetyl chloride by a procedure analogous to that described for the synthesis of Cyclopentyl-{4-[4-(6-fluoro-pyrido[3,4-d]pyrimidin-4-ylamino)-2-methyl-phenoxy]-piperidin-1-yl}-methanone. MS: 464.3 (MH+); $^1$H NMR (DMSO-d$_6$, 400 MHz): δ 9.90 (s, 1H), δ 8.86 (s, 1H), δ 8.57 (s, 1H), δ 8.19 (s, 1H), δ 7.035 (d, J=9.97, 2H), δ 4.58-4.59 (m, 1H), δ 3.71 (m, 2H), δ 3.30-3.93 (m, 2H), δ 2.31 (d, J=7.47, 2H), δ 2.17 (s, 3H), δ 2.08-2.12 (m, 1H), δ 1.80-1.95 (m, 1H), δ 1.43-1.73 (m, 10H), δ 1.05-1.10 (m, 2H).

Cyclopentyl-{4-[2-methyl-4-(6-pyrrolidin-1-yl-pyrido[3,4-d]pyrimidin-4-ylamino)-phenoxy]-piperidin-1-yl}-methanone: A solution of Cyclopentyl-{4-[4-(6-fluoro-pyrido[3,4-d]pyrimidin-4-ylamino)-2-methyl-phenoxy]-piperidin-1-yl}-methanone (50 mg, 0.11 mmol), pyrrolodine (15.8 mg, 0.222 mmol), and NEt$_3$ (33.7 mg, 0.333 mmol) in DMSO (1 mL) was heated to 120° C. for 12 h. The reaction was concentrated and purified by preparative HPLC to give the title compound as a yellow solid (22 mg, 40%). MS: 501.4 (MH+); $^1$H NMR (DMSO-d$_6$, 400 MHz): δ 8.84 (s, 1H), δ 8.30 (s, 1H), δ 7.50-7.54 (m, 2H), δ 7.24 (s, 1H), δ 6.08 (d, J=8.72 Hz, 1H), δ 6.55 (s, 1H), δ 4.52 (m, 1H), δ 3.70 (m, 3H), δ 3.48-3.65 (m, 4H) δ 2.86-2.94 (m, 1H), δ 2.22 (s, 3H), 1.53-2.00 (m, 17H)

4-[4-(6-Fluoro-pyrido[3,4-d]pyrimidin-4-ylamino)-2-methyl-phenoxyl-piperidine-1-carboxylic acid tert-butyl ester: A solution of 6-Fluoro-3H-pyrido[3,4-d]pyrimidin-4-one (2.0 g, 12.11 mmol), SOCl$_2$ (14.4 g, 121.1 mmol), and DMF (0.4 mL) in DCE (40 mL) was heated to reflux for 4 h. The reaction was then concentrated and the resulting dark residue was dissolved in t-BuOH/DCE 1:1 (40 mL), NEt$_3$ (2.45 g, 24.22 mmol) and 4-(4-Amino-2-methyl-phenoxy)-piperidine-1-carboxylic acid tert-butyl ester (3.7 g, 12.11 mmol) were added, the resulting solution was heated to reflux for 2 h. The reaction was concentrated, the residue was dissolved in EtOAc and washed 2× water then the organic layer was dried over Na$_2$SO$_4$. Purification by flash column chromatography (CH$_2$Cl$_2$/MeOH 98:2) gave the title compound as a yellow solid (3.08 g, 56%). LRMS: 454.2; 398.2; 354.2 (MH+); $^1$H NMR (DMSO-d$_6$, 400 MHz): δ 9.88 (s, 1H), δ 8.84 (s, 1H), δ 8.56 (s, 1H), δ 8.17 (s, 1H), δ 7.53-7.55 (m, 2H), δ 7.00-7.02 (m, 1H), δ 4.50-4.55 (m, 1H), δ 3.21-3.26 (m, 2H), δ 2.16 (s, 3H), δ 1.83-1.89 (m, 2H), δ 1.51-1.59 (m, 1H), δ 1.37 (s, 9H).

[3-Methyl-4-(piperidin-4-yloxy)-phenyl]-(6-morpholin-4-yl-pyrido[3,4-d]pyrimidin-4-yl)-amine: A solution of 4-[4-(6-Fluoro-pyrido[3,4-d]pyrimidin-4-ylamino)-2-methyl-phenoxy]-piperidine-1-carboxylic acid tert-butyl ester (1.0 g, 2.21 mmol), NEt$_3$ (0.67 g, 6.63 mmol), and morpholine (0.57 g, 6.63 mmol) in DMSO (10 mL) was heated to 120° C. in a sealed tube. After 24 h the reaction was diluted with EtOAc, the organic layer was washed 2× 1N NaOH and 2× water. The organic layer was treated with HCl (g) and the title compound was collected by filtration as a yellow solid (0.63 g, 67%). LRMS: 421.3 (MH+). $^1$H NMR (DMSO-d$_6$, 400 MHz): δ 9.15 (br. s, 1H), δ 9.05 (br. s, 1H), δ 8.92 (s, 1H), δ 8.65 (s, 1H), δ 8.18 (s, 1H), δ 7.49-7.51 (m, 2H), δ 7.096 (d, J=9.55, 1H), δ 4.66-4.69 (m, 1H), δ 3.65-3.73 (m, 8H), δ 3.16 (br. s, 2H), δ 3.06 (br. s, 2H), δ 2.17 (s, 3H), δ 2.07-2.13 (m, 2H), δ 1.85-1.94 (m, 2H).

3,3-Dimethyl-1-{4-[2-methyl-4-(6-morpholin-4-yl-pyrido[3,4-d]pyrimidin-4-ylamino)-phenoxy]-piperidin-1-yl}-butan-1-one: The title compound was prepared from [3-Methyl-4-(piperidin-4-yloxy)-phenyl]-(6-morpholin-4-yl-pyrido[3,4-d]pyrimidin-4-yl)-amine and tert-butylacetyl chloride by a procedure analogous to the synthesis of Cyclopentyl-{4-[4-(6-fluoro-pyrido[3,4-d]pyrimidin-4-ylamino)-2-methyl-phenoxy]-piperidin-1-y}-methanone above.

MS: 519.3 (MH+).

(3-Methoxy-phenyl)-{4-[2-methyl-4-(6-morpholin-4-yl-pyrido[3,4-d]pyrimidin-4-ylamino)-phenoxy]-piperidin-1-yl}-methanone: The title compound was prepared from [3-Methyl-4-(piperidin-4-yloxy)-phenyl]-(6-morpholin-4-yl-pyrido[3,4-d]pyrimidin-4-yl)-amine and 3-methoxy benzoylchloride by a procedure analogous to the synthesis of Cyclopentyl-{4-[4-(6-fluoro-pyrido[3,4-d]pyrimidin-4-ylamino)-2-methyl-phenoxy]-piperidin-1-yl}-methanone. LRMS: 555.2 (MH+). $^1$H NMR (DMSO-d$_6$, 400 MHz): δ 9.57 (s, 1H), δ 8.79 (s, 1H), δ 8.32 (s, 1H), δ 7.47-7.53 (m, 3H), δ 7.32 (t, J=7.68, 1H), δ 7.31 (d, J=8.72, 1H), δ 6.93-6.99 (m, 3H), δ 4.62 (br. s, 1H), δ 3.76 (br. s, 1H), δ 3.52-3.54 (m, 6H), δ 3.75 (m, 6H), 3.302 (s, 3H), δ 2.18 (s, 3H), δ 1.97 (br. s, 1H), δ 1.90 (br. s, 1H), δ 1.66 (br. s, 1H).

4-[2-Methyl-4-(6-morpholin-4-yl-pyrido[3,4-d]pyrimidin-4-ylamino)-phenoxy]-piperidine-1-carboxylic acid cyclopentylamide: The title compound was prepared from [3-Methyl-4-(piperidin-4-yloxy)-phenyl]-(6-morpholin-4-yl-pyrido[3,4-d]pyrimidin-4-yl)-amine and cyclopentyl isocyanate by a procedure analogous to the synthesis of 4-[4-(6-Fluoro-pyrido[3,4-d]pyrimidin-4-ylamino)-2-methyl-phenoxy]-piperidine-1-carboxylic acid (2,6-difluoro-phenyl)-amide above. LRMS: 532.3/421.3 (MH+); $^1$H NMR (DMSO-d$_6$, 400 MHz): δ 9.57 (s, 1H), δ 8.78 (s, 1H), δ 8.32 (s, 1H), δ 7.48-7.54 (m, 3H), δ 7.12 (d, J=9.14 1H), δ 6.24 (d, J=7.30, 1H), δ 4.50-5.19 (m, 1H), δ 3.84-3.89 (m, 1H), δ

3.74-3.76 (m, 4H), δ 3.51-3.59 (m, 6H), δ 3.12-3.18 (m, 2H), δ 2.16 (s, 3H), δ 1.81-1.86 (m, 4H), δ 1.29-1.76 (m, 8H).

EXAMPLE 7

3-[4-(6-Fluoro-pyrido[3,4-d]pyrimidin-4-ylamino)-2-methyl-phenoxy]-benzoic acid tert-butyl ester: A solution of 6-Fluoro-3H-pyrido[3,4-d]pyrimidin-4-one (0.5 g, 3.05 mmol), $SOCl_2$ (3.63 g, 30.5 mmol), and DMF (0.2 mL) in DCE (20 mL) was heated to reflux for 12 h. The reaction was then concentrated and the resulting dark residue was dissolved in t-BuOH/DCE 1:1 (20 mL), $NEt_3$ (0.34 g, 3.36 mmol) and 3-(4-Amino-2-methyl-phenoxy)-benzoic acid tert-butyl ester (0.91 g, 3.05 mmol) were added, the resulting solution was heated to reflux for 5 h. The reaction was concentrated, the residue was dissolved in EtOAc and washed 2× water then the organic layer was dried over $Na_2SO_4$. Purification by flash column chromatography (Hexane/Ethyl Acetate 4:6) gave the title compound as a yellow solid (1.1 g, 80%). LRMS: 447.3/391.2 (MH+). $^1$H NMR (DMSO-$d_6$, 400 MHz): δ 10.03 (s, 1H), δ 8.90 (s, 1H), δ 8.65 (s, 1H), δ 8.23 (s, 1H), δ 7.803 (d, 1H), δ 7.73 (dd, J=6.23, 2.49, 1H), δ 7.58 (d, 1H) δ 7.45 (t, J=7.89, 1H), δ 7.31-7.32 (m, 1H), δ 7.14-7.16 (m, 1H), δ 7.027 (d, J=8.72, 1H), δ 2.16 (s, 3H), δ 1.48 (s, 9H).

3-[2-Methyl-4-(6-pyrrolidin-1-yl-pyrido[3,4-d]pyrimidin-4-ylamino)-phenoxy]-benzoic acid tert-butyl ester: The Title compound was prepared from 3-[4-(6-Fluoro-pyrido[3,4-d]pyrimidin-4-ylamino)-2-methyl-phenoxy]-benzoic acid tert-butyl ester and pyrrolidine by a procedure analogous to that described for the synthesis of Cyclopentyl-{4-[2-methyl-4-(6-pyrrolidin-1-yl-pyrido[3,4-d]pyrimidin-4-ylamino)-phenoxy]-piperidin-1-yl}-methanone. LRMS: 498.3 (MH+). $^1$H NMR (DMSO-$d_6$, 400 MHz): δ 9.60 (s, 1H), δ 8.76 (s, 1H), δ 8.31 (s, 1H), δ 7.73-7.76 (m, 2H), δ 7.56-7.58 (m, 1H), δ 7.45 (t, J=7.89, 1H), δ 7.31-7.32 (m, 1H), δ 7.13-7.16 (m, 1H), δ 7.09 (s, 1H), 7.01 (d, J=9.14, 1H), δ 3.45-3.48 (m, 4H), δ 2.15 (s, 3H), δ 1.97-2.01 (m, 4H), δ 1.48 (s, 9H).

3-[2-Methyl-4-(6-pyrrolidin-1-yl-pyrido[3,4-d]pyrimidin-4-ylamino)-phenoxy]-benzoic acid: Trifluoro acetic acid (10 mL) was added to a solution of 3-[2-Methyl-4-(6-pyrrolidin-1-yl-pyrido[3,4-d]pyrimidin-4-ylamino)-phenoxy]-benzoic acid tert-butyl ester (0.40 g, 0.82 mmol) in $CH_2Cl_2$ (10 mL). After 12 h the reaction was concentrated to give a red solid (0.36 g, 100%). LRMS: 4.42 (MH+), HPLC Rf: 8.34 min.

N-tert-Butyl-3-[2-methyl-4-(6-pyrrolidin-1-yl-pyrido[3,4-d]pyrimidin-4-ylamino)-phenoxy]-benzamide: A solution of 3-[2-Methyl-4-(6-pyrrolidin-1-yl-pyrido[3,4-d]pyrimidin-4-ylamino)-phenoxy]-benzoic acid (72 mg, 0.16 mmol), HATU (93 mg, 0.24 mmol), $NEt_3$ (50 mg, 0.48 mmol), and tert-butyl amine (24 mg, 0.33 mmol) in DMF (1.5 mL) was shaken at 60° C. for 12 h. The reaction was concentrated and purified by preparative HPLC to give a yellow solid (28 mg, 35%). LRMS: 497.3 (MH+); $^1$H NMR (DMSO-$d_6$, 400 MHz): δ 9.65 (s, 1H), δ 8.81 (s, 1H), δ 8.36 (s, 1H), δ 7.77-7.81 (m, 3H), δ 7.54 (d, J=7.78, 1H), δ 7.42 (t, J=7.78, 1H), δ 7.34-7.35 (m, 1H), δ 7.14 (s, 1H), δ 7.00-7.069 (m, 2H), δ 3.50-3.54 (m, 4H), δ 2.21 (s, 3H), δ 2.00-2.09 (m, 4H), δ 1.37 (s, 9H).

4-[4-(6-Fluoro-pyrido[3,4-d]pyrimidin-4-ylamino)-2-methyl-phenoxy]-benzoic acid tert-butyl ester: The title compound was prepared from 6-Fluoro-3H-pyrido[3,4-d]pyrimidin-4-one and 4-(4-Amino-2-methyl-phenoxy)-benzoic acid tert-butyl ester by a procedure analogous to the synthesis of 3-[4-(6-Fluoro-pyrido[3,4-d]pyrimidin-4-ylamino)-2-methyl-phenoxy]-benzoic acid tert-butyl ester above. LRMS: 447.3/391.2 (MH+); $^1$H NMR (DMSO-$d_6$, 400 MHz): δ 10.03 (s, 1H), δ 8.90 (s, 1H), δ 8.65 (s, 1H), δ 8.24 (s, 1H), δ 7.75-7.87 (m, 4H), δ 7.07 (d, J=8.73, 1H), δ 6.90-6.93 (m, 2H), δ 2.12 (s, 3H), δ 1.49 (s, 9H).

4-[2-Methyl-4-(6-morpholin-4-yl-pyrido[3,4-d]pyrimidin-4-ylamino)-phenoxy]-benzoic acid tert-butyl ester: The title compound was prepared from 4-[4-(6-Fluoro-pyrido[3,4-d]pyrimidin-4-ylamino)-2-methyl-phenoxy]-benzoic acid tert-butyl ester and morpholine by a procedure analogous to the synthesis of [3-Methyl-4-(piperidin-4-yloxy)-phenyl]-(6-morpholin-4-yl-pyrido[3,4-d]pyrimidin-4-yl)-amine. LRMS: 498.4 (MH+). $^1$H NMR (DMSO-$d_6$, 400 MHz): δ 9.74 (s, 1H), δ 8.87 (s, 1H), δ 8.45 (s, 1H), δ 7.89-7.92 (m, 2H), δ 7.80-δ 7.83 (m, 2H), δ 7.55 (s, 1H), δ 7.12 (d, J=9.64, 1H), δ 6.95-6.98 (m, 2H), δ 3.80-3.83 (m, 4H), δ 3.58-δ 3.61 (m, 4H), δ 2.17 (s, 3H), δ 1.54 (s, 9H).

4-[2-Methyl-4-(6-morpholin-4-yl-pyrido[3,4-d]pyrimidin-4-ylamino)-phenoxy]-benzoic acid: The title compound was prepared from 4-[2-Methyl-4-(6-morpholin-4-yl-pyrido[3,4-d]pyrimidin-4-ylamino)-phenoxy]-benzoic acid tert-butyl ester by a procedure analogous to the synthesis of 3-[2-Methyl-4-(6-pyrrolidin-1-yl-pyrido[3,4-d]pyrimidin-4-ylamino phenoxy]-benzoic acid. LRMS: 458.3 (MH+) HPLC Rf: 5.94 min.

N-tert-Butyl-4-[2-methyl-4-(6-morpholin-4-yl-pyrido[3,4-d]pyrimidin-4-ylamino)-phenoxy]-benzamide: The title compound was prepared from 4-[2-Methyl-4-(6-morpholin-4-yl-pyrido[3,4-d]pyrimidin-4-ylamino)-phenoxy]-benzoic acid and tert-butyl amine by a procedure analogous to the synthesis of N-tert-Butyl-3-[2-methyl-4-(6-pyrrolidin-1-yl-pyrido[3,4-d]pyrimidin-4-ylamino)-phenoxy]-benzamide. LRMS: 513.4 (MH+); $^1$H NMR (DMSO-$d_6$, 400 MHz): δ 9.77 (s, 1H), δ 8.83 (s, 1H), δ 8.42 (s, 1H), δ 7.72-7.78 (m, 4H), δ 7.63 (s, 1H), δ 7.51 (s, 1H), δ 7.03 (d, J=9.14, 1H), δ 6.87 (d, J=8.72, 2H), δ 3.75-3.77 (m, 4H), δ 3.54-3.56 (m, 4H), δ 2.14 (s, 3H), δ 1.33 (s, 9H).

The following examples were prepared using the methods described above. HPLC method A refers to the following conditions: A Polaris 5 micron C18-A 20×2.0 mm column made by Metachem Technologies is utilized with a 1 mL/min. flow rate, and the following solvent gradient:

| Solvent A/B | Time (min.) |
|---|---|
| 95/5 | 0 min. |
| 80/20 | 1.25 |
| 50/50 | 2.50 |
| 0/100 | 3.75 |
| 0/100 | 4.10 (finished) |

Solvent A contains a mixture of 94.952% water and 4.998% acetonitrile with 0.05% formic acid, and solvent B contains acetonitrile with 0.05% formic acid.

HPLC method B refers to the following conditions: The column used is a ZORBAX™ RXC18 column (manufactured by Hewlett Packard) of 150 mm distance and 4.6 mm interior diameter. The samples are run on a Hewlett Packard-1100 system. A gradient solvent method is used running 100 percent aqueous ammonium acetate/acetic acid buffer (0.2 M) to 70 percent acetonitrile over 10 minutes. The gradient then continues to 90% acetonitrile after 20 minutes. The system then proceeds on a wash cycle with 100 percent acetonitrile for 1.5 minutes and then 100 percent buffer solution for 3 minutes. The flow rate over this period is a constant 3 mL/minute.

HPLC method C refers to the following conditions: A Symmetry C8 reverse phase 19×50 mm column is used with a 5 µm pore size. The flow rate is 25 mL/min. and a linear column gradient of 5% acetonitrile/water to 100% acetonitrile, always with 0.1% formic acid present is used with a 15 min. total run time.

The following examples were prepared using the methods described above.

TABLE I

| Example No. | Preparation Method (Scheme No.) | Name | LRMS (MH+) | HPLC retention time (min) | HPLC Method |
|---|---|---|---|---|---|
| 8. | 5 | Cyclobutyl-{4-[4-(6-methoxy-quinazolin-4-ylamino)-2-methyl-phenoxy]-piperidin-1-yl}-methanone | 447.1 | 8.512 | B |
| 9. | 5 | 4-[4-(6-Methoxy-quinazolin-4-ylamino)-2-methyl-phenoxy]-piperidine-1-carboxylic acid (2,6-difluoro-phenyl)-amide | 520.5 | 8.190 | B |
| 10. | 5 | 1-{4-[4-(6-Methoxy-quinazolin-4-ylamino)-2-methyl-phenoxy]-piperidin-1-yl}-3,3-dimethyl-butan-1-one | 463.5 | 9.256 | B |
| 11. | 5 | 2-Cyclopropyl-1-{4-[4-(6-methoxy-quinazolin-4-ylamino)-2-methyl-phenoxy]-piperidin-1-yl}-ethanone | 447.5 | 8.120 | B |
| 12. | 5 | 4-[4-(6-Methoxy-quinazolin-4-ylamino)-2-methyl-phenoxy]-piperidine-1-carboxylic acid tert-butyl-amide | 464.5 | 8.490 | B |
| 13. | 5 | 4-[4-(6-Methoxy-quinazolin-4-ylamino)-2-methyl-phenoxy]-piperidine-1-carboxylic acid cyclopentylamide | 476.5 | 8.381 | B |
| 14. | 5 | 4-[4-(6-Methoxy-quinazolin-4-ylamino)-2-methyl-phenoxy]-piperidine-1-carboxylic acid (4-methoxy-phenyl)-amide | 514.5 | 8.306 | B |
| 15. | 5 | 4-[4-(6,7-Dimethoxy-quinazolin-4-ylamino)-2-methyl-phenoxy]-piperidine-1-carboxylic acid (2,6-difluoro-phenyl)-amide | 550.4 | 5.26 | A |
| 16. | 5 | 4-[4-(6,7-Dimethoxy-quinazolin-4-ylamino)-2-methyl-phenoxy]-piperidine-1-carboxylic acid (4-methoxy-phenyl)-amide | 544.5 | 1.8 | A |
| 17. | 5 | {4-[4-(6,7-Dimethoxy-quinazolin-4-ylamino)-2-methyl-phenoxy]-piperidin-1-yl}-morpholin-4-yl-methanone | 508.5 | 1.7 | A |
| 18. | 5 | 4-[4-(6,7-Dimethoxy-quinazolin-4-ylamino)-2-methyl-phenoxy]-piperidine-1-carboxylic acid (2,5-difluoro-phenyl)-amide | 550.4 | 2.0 | A |
| 19. | 5 | 4-[4-(6,7-Dimethoxy-quinazolin-4-ylamino)-2-methyl-phenoxy]-piperidine-1-carboxylic acid cyclopentylamide | 506.5 | 1.9 | A |
| 20. | 5 | 1-{4-[4-(6,7-Dimethoxy-quinazolin-4-ylamino)-2-methyl-phenoxy]-piperidin-1-yl}-3,3-dimethyl-butan-1-one | 493.5 | 2.0 | A |
| 21. | 5 | {4-[4-(6,7-Dimethoxy-quinazolin-4-ylamino)-2-methyl-phenoxy]-piperidin-1-yl}-(3-methoxy-phenyl)-methanone | 529.5 | 2.0 | A |
| 22. | 5 | Cyclopentyl-{4-[4-(6,7-dimethoxy-quinazolin-4-ylamino)-2-methyl-phenoxy]-piperidin-1-yl}-methanone | 491.5 | 2.0 | A |

TABLE I-continued

| Example No. | Preparation Method (Scheme No.) | Name | LRMS (MH+) | HPLC retention time (min) | HPLC Method |
|---|---|---|---|---|---|
| 23. | 5 | 2-Cyclopentyl-1-{4-[4-(6,7-dimethoxy-quinazolin-4-ylamino)-2-methyl-phenoxy]-piperidin-1-yl}-ethanone | 505.5 | 2.0 | A |
| 24. | 5 | {4-[4-(6,7-Dimethoxy-quinazolin-4-ylamino)-2-methyl-phenoxy]-piperidin-1-yl}-(tetrahydro-furan-2-yl)-methanone | 493.5 | 1.7 | A |
| 25. | 5 | 4-[4-(6,7-Dimethoxy-quinazolin-4-ylamino)-2-methyl-phenoxy]-N-(2,2-dimethyl-propyl)-benzamide | 501.4 | 2.1 | A |
| 26. | 5 | 4-[4-(6,7-Dimethoxy-quinazolin-4-ylamino)-2-methyl-phenoxy]-N-pentyl-benzamide | 501.4 | 2.1 | A |
| 27. | 5 | N-Cyclohexyl-4-[4-(6,7-dimethoxy-quinazolin-4-ylamino)-2-methyl-phenoxy]-benzamide | 513.4 | 2.1 | A |
| 28. | 5 | 4-[4-(6,7-Dimethoxy-quinazolin-4-ylamino)-2-methyl-phenoxy]-N-(4-methoxy-phenyl)-benzamide | 537.4 | 2.1 | A |
| 29. | 5 | 4-[4-(6,7-Dimethoxy-quinazolin-4-ylamino)-2-methyl-phenoxy]-N-(2-fluoro-phenyl)-benzamide | 525.4 | 2.1 | A |
| 30. | 5 | {4-[4-(6,7-Dimethoxy-quinazolin-4-ylamino)-2-methyl-phenoxy]-phenyl}-piperidin-1-yl-methanone | 499.4 | 2.0 | A |
| 31. | 5 | 4-[4-(6,7-Dimethoxy-quinazolin-4-ylamino)-2-methyl-phenoxy]-N-(2-piperidin-1-yl-ethyl)-benzamide | 542.5 | 1.3 | A |
| 32. | 5 | 3-[4-(6,7-Dimethoxy-quinazolin-4-ylamino)-2-methyl-phenoxy]-N-(2,2-dimethyl-propyl)-benzamide | 501.5 | 2.1 | A |
| 33. | 5 | 3-[4-(6,7-Dimethoxy-quinazolin-4-ylamino)-2-methyl-phenoxy]-N-pentyl-benzamide | 501.5 | 2.2 | A |
| 34. | 5 | N-Cyclohexyl-3-[4-(6,7-dimethoxy-quinazolin-4-ylamino)-2-methyl-phenoxy]-benzamide | 513.5 | 2.1 | A |
| 35. | 5 | 3-[4-(6,7-Dimethoxy-quinazolin-4-ylamino)-2-methyl-phenoxy]-N-(4-methoxy-phenyl)-benzamide | 537.5 | 2.1 | A |
| 36. | 5 | 3-[4-(6,7-Dimethoxy-quinazolin-4-ylamino)-2-methyl-phenoxy]-N-(2-fluoro-phenyl)-benzamide | 525.5 | 2.1 | A |
| 37. | 5 | {3-[4-(6,7-Dimethoxy-quinazolin-4-ylamino)-2-methyl-phenoxy]-phenyl}-piperidin-1-yl-methanone | 499.5 | 2.0 | A |
| 38. | 5 | 3-[4-(6,7-Dimethoxy-quinazolin-4-ylamino)-2-methyl-phenoxy]-N-(2-piperidin-1-yl-ethyl)-benzamide | 542.5 | 1.3 | A |
| 39. | 5 | 3-[4-(6,7-Dimethoxy-quinazolin-4-ylamino)-2-methyl-phenoxy]-N-(1,1-dimethyl-propyl)-benzamide | 501.2 | 2.0 | A |
| 40. | 5 | 4-[4-(6,7-Dimethoxy-quinazolin-4-ylamino)-2-methyl-phenoxy]-N-(1,1-dimethyl-propyl)-benzamide | 501.2 | 1.9 | A |

TABLE I-continued

| Example No. | Preparation Method (Scheme No.) | Name | LRMS (MH+) | HPLC retention time (min) | HPLC Method |
|---|---|---|---|---|---|
| 41. | 5 | 4-[4-(6,7-Dimethoxy-quinazolin-4-ylamino)-2-methyl-phenoxy]-piperidine-1-carboxylic acid o-tolyl-amide | 528.2 | 1.7 | A |
| 42. | 5 | 4-[4-(6,7-Dimethoxy-quinazolin-4-ylamino)-2-methyl-phenoxy]-piperidine-1-carboxylic acid (4-chloro-phenyl)-amide | 548.1 | 1.9 | A |
| 43. | 5 | 4-[4-(6,7-Dimethoxy-quinazolin-4-ylamino)-2-methyl-phenoxy]-piperidine-1-carboxylic acid (2-chloro-phenyl)-amide | 548.1 | 1.8 | A |
| 44. | 5 | 4-[4-(6,7-Dimethoxy-quinazolin-4-ylamino)-2-methyl-phenoxy]-piperidine-1-carboxylic acid (2-methoxy-phenyl)-amide | 544.1 | 1.8 | A |
| 45. | 5 | 4-[4-(6,7-Dimethoxy-quinazolin-4-ylamino)-2-methyl-phenoxy]-piperidine-1-carboxylic acid (2-fluoro-phenyl)-amide | 532.2 | 1.8 | A |
| 46. | 5 | 4-[4-(6,7-Dimethoxy-quinazolin-4-ylamino)-2-methyl-phenoxy]-piperidine-1-carboxylic acid (4-fluoro-phenyl)-amide | 532.1 | 1.8 | A |
| 47. | 5 | 4-[4-(6,7-Dimethoxy-quinazolin-4-ylamino)-2-methyl-phenoxy]-piperidine-1-carboxylic acid (3-trifluoromethyl-phenyl)-amide | 582.1 | 2.0 | A |
| 48. | 5 | 4-[4-(6,7-Dimethoxy-quinazolin-4-ylamino)-2-methyl-phenoxy]-piperidine-1-carboxylic acid (2,5-difluoro-phenyl)-amide | 550.1 | 1.7 | A |
| 49. | 5 | 4-[4-(6,7-Dimethoxy-quinazolin-4-ylamino)-2-methyl-phenoxy]-piperidine-1-carboxylic acid (3-fluoro-phenyl)-amide | 532.1 | 1.6 | A |
| 50. | 5 | 4-[4-(6,7-Dimethoxy-quinazolin-4-ylamino)-2-methyl-phenoxy]-piperidine-1-carboxylic acid (2-trifluoromethyl-phenyl)-amide | 582.0 | 1.8 | A |
| 51. | 5 | 4-[4-(6,7-Dimethoxy-quinazolin-4-ylamino)-2-methyl-phenoxy]-piperidine-1-carboxylic acid (2,6-dichloro-phenyl)-amide | 582.0 | 1.7 | A |
| 52. | 5 | 4-[4-(6,7-Dimethoxy-quinazolin-4-ylamino)-2-methyl-phenoxy]-piperidine-1-carboxylic acid (4-trifluoromethyl-phenyl)-amide | 582.0 | 2.0 | A |
| 53. | 5 | 4-[4-(6,7-Dimethoxy-quinazolin-4-ylamino)-2-methyl-phenoxy]-piperidine-1-carboxylic acid (2,6-dimethyl-phenyl)-amide | 542.5 | 1.9 | A |
| 54. | 5 | 4-[4-(6,7-Dimethoxy-quinazolin-4-ylamino)-2-methyl-phenoxy]-piperidine-1-carboxylic acid (4-dimethylamino-phenyl)-amide | 557.1 | 1.3 | A |
| 55. | 5 | 4-[4-(6,7-Dimethoxy-quinazolin-4-ylamino)-2-methyl-phenoxy]-piperidine-1-carboxylic acid (3,5-difluoro-phenyl)-amide | 550.4 | 2.1 | A |

TABLE I-continued

| Example No. | Preparation Method (Scheme No.) | Name | LRMS (MH+) | HPLC retention time (min) | HPLC Method |
|---|---|---|---|---|---|
| 56. | 6 | Cyclopentyl-{4-[2-methyl-4-(6-pyrrolidin-1-yl-pyrido[3,4-d]pyrimidin-4-ylamino)-phenoxy]-piperidin-1-yl}-methanone | 501.9 | 10.64 | B |
| 57. | 6 | Cyclopentyl-(4-{2-methyl-4-[6-(4-methyl-piperazin-1-yl)-pyrido[3,4-d]pyrimidin-4-ylamino]-phenoxy}-piperidin-1-yl)-methanone | 530.5 | 6.92 | B |
| 58. | 6 | Cyclopentyl-{4-[4-(6-dimethylamino-pyrido[3,4-d]pyrimidin-4-ylamino)-2-methyl-phenoxy]-piperidin-1-yl}-methanone | 475.4 | 9.71 | B |
| 59. | 7 | 3-[2-Methyl-4-(6-morpholin-4-yl-pyrido[3,4-d]pyrimidin-4-ylamino)-phenoxy]-benzoic acid tert-butyl ester | 514.3 | 11.86 | B |
| 60. | 7 | 3-{2-Methyl-4-[6-(2-morpholin-4-yl-ethylamino)-pyrido[3,4-d]pyrimidin-4-ylamino]-phenoxy}-benzoic acid tert-butyl ester | 557.3 | 10.54 | B |
| 61. | 7 | 3-{2-Methyl-4-[6-(4-methyl-piperazin-1-yl)-pyrido[3,4-d]pyrimidin-4-ylamino]-phenoxy)-benzoic acid tert-butyl ester | 527.3 | 9.55 | B |
| 62. | 7 | 3-[2-Methyl-4-(6-pyrrolidin-1-yl-pyrido[3,4-d]pyrimidin-4-ylamino)-phenoxy]-benzoic acid tert-butyl ester | 498.3 | 14.43 | B |
| 63. | 6 | Cyclopentyl-{4-[2-methyl-4-(6-morpholin-4-yl-pyrido[3,4-d]pyrimidin-4-ylamino)-phenoxy]-piperidin-1-yl}-methanone | 517.4 | 9.14 | B |
| 64. | 7 | N-Cyclohexyl-3-[4-(6-dimethylamino-pyrido[3,4-d]pyrimidin-4-ylamino)-2-methyl-phenoxy]-benzamide | 497.4 | 10.42 | B |
| 65. | 7 | 3-[4-(6-Dimethylamino-pyrido[3,4-d]pyrimidin-4-ylamino)-2-methyl-phenoxy]-N-(2,2-dimethyl-propyl)-benzamide | 485.4 | 10.26 | B |
| 66. | 6 | 2-Cyclopentyl-1-{4-[4-(6-dimethylamino-pyrido[3,4-d]pyrimidin-4-ylamino)-2-methyl-phenoxy]-piperidin-1-yl}-ethanone | 489.4 | 10.13 | B |
| 67. | 6 | 4-[2-Methyl-4-(6-morpholin-4-yl-pyrido[3,4-d]pyrimidin-4-ylamino)-phenoxy]-piperidine-1-carboxylic acid (2,6-difluoro-phenyl)-amide | 576.4 | 8.25 | B |
| 68. | 6 | 4-{2-Methyl-4-[6-(4-methyl-piperazin-1-yl)-pyrido[3,4-d]pyrimidin-4-ylamino]-phenoxy}-piperidine-1-carboxylic acid (2,6-difluoro-phenyl)-amide | 589.4 | 6.30 | B |
| 69. | 6 | 4-[4-(6-Dimethylamino-pyrido[3,4-d]pyrimidin-4-ylamino)-2-methyl-phenoxy]-piperidine-1-carboxylic acid (2,6-difluoro-phenyl)-amide | 534.3 | 8.74 | B |
| 70. | 6 | 4-[2-Methyl-4-(6-pyrrolidin-1-yl-pyrido[3,4-d]pyrimidin-4-ylamino)-phenoxy]-piperidine-1-carboxylic acid (2,6-difluoro-phenyl)-amide | 534.3 | 8.74 | B |

TABLE I-continued

| Example No. | Preparation Method (Scheme No.) | Name | LRMS (MH+) | HPLC retention time (min) | HPLC Method |
|---|---|---|---|---|---|
| 71. | 6 | Cyclopentyl-(4-{2-methyl-4-[6-(2-morpholin-4-yl-ethylamino)-pyrido[3,4-d]pyrimidin-4-ylamino]-phenoxy}-piperidin-1-yl)-methanone | 560.4 | 7.2 | B |
| 72. | 6 | 2-Cyclopentyl-1-{4-[2-methyl-4-(6-morpholin-4-yl-pyrido[3,4-d]pyrimidin-4-ylamino)-phenoxy]-piperidin-1-yl}-ethanone | 531.4 | 9.57 | B |
| 73. | 6 | 2-Cyclopentyl-1-(4-{2-methyl-4-[6-(4-methyl-piperazin-1-yl)-pyrido[3,4-d]pyrimidin-4-ylamino]-phenoxy}-piperidin-1-yl)-ethanone | 544.4 | 7.50 | B |
| 74. | 6 | 2-Cyclopentyl-1-{4-[2-methyl-4-(6-pyrrolidin-1-yl-pyrido[3,4-d]pyrimidin-4-ylamino)-phenoxy]-piperidin-1-yl}-ethanone | 515.4 | 11.2 | B |
| 75. | 6 | 2-Cyclopentyl-1-(4-{2-methyl-4-[6-(2-morpholin-4-yl-ethylamino)-pyrido[3,4-d]pyrimidin-4-ylamino]-phenoxy}-piperidin-1-yl)-ethanone | 574.4 | 7.69 | B |
| 76. | 7 | N-(2-Fluoro-phenyl)-3-[2-methyl-4-(6-morpholin-4-yl-pyrido[3,4-d]pyrimidin-4-ylamino)-phenoxy]-benzamide | 551.3 | 9.7 | B |
| 77. | 7 | N-Cyclohexyl-3-[2-methyl-4-(6-morpholin-4-yl-pyrido[3,4-d]pyrimidin-4-ylamino)-phenoxy]-benzamide | 539.4 | 9.85 | B |
| 78. | 7 | N-tert-Butyl-3-[2-methyl-4-(6-morpholin-4-yl-pyrido[3,4-d]pyrimidin-4-ylamino)-phenoxy]-benzamide | 513.4 | 9.56 | B |
| 79. | 7 | N-(1,1-Dimethyl-propyl)-3-[2-methyl-4-(6-morpholin-4-yl-pyrido[3,4-d]pyrimidin-4-ylamino)-phenoxy]-benzamide | 527.4 | 10.05 | B |
| 80. | 7 | N-(2,2-Dimethyl-propyl)-3-[2-methyl-4-(6-morpholin-4-yl-pyrido[3,4-d]pyrimidin-4-ylamino)-phenoxy]-benzamide | 527.3 | 9.73 | B |
| 81. | 7 | N-Cyclohexyl-3-{2-methyl-4-[6-(2-morpholin-4-yl-ethylamino)-pyrido[3,4-d]pyrimidin-4-ylamino]-phenoxy}-benzamide | 582.4 | 8.26 | B |
| 82. | 7 | 4-[4-(6-Dimethylamino-pyrido[3,4-d]pyrimidin-4-ylamino)-2-methyl-phenoxy]-benzoic acid tert-butyl ester | 472.4 | 12.85 | B |
| 83. | 7 | 4-[2-Methyl-4-(6-morpholin-4-yl-pyrido[3,4-d]pyrimidin-4-ylamino)-phenoxy]-benzoic acid tert-butyl ester | 514.3 | 11.29 | B |
| 84. | 7 | 4-{2-Methyl-4-[6-(2-morpholin-4-yl-ethylamino)-pyrido[3,4-d]pyrimidin-4-ylamino]-phenoxy}-benzoic acid tert-butyl ester | 557.3 | 10.57 | B |
| 85. | 7 | 4-{2-Methyl-4-[6-(4-methyl-piperazin-1-yl)-pyrido[3,4-d]pyrimidin-4-ylamino]-phenoxy}-benzoic acid tert-butyl ester | 527.4 | 9.83 | B |
| 86. | 7 | 4-[2-Methyl-4-(6-pyrrolidin-1-yl-pyrido[3,4-d]pyrimidin-4-ylamino)-phenoxy]-benzoic acid tert-butyl ester | 498.4 | 14.40 | B |

TABLE I-continued

| Example No. | Preparation Method (Scheme No.) | Name | LRMS (MH+) | HPLC retention time (min) | HPLC Method |
|---|---|---|---|---|---|
| 87. | 7 | N-tert-Butyl-3-{2-methyl-4-[6-(2-morpholin-4-yl-ethylamino)-pyrido[3,4-d]pyrimidin-4-ylamino]-phenoxy}-benzamide | 556.2 | 7.79 | B |
| 88. | 7 | N-(2-Fluoro-phenyl)-3-{2-methyl-4-[6-(2-morpholin-4-yl-ethylamino)-pyrido[3,4-d]pyrimidin-4-ylamino]-phenoxy}-benzamide | 594.2 | 8.11 | B |
| 89. | 7 | N-(1,1-Dimethyl-propyl)-3-{2-methyl-4-[6-(2-morpholin-4-yl-ethylamino)-pyrido[3,4-d]pyrimidin-4-ylamino]-phenoxy}-benzamide | 570.2 | 8.34 | B |
| 90. | 7 | N-(2,2-Dimethyl-propyl)-3-{2-methyl-4-[6-(2-morpholin-4-yl-ethylamino)-pyrido[3,4-d]pyrimidin-4-ylamino]-phenoxy}-benzamide | 570.3 | 8.02 | B |
| 91. | 7 | N-Cyclohexyl-3-{2-methyl-4-[6-(4-methyl-piperazin-1-yl)-pyrido[3,4-d]pyrimidin-4-ylamino]-phenoxy}-benzamide | 552.3 | 7.83 | B |
| 92. | 7 | N-tert-Butyl-3-{2-methyl-4-[6-(4-methyl-piperazin-1-yl)-pyrido[3,4-d]pyrimidin-4-ylamino]-phenoxy}-benzamide | 526.3 | 7.47 | B |
| 93. | 7 | N-(2-Fluoro-phenyl)-3-{2-methyl-4-[6-(4-methyl-piperazin-1-yl)-pyrido[3,4-d]pyrimidin-4-ylamino]-phenoxy}-benzamide | 564.2 | 7.71 | B |
| 94. | 7 | N-(1,1-Dimethyl-propyl)-3-{2-methyl-4-[6-(4-methyl-piperazin-1-yl)-pyrido[3,4-d]pyrimidin-4-ylamino]-phenoxy}-benzamide | 540.2 | 7.93 | B |
| 95. | 7 | N-(2,2-Dimethyl-propyl)-3-{2-methyl-4-[6-(4-methyl-piperazin-1-yl)-pyrido[3,4-d]pyrimidin-4-ylamino]-phenoxy}-benzamide | 540.3 | 7.7/8.0 | B |
| 96. | 7 | N-Cyclohexyl-3-[2-methyl-4-(6-pyrrolidin-1-yl-pyrido[3,4-d]pyrimidin-4-ylamino)-phenoxy]-benzamide | 523.3 | 11.31 | B |
| 97. | 7 | N-tert-Butyl-3-[2-methyl-4-(6-pyrrolidin-1-yl-pyrido[3,4-d]pyrimidin-4-ylamino)-phenoxy]-benzamide | 497.3 | 8.86 | B |
| 98. | 7 | N-(2-Fluoro-phenyl)-3-[2-methyl-4-(6-pyrrolidin-1-yl-pyrido[3,4-d]pyrimidin-4-ylamino)-phenoxy]-benzamide | 535.2 | 11.11 | B |
| 99. | 7 | N-(1,1-Dimethyl-propyl)-3-[2-methyl-4-(6-pyrrolidin-1-yl-pyrido[3,4-d]pyrimidin-4-ylamino)-phenoxy]-benzamide | 511.2 | 11.57 | B |
| 100. | 7 | N-(2,2-Dimethyl-propyl)-3-[2-methyl-4-(6-pyrrolidin-1-yl-pyrido[3,4-d]pyrimidin-4-ylamino)-phenoxy]-benzamide | 511.3 | 11.12 | B |
| 101. | 7 | N-Cyclohexyl-4-[2-methyl-4-(6-morpholin-4-yl-pyrido[3,4-d]pyrimidin-4-ylamino)-phenoxy]-benzamide | 539.3 | 9.73 | B |
| 102. | 7 | N-(2-Fluoro-phenyl)-4-[2-methyl-4-(6-morpholin-4-yl-pyrido[3,4-d]pyrimidin-4-ylamino)-phenoxy]-benzamide | 551.3 | 9.68 | B |
| 103. | 7 | N-tert-Butyl-4-[2-methyl-4-(6-morpholin-4-yl-pyrido[3,4-d]pyrimidin-4-ylamino)-phenoxy]-benzamide | 513.4 | 9.39 | B |

TABLE I-continued

| Example No. | Preparation Method (Scheme No.) | Name | LRMS (MH+) | HPLC retention time (min) | HPLC Method |
|---|---|---|---|---|---|
| 104. | 7 | N-(1,1-Dimethyl-propyl)-4-[2-methyl-4-(6-morpholin-4-yl-pyrido[3,4-d]pyrimidin-4-ylamino)-phenoxy]-benzamide | 527.3 | 9.89 | B |
| 105. | 7 | N-(2,2-Dimethyl-propyl)-4-[2-methyl-4-(6-morpholin-4-yl-pyrido[3,4-d]pyrimidin-4-ylamino)-phenoxy]-benzamide | 527.3 | 9.60 | B |
| 106. | 7 | N-Cyclohexyl-4-[4-(6-dimethylamino-pyrido[3,4-d]pyrimidin-4-ylamino)-2-methyl-phenoxy]-benzamide | 497.2 | 10.26 | B |
| 107. | 7 | 4-[4-(6-Dimethylamino-pyrido[3,4-d]pyrimidin-4-ylamino)-2-methyl-phenoxy]-N-(2-fluoro-phenyl)-benzamide | 509.1 | 10.23 | B |
| 108. | 7 | N-tert-Butyl-4-[4-(6-dimethylamino-pyrido[3,4-d]pyrimidin-4-ylamino)-2-methyl-phenoxy]-benzamide | 471.2 | 9.89 | B |
| 109. | 7 | 4-[4-(6-Dimethylamino-pyrido[3,4-d]pyrimidin-4-ylamino)-2-methyl-phenoxy]-N-(1,1-dimethyl-propyl)-benzamide | 485.2 | 10.40 | B |
| 110. | 7 | 4-[4-(6-Dimethylamino-pyrido[3,4-d]pyrimidin-4-ylamino)-2-methyl-phenoxy]-N-(2,2-dimethyl-propyl)-benzamide | 485.2 | 10.12 | B |
| 111. | 7 | N-Cyclohexyl-4-{2-methyl-4-[6-(2-morpholin-4-yl-ethylamino)-pyrido[3,4-d]pyrimidin-4-ylamino]-phenoxy}-benzamide | 582.2 | 8.20 | B |
| 112. | 7 | N-(2-Fluoro-phenyl)-4-{2-methyl-4-[6-(2-morpholin-4-yl-ethylamino)-pyrido[3,4-d]pyrimidin-4-ylamino]-phenoxy}-benzamide | 594.2 | 8.2 | B |
| 113. | 7 | N-tert-Butyl-4-{2-methyl-4-[6-(2-morpholin-4-yl-ethylamino)-pyrido[3,4-d]pyrimidin-4-ylamino]-phenoxy}-benzamide | 556.2 | 7.8 | B |
| 114. | 7 | N-(1,1-Dimethyl-propyl)-4-{2-methyl-4-[6-(2-morpholin-4-yl-ethylamino)-pyrido[3,4-d]pyrimidin-4-ylamino]-phenoxy}-benzamide | 570.2 | 8.4 | B |
| 115. | 7 | N-(2,2-Dimethyl-propyl)-4-{2-methyl-4-[6-(2-morpholin-4-yl-ethylamino)-pyrido[3,4-d]pyrimidin-4-ylamino]-phenoxy}-benzamide | 570.2 | 8.1 | B |
| 116. | 7 | N-Cyclohexyl-4-{2-methyl-4-[6-(4-methyl-piperazin-1-yl)-pyrido[3,4-d]pyrimidin-4-ylamino]-phenoxy}-benzamide | 552.4 | 7.9 | B |
| 117. | 7 | N-(2-Fluoro-phenyl)-4-{2-methyl-4-[6-(4-methyl-piperazin-1-yl)-pyrido[3,4-d]pyrimidin-4-ylamino]-phenoxy}-benzamide | 564.3 | 7.7 | B |
| 118. | 7 | N-tert-Butyl-4-{2-methyl-4-[6-(4-methyl-piperazin-1-yl)-pyrido[3,4-d]pyrimidin-4-ylamino]-phenoxy}-benzamide | 526.3 | 7.4 | B |
| 119. | 7 | N-(1,1-Dimethyl-propyl)-4-{2-methyl-4-[6-(4-methyl-piperazin-1-yl)-pyrido[3,4-d]pyrimidin-4-ylamino]-phenoxy}-benzamide | 540.3 | 8.0 | B |

TABLE I-continued

| Example No. | Preparation Method (Scheme No.) | Name | LRMS (MH+) | HPLC retention time (min) | HPLC Method |
|---|---|---|---|---|---|
| 120. | 7 | N-(2,2-Dimethyl-propyl)-4-{2-methyl-4-[6-(4-methyl-piperazin-1-yl)-pyrido[3,4-d]pyrimidin-4-ylamino]-phenoxy}-benzamide | 540.3 | 7.6 | B |
| 121. | 7 | N-Cyclohexyl-4-[2-methyl-4-(6-pyrrolidin-1-yl-pyrido[3,4-d]pyrimidin-4-ylamino)-phenoxy}-benzamide | 523.3 | 11.14 | B |
| 122. | 7 | N-(2-Fluoro-phenyl)-4-[2-methyl-4-(6-pyrrolidin-1-yl-pyrido[3,4-d]pyrimidin-4-ylamino)-phenoxy]-benzamide | 535.2 | 11.12 | B |
| 123. | 7 | N-tert-Butyl-4-[2-methyl-4-(6-pyrrolidin-1-yl-pyrido[3,4-d]pyrimidin-4-ylamino)-phenoxy]-benzamide | 497.3 | 10.75 | B |
| 124. | 7 | N-(1,1-Dimethyl-propyl)-4-[2-methyl-4-(6-pyrrolidin-1-yl-pyrido[3,4-d]pyrimidin-4-ylamino)-phenoxy]-benzamide | 511.3 | 11.33 | B |
| 125. | 7 | N-(2,2-Dimethyl-propyl)-4-[2-methyl-4-(6-pyrrolidin-1-yl-pyrido[3,4-d]pyrimidin-4-ylamino)-phenoxy]-benzamide | 511.2 | 10.95 | B |
| 126. | 6 | [3-Methyl-4-(piperidin-4-yloxy)-phenyl]-(6-morpholin-4-yl-pyrido[3,4-d]pyrimidin-4-yl)-amine | 421.3 | 5.2 | B |
| 127. | 6 | Cyclopentyl-{4-[2-methyl-4-(6-methylamino-pyrido[3,4-d]pyrimidin-4-ylamino)-phenoxy]-piperidin-1-yl}-methanone | 461.3 | 8.87 | B |
| 128. | 6 | {4-[2-Methyl-4-(6-morpholin-4-yl-pyrido[3,4-d]pyrimidin-4-ylamino)-phenoxy]-piperidin-1-yl}-morpholin-4-yl-methanone | 534.2 | 7.43 | B |
| 129. | 6 | {4-[2-Methyl-4-(6-morpholin-4-yl-pyrido[3,4-d]pyrimidin-4-ylamino)-phenoxy]-piperidin-1-yl}-(tetrahydro-furan-2-yl)-methanone | 570.3 | 7.3 | B |
| 130. | 6 | 4-[2-Methyl-4-(6-morpholin-4-yl-pyrido[3,4-d]pyrimidin-4-ylamino)-phenoxy]-piperidine-1-carboxylic acid (4-methoxy-phenyl)-amide | 570.3 | 8.30 | B |
| 131. | 6 | (3-Methoxy-phenyl)-{4-[2-methyl-4-(6-morpholin-4-yl-pyrido[3,4-d]pyrimidin-4-ylamino)-phenoxy]-piperidin-1-yl}-methanone | 555.2 | 8.74 | B |
| 132. | 6 | 4-[2-Methyl-4-(6-morpholin-4-yl-pyrido[3,4-d]pyrimidin-4-ylamino)-phenoxy]-piperidine-1-carboxylic acid tert-butylamide | 520.3 | 8.55 | B |
| 133. | 6 | 4-[2-Methyl-4-(6-morpholin-4-yl-pyrido[3,4-d]pyrimidin-4-ylamino)-phenoxy]-piperidine-1-carboxylic acid p-tolylamide | 554.2 | 8.99 | B |
| 134. | 6 | 4-[2-Methyl-4-(6-morpholin-4-yl-pyrido[3,4-d]pyrimidin-4-ylamino)-phenoxy]-piperidine-1-carboxylic acid (2,5-difluoro-phenyl)-amide | 576.2 | 9.12 | B |
| 135. | 6 | 2-Dimethylamino-1-{4-[2-methyl-4-(6-morpholin-4-yl-pyrido[3,4-d]pyrimidin-4-ylamino)-phenoxy]-piperidin-1-yl}-ethanone | 506.3 | 5.68 | B |

TABLE I-continued

| Example No. | Preparation Method (Scheme No.) | Name | LRMS (MH+) | HPLC retention time (min) | HPLC Method |
|---|---|---|---|---|---|
| 136. | 6 | 4-[2-Methyl-4-(6-morpholin-4-yl-pyrido[3,4-d]pyrimidin-4-ylamino)-phenoxy]-piperidine-1-carboxylic acid (2,4-difluoro-phenyl)-amide | 576.4 | 10.84 | B |
| 137. | 6 | 4-[2-Methyl-4-(6-morpholin-4-yl-pyrido[3,4-d]pyrimidin-4-ylamino)-phenoxy]-piperidine-1-carboxylic acid cyclopentylamide | 532.3 | 8.45 | B |
| 138. | 6 | 3,3-Dimethyl-1-{4-[2-methyl-4-(6-morpholin-4-yl-pyrido[3,4-d]pyrimidin-4-ylamino)-phenoxy]-piperidin-1-yl}-butan-1-one | 519.3 | 9.30 | B |
| 139. | 6 | 4-[2-Methyl-4-(6-morpholin-4-yl-pyrido[3,4-d]pyrimidin-4-ylamino)-phenoxy]-piperidine-1-carboxylic acid (3,5-difluoro-phenyl)-amide | 576.3 | 9.46 | B |
| 140. | 6 | 4-[4-(6-Dimethylamino-pyrido[3,4-d]pyrimidin-4-ylamino)-2-methyl-phenoxy]-piperidine-1-carboxylic acid tert-butylamide | 478.4 | 9.07 | B |
| 141. | 6 | {4-[4-(6-Dimethylamino-pyrido[3,4-d]pyrimidin-4-ylamino)-2-methyl-phenoxy]-piperidin-1-yl}-(3-methoxy-phenyl)-methanone | 513.3 | 9.35 | B |
| 142. | 6 | 4-[4-(6-Dimethylamino-pyrido[3,4-d]pyrimidin-4-ylamino)-2-methyl-phenoxy]-piperidine-1-carboxylic acid (3,5-difluoro-phenyl)-amide | 534.2 | 10.01 | B |
| 143. | 6 | N,N-6,6-Dimethyl-N-4-[3-methyl-4-(piperidin-4-yloxy)-phenyl]-pyrido[3,4-d]pyrimidine-4,6-diamine | 379.2 | 5.6 | B |
| 144. | 6 | 4-[4-(6-Dimethylamino-pyrido[3,4-d]pyrimidin-4-ylamino)-2-methyl-phenoxy]-piperidine-1-carboxylic acid tert-butyl ester | 479.4 | 10.85 | B |
| 145. | 6 | {4-[4-(6-Dimethylamino-pyrido[3,4-d]pyrimidin-4-ylamino)-2-methyl-phenoxy]-piperidin-1-yl}-morpholin-4-yl-methanone | 492.2 | 7.96 | B |
| 146. | 6 | 4-[4-(6-Dimethylamino-pyrido[3,4-d]pyrimidin-4-ylamino)-2-methyl-phenoxy]-piperidine-1-carboxylic acid (4-methoxy-phenyl)-amide | 528.2 | 8.87 | B |
| 147. | 6 | 4-[4-(6-Dimethylamino-pyrido[3,4-d]pyrimidin-4-ylamino)-2-methyl-phenoxy]-piperidine-1-carboxylic acid cyclopentylamide | 490.2 | 8.94 | B |
| 148. | 6 | 4-[4-(6-Dimethylamino-pyrido[3,4-d]pyrimidin-4-ylamino)-2-methyl-phenoxy]-piperidine-1-carboxylic acid (2,4-difluoro-phenyl)-amide | 534.1 | 9.21 | B |
| 149. | 6 | 4-[4-(6-Dimethylamino-pyrido[3,4-d]pyrimidin-4-ylamino)-2-methyl-phenoxy]-piperidine-1-carboxylic acid p-tolylamide | 512.2 | 9.15 | B |
| 150. | 6 | 4-[4-(6-Dimethylamino-pyrido[3,4-d]pyrimidin-4-ylamino)-2-methyl-phenoxy]-piperidine-1-carboxylic acid (2,5-difluoro-phenyl)-amide | 534.2 | 9.69 | B |

TABLE I-continued

| Example No. | Preparation Method (Scheme No.) | Name | LRMS (MH+) | HPLC retention time (min) | HPLC Method |
|---|---|---|---|---|---|
| 151. | 6 | 1-{4-[4-(6-Dimethylamino-pyrido[3,4-d]pyrimidin-4-ylamino)-2-methyl-phenoxy]-piperidin-1-yl}-3,3-dimethyl-butan-1-one | 477.3 | 9.89 | B |
| 152. | 6 | 4-[4-(6-Dimethylamino-pyrido[3,4-d]pyrimidin-4-ylamino)-2-methyl-phenoxy]-piperidine-1-carboxylic acid (3,5-dichloro-phenyl)-amide | 566.1 | 11.10 | B |
| 153. | 6 | {4-[4-(6-Dimethylamino-pyrido[3,4-d]pyrimidin-4-ylamino)-2-methyl-phenoxy]-piperidin-1-yl}-(tetrahydro-furan-2-yl)-methanone | 477.2 | 7.87 | B |
| 154. | 6 | N-6-Methyl-N-4-[3-methyl-4-(piperidin-4-yloxy)-phenyl]-pyrido[3,4-d]pyrimidine-4,6-diamine | 365.2 | 4.7 | B |
| 155. | 6 | 4-[2-Methyl-4-(6-methylamino-pyrido[3,4-d]pyrimidin-4-ylamino)-phenoxy]-piperidine-1-carboxylic acid (2,6-difluoro-phenyl)-amide | 520.3 | 8.04 | B |
| 156. | 7 | N-(2,2-Dimethyl-propyl)-4-[2-methyl-4-(6-methylamino-pyrido[3,4-d]pyrimidin-4-ylamino)-phenoxy]-benzamide | 471.3 | 9.43 | B |
| 157. | 6 | 4-[2-Chloro-4-(6-methylamino-pyrido[3,4-d]pyrimidin-4-ylamino)-phenoxy]-piperidine-1-carboxylic acid (2,6-difluoro-phenyl)-amide | 540.5 | 2.1 | A |
| 158. | 6 | 4-[2-Chloro-4-(6-dimethylamino-pyirido[3,4-d]pyrimidin-4-ylamino)-phenoxy]-piperidine-1-carboxylic acid (2,6-difluoro-phenyl)-amide | 554.5 | 2 | A |
| 159. | 6 | 4-[4-(6-Azetidin-1-yl-pyrido[3,4-d]pyrimidin-4-ylamino)-2-chloro-phenoxy]-piperidine-1-carboxylic acid (2,6-difluoro-phenyl)-amide | 566.5 | 2.2 | A |
| 160. | 6 | 4-[2-Chloro-4-(6-pyrrolidin-1-yl-pyrido[3,4-d]pyrimidin-4-ylamino)-phenoxy]-piperidine-1-carboxylic acid (2,6-difluoro-phenyl)-amide | 580.0 | 2.3 | A |
| 161. | 6 | 4-[2-Chloro-4-(6-piperidin-1-yl-pyrido[3,4-d]pyrimidin-4-ylamino)-phenoxy]-piperidine-1-carboxylic acid (2,6-difluoro-phenyl)-amide | 594.2 | 2.6 | A |
| 162. | 6 | 4-[4-(6-Dimethylamino-pyrido[3,4-d]pyrimidin-4-ylamino)-2-methoxy-phenoxy]-piperidine-1-carboxylic acid (2,6-difluoro-phenyl)-amide | 550.4 | 1.7 | A |
| 163. | 6 | 4-[4-(6-Azetidin-1-yl-pyrido[3,4-d]pyrimidin-4-ylamino)-2-methoxy-phenoxy]-piperidine-1-carboxylic acid (2,6-difluoro-phenyl)-amide | 562.5 | 2 | A |
| 164. | 6 | 4-{4-[6-(Ethyl-methyl-amino)-pyrido[3,4-d]pyrimidin-4-ylamino]-2-methoxy-phenoxy}-piperidine-1-carboxylic acid (2,6-difluoro-phenyl)-amide | 564.5 | 2.1 | A |
| 165. | 6 | 4-[2-Methoxy-4-(6-pyrrolidin-1-yl-pyrido[3,4-d]pyrimidin-4-ylamino)-phenoxy]-piperidine-1-carboxylic acid (2,6-difluoro-phenyl)-amide | 576.6 | 2.1 | A |

TABLE I-continued

| Example No. | Preparation Method (Scheme No.) | Name | LRMS (MH+) | HPLC retention time (min) | HPLC Method |
|---|---|---|---|---|---|
| 166. | 6 | 4-[2-Methoxy-4-(6-piperidin-1-yl-pyrido[3,4-d]pyrimidin-4-ylamino)-phenoxy]-piperidine-1-carboxylic acid (2,6-difluoro-phenyl)-amide | 590.1 | 2.3 | A |
| 167. | 6 | 4-[2-Methoxy-4-(6-morpholin-4-yl-pyrido[3,4-d]pyrimidin-4-ylamino)-phenoxy]-piperidine-1-carboxylic acid (2,6-difluoro-phenyl)-amide | 592.6 | 2 | A |
| 168. | 6 | {4-[2-Chloro-4-(6-methylamino-pyrido[3,4-d]pyrimidin-4-ylamino)-phenoxy]-piperidin-1-yl}-cyclopentyl-methanone | 481.5 | 2.2 | A |
| 169. | 6 | {4-[2-Chloro-4-(6-dimethylamino-pyrido[3,4-d]pyrimidin-4-ylamino)-phenoxy]-piperidin-1-yl}-cyclopentyl-methanone | 495.5 | 2.3 | A |
| 170. | 6 | {4-[4-(6-Azetidin-1-yl-pyrido[3,4-d]pyrimidin-4-ylamino)-2-chloro-phenoxy]-piperidin-1-yl}-cyclopentyl-methanone | 507.5 | 2.4 | A |
| 171. | 6 | {4-[2-Chloro-4-(6-cyclopropylamino-pyrido[3,4-d]pyrimidin-4-ylamino)-phenoxy]-piperidin-1-yl}-cyclopentyl-methanone | 507.5 | 2.4 | A |
| 172. | 6 | (4-{2-Chloro-4-[6-(ethyl-methyl-amino)-pyrido[3,4-d]pyrimidin-4-ylamino]-phenoxy}-piperidin-1-yl)-cyclopentyl-methanone | 509.5 | 2.5 | A |
| 173. | 6 | {4-[2-Chloro-4-(6-isopropylamino-pyrido[3,4-d]pyrimidin-4-ylamino)-phenoxy]-piperidin-1-yl}-cyclopentyl-methanone | 509.5 | 2.4 | A |
| 174. | 6 | (4-{2-Chloro-4-[6-(2-hydroxy-ethylamino)-pyrido[3,4-d]pyrimidin-4-ylamino]-phenoxy}-piperidin-1-yl)-cyclopentyl-methanone | 511.4 | 2.1 | A |
| 175. | 6 | {4-[2-Chloro-4-(6-pyrrolidin-1-yl-pyrido[3,4-d]pyrimidin-4-ylamino)-phenoxy]-piperidin-1-yl}-cyclopentyl-methanone | 521.5 | 2.5 | A |
| 176. | 6 | {4-[2-Chloro-4-(6-diethylamino-pyrido[3,4-d]pyrimidin-4-ylamino)-phenoxy]-piperidin-1-yl}-cyclopentyl-methanone | 523.6 | 2.6 | A |
| 177. | 6 | (4-{2-Chloro-4-[6-(2-methoxy-ethylamino)-pyrido[3,4-d]pyrimidin-4-ylamino]-phenoxy}-piperidin-1-yl)-cyclopentyl-methanone | 525.5 | 2.3 | A |
| 178. | 6 | {4-[2-Chloro-4-(6-piperidin-1-yl-pyrido[3,4-d]pyrimidin-4-ylamino)-phenoxy]-piperidin-1-yl}-cyclopentyl-methanone | 535.6 | 2.8 | A |
| 179. | 6 | {4-[2-Chloro-4-(6-morpholin-4-yl-pyrido[3,4-d]pyrimidin-4-ylamino)-phenoxy]-piperidin-1-yl}-cyclopentyl-methanone | 537.5 | 2.5 | A |
| 180. | 6 | 2-{4-[3-Chloro-4-(1-cyclopentanecarbonyl-piperidin-4-yloxy)-phenylamino]-pyrido[3,4-d]pyrimidin-6-ylamino}-acetamide | 524.5 | 2 | A |

TABLE I-continued

| Example No. | Preparation Method (Scheme No.) | Name | LRMS (MH+) | HPLC retention time (min) | HPLC Method |
|---|---|---|---|---|---|
| 181. | 6 | (4-{2-Chloro-4-[6-(2-methanesulfonyl-ethylamino)-pyrido[3,4-d]pyrimidin-4-ylamino]-phenoxy}-piperidin-1-yl)-cyclopentyl-methanone | 573.5 | 2.2 | A |
| 182. | 6 | Cyclopentyl-{4-[2-methoxy-4-(6-methylamino-pyrido[3,4-d]pyrimidin-4-ylamino)-phenoxy]-piperidin-1-yl}-methanone | 477.4 | 1.9 | A |
| 183. | 6 | Cyclopentyl-{4-[4-(6-dimethylamino-pyrido[3,4-d]pyrimidin-4-ylamino)-2-methoxy-phenoxy]-piperidin-1-yl}-methanone | 491.5 | 2.1 | A |
| 184. | 6 | {4-[4-(6-Azetidin-1-yl-pyrido[3,4-d]pyrimidin-4-ylamino)-2-methoxy-phenoxy]-piperidin-1-yl}-cyclopentyl-methanone | 503.5 | 2.1 | A |
| 185. | 6 | Cyclopentyl-{4-[4-(6-cyclopropylamino-pyrido[3,4-d]pyrimidin-4-ylamino)-2-methoxy-phenoxy]-piperidin-1-yl}-methanone | 503.6 | 2.1 | A |
| 186. | 6 | Cyclopentyl-(4-{4-[6-(ethyl-methyl-amino)-pyrido[3,4-d]pyrimidin-4-ylamino]-2-methoxy-phenoxy}-piperidin-1-yl)-methanone | 505.5 | 2.2 | A |
| 187. | 6 | Cyclopentyl-{4-[4-(6-isopropylamino-pyrido[3,4-d]pyrimidin-4-ylamino)-2-methoxy-phenoxy]-piperidin-1-yl}-methanone | 505.6 | 2.1 | A |
| 188. | 6 | Cyclopentyl-(4-{4-[6-(2-hydroxy-ethylamino)-pyrido[3,4-d]pyrimidin-4-ylamino]-2-methoxy-phenoxy}-piperidin-1-yl)-methanone | 507.4 | 1.8 | A |
| 190. | 6 | Cyclopentyl-{4-[2-methoxy-4-(6-pyrrolidin-1-yl-pyrido[3,4-d]pyrimidin-4-ylamino)-phenoxy]-piperidin-1-yl}-methanone | 517.5 | 2.2 | A |
| 191. | 6 | Cyclopentyl-{4-[4-(6-diethylamino-pyrido[3,4-d]pyrimidin-4-ylamino)-2-methoxy-phenoxy]-piperidin-1-yl}-methanone | 519.6 | 2.3 | A |
| 192. | 6 | Cyclopentyl-(4-{2-methoxy-4-[6-(2-methoxy-ethylamino)-pyrido[3,4-d]pyrimidin-4-ylamino]-phenoxy}-piperidin-1-yl)-methanone | 521.5 | 1.9 | A |
| 193. | 6 | Cyclopentyl-{4-[2-methoxy-4-(6-piperidin-1-yl-pyrido[3,4-d]pyrimidin-4-ylamino)-phenoxy]-piperidin-1-yl}-methanone | 531.6 | 2.4 | A |
| 194. | 6 | Cyclopentyl-{4-[2-methoxy-4-(6-morpholin-4-yl-pyrido[3,4-d]pyrimidin-4-ylamino)-phenoxy]-piperidin-1-yl}-methanone | 533.4 | 2.1 | A |
| 195. | 6 | Cyclopentyl-(4-{4-[6-(2-methanesulfonyl-ethylamino)-pyrido[3,4-d]pyrimidin-4-ylamino]-2-methoxy-phenoxy}-piperidin-1-yl)-methanone | 569.5 | 2.3 | A |

What is claimed is:

1. A compound of the formula 1

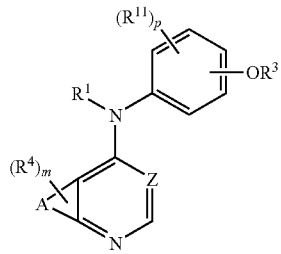

or a pharmaceutically acceptable salt, thereof, wherein: Z is N;

A represents a fused phenyl ring optionally substituted with 0 to 3 $R^4$ groups;

each $R^1$ and $R^2$ is independently selected from H and $C_1$-$C_6$ alkyl;

m is an integer from 0 to 3;

p is an integer from 0 to 4;

$R^3$ is piperidin-4-yl optionally fused to a benzene ring or a $C_5$-$C_8$ cycloalkyl group, and the foregoing $R^3$ groups, including any optional fused rings referred to above, are optionally substituted by 1 to 5 $R^9$ groups;

$R^4$ is —$(CR^1R^2)_qX(CR^1R^2)_rR^5$ wherein q is an integer from 0 to 5, and r is an integer from 0 to 5, X can be absent or represents —$N(R^{14})$—, —NH—, O, CO, —$N(R^{14})CO$—, —$CON(R^{14})$—, —C(O)(cis or trans alkene)-, $NR^1C(O)$(cis or trans alkene)-, C(O)(alkyne)-, $NR^1C(O)$(alkyne)-, —$N(R^{14})C(O)N(R^{14})$—, —$N(R^{14})S(O)_j$—, —$S(O)_jN(R^{14})$—, $S(O)_j$, wherein j is an integer from 0 to 2;

$R^5$ is $R^{12}$, C(O)$NR^6R^7$, $C_3$-$C_8$ cycloalkyl, or 4 to 10 membered heterocyclic, wherein 1 or 2 ring carbon atoms of the heterocyclic group are optionally substituted with an oxo (=O) moiety and sulfur containing heterocyclic groups are optionally substituted on S with 1 or 2 oxo (=O) moieties, the cycloalkyl, and heterocyclic moieties of the foregoing $R^5$ groups are optionally substituted with 1 to 5 substituents independently selected from halo, cyano, nitro, trifluoromethyl, trifluoromethoxy, $C_1$-$C_6$ alkyl, $C_2$-$C_6$ alkenyl, $C_2$-$C_6$ alkynyl, hydroxy, —$(CR^1R^2)_qX(CR^1R^2)_rR^{12}$ wherein q is an integer from 0 to 5, and r is an integer from 0 to 5, X can be absent or represents —$N(R^{14})$—, —NH—, O, CO, —$N(R^{14})CO$—, —$CON(R^{14})$—, —$N(R^{14})C(O)N(R^{14})$—, —$N(R^{14})S(O)_j$—, —$S(O)_jN(R^{14})$—, $S(O)j$, wherein j is an integer from 0 to 2;

each R, $R^6$, $R^{6a}$ and $R^7$ are independently selected from H, $C_1$-$C_{10}$ alkyl, —$(CR^1R^2)_t(C_6$-$C_{10}$ aryl), and —$(CR^1R^2)_t$ (4 to 10 membered heterocyclic), wherein t is an integer from 0 to 5, 1 or 2 ring carbon atoms of the heterocyclic group are optionally substituted with an oxo (=O) moiety, the alkyl, aryl and heterocyclic moieties of the foregoing $R^6$ and $R^7$ groups are optionally substituted with 1 to 5 substituents independently selected from halo, cyano, nitro, —$NR^1R^2$, trifluoromethyl, trifluoromethoxy, $C_1$-$C_6$ alkyl, $C_2$-$C_6$ alkenyl, $C_2$-$C_6$ alkynyl, hydroxy, $C_1$-$C_6$ alkoxy, —$(CR^1R^2)_qW(CR^1R^2)_r$ $R^{15}$ wherein q is an integer from 0 to 5, and r is an integer from 0 to 5, W can be absent or represents $N(R^{14})$, O, alkyne, cis or trans alkene, CO, —$N(R^{14})CO$—, —CON $(R^{14})$—, —$N(R^{14})C(O)N(R^{14})$—, —$N(R^{14})S(O)_j$—, —$S(O)_jN(R^{14})$—, $S(O)_j$, wherein j is an integer from 0 to 2;

or $R^6$ and $R^7$, or $R^{6a}$ and $R^7$, when attached to the same nitrogen atom, can be taken together to form a 4 to 10 membered hetero cyclic ring which may include 1 to 3 additional hetero moieties, in addition to the nitrogen to which said $R^6$, $R^{6a}$, and $R^7$ are attached, selected from N, $N(R^1)$, O, and S, provided two O atoms, two S atoms or an O and S atom are not attached directly to each other, and the foregoing $R^6$ and $R^7$ ring groups are optionally substituted with 1 to 5 substituents independently selected from halo, cyano, nitro, —$NR^1R^2$, trifluoromethyl, trifluoromethoxy, $C_1$-$C_6$ alkyl, $C_2$-$C_6$ alkenyl, $C_2$-$C_6$ alkynyl, hydroxy, $C_1$-$C_6$ alkoxy, —$(CR^1R^2)_qW$ $(CR^1R^2)_rR^{15}$ wherein q is an integer from 0 to 5, and r is an integer from 0 to 5, W can be absent or represents $N(R^{14})$, O, alkyne, cis or trans alkene, CO, —$N(R^{14})$ CO—, —$CON(R^{14})$—, —$N(R^{14})C(O)N(R^{14})$—, —$N(R^{14})S(O)_j$—, —$S(O)_jN(R^{14})$—, $S(O)_j$, wherein j is an integer from 0 to 2;

each $R^8$ is independently selected from halo, cyano, nitro, trifluoromethoxy, trifluoromethyl, azido, hydroxy, $C_3$-$C_8$ cyclic alkyl, $C_1$-$C_6$ alkoxy, $C_1$-$C_{10}$ alkyl, $C_2$-$C_6$ alkenyl, $C_2$-$C_6$ alkynyl, —C(O)$R^6$, —C(O)$OR^6$, —OC(O)$R^6$, —$NR^6C(O)R^7$, —$NR^6SO_2NR^7R^1$, —$NR^6C(O)NR^1R^7$, —$NR^6C(O)OR^7$, —C(O)$NR^6R^7$, —$NR^6R^7$, —$SO_2NR^6R^7$, —$S(O)_j(C_1$-$C_6$ alkyl) wherein j is an integer from 0 to 2, —$(CR^1R^2)_t(C_6$-$C_{10}$aryl), —$(CR^1R^2)_t$(4 to 10 membered heterocyclic), —$(CR^1R^2)_qC(O)$ $(CR^1R^2)_t(C_6$-$C_{10}$aryl), —$(CR^1R^2)_qC(O)(CR^1R^2)_t$(4 to 10 membered heterocyclic), —$(CR^1R^2)_tO(CR^1R^2)_q$ $(C_6$-$C_{10}$ aryl), —$(CR^1R^2)_tO(CR_1R^2)_q$(4 to 10 membered heterocyclic), —$(CR^1R^2)_qS(O)_j(CR^1R^2)_t(C_6$-$C_{10}$ aryl), and —$(CR^1R^2)_qS(O)_j(CR^1R^2)_t$(4 to 10 membered hetero cyclic), wherein j is 0, 1 or 2, q and t are each independently an integer from 0 to 5, 1 or 2 ring carbon atoms of the heterocyclic moieties of the foregoing $R^8$ groups are optionally substituted with an oxo (=O) moiety, and the alkyl, alkenyl, alkynyl, aryl and heterocyclic moieties of the foregoing $R^8$ groups are optionally substituted with 1 to 3 substituents independently selected from halo, cyano, nitro, trifluoromethyl, trifluoromethoxy, azido, —$OR^6$, —C(O)$R^6$, —C(O)$OR^6$, —OC(O)$R^6$, —$NR^6C(O)R^7$, —C(O)$NR^6R^7$, —$NR^6R^7$, —$NR^6OR^7$, $C_1$-$C_6$ alkyl, $C_2$-$C_6$ alkenyl, $C_2$-$C_6$ alkynyl, —$(CR^1R^2)_t(C_6$-$C_{10}$ aryl), and —$(CR^1R^2)_t$(4 to 10 membered heterocyclic), wherein t is an integer from 0 to 5;

each $R^9$ is independently selected from trifluoromethyl, $C_3$-$C_8$ cyclic alkyl, $C_1$-$C_{10}$ alkyl, $C_2$-$C_6$ alkenyl, $C_2$-$C_6$ alkynyl, —C(O)$R^6$, —C(O)$OR^6$, —C(O)$NR^6R^7$, —$SO_2NR^6R^7$, —$S(O)_j(C_1$-$C_6$ alkyl) wherein j is an integer from 0 to 2, —$(CR^1R^2)_t(C_6$-$C_{10}$ aryl), —$(CR^1R^2)_t$(4 to 10 membered heterocyclic), —$(CR^1R^2)_qC(O)$ $(CR^1R^2)_t(C_6$-$C_{10}$ aryl), —$(CR^1R^2)_qC(O)(CR^1R^2)_t$(4 to 10 membered heterocyclic), —$(CR^1R^2)_hO(CR^1R^2)_q$ $(C_6$-$C_{10}$ aryl), —$(CR^1R^2)_hO(CR^1R^2)_q$(4 to 10 membered heterocyclic), —$(CR^1R^2)_qS(O)_j(CR^1R^2)_t(C_6$-$C_{10}$ aryl), and —$(CR^1R^2)_qS(O)_j(CR^1R^2)_t$(4 to 10 membered heterocyclic), wherein j is 0, 1 or 2, q and t are each independently an integer from 0 to 5, h is an integer from 1 to 5, 1 or 2 ring carbon atoms of the heterocyclic moieties of the foregoing $R^9$ groups are optionally substituted with an oxo (=O) moiety, and the alkyl, alkenyl, alkynyl, aryl and heterocyclic moieties of the foregoing $R^9$ groups are optionally substituted with 1 to 3 substituents independently selected from halo, cyano, nitro, trifluoromethyl, trifluoromethoxy, azido, —OR⁶, —C(O)R⁶, —C(O)OR⁶, —OC(O)R⁶, —NR⁶C(O)R⁷, —C(O)NR⁶R⁷, —NR⁶R⁷, —NR⁶OR⁷, $C_1$-$C_6$ alkyl, $C_2$-$C_6$ alkenyl, $C_2$-$C_6$ alkynyl, —(CR¹R²)$_t$($C_6$-$C_{10}$ aryl), and —(CR¹R²)$_t$(4 to 10 membered heterocyclic), wherein t is an integer from 0 to 5;

each R¹⁰ is independently selected from halo, cyano, nitro, trifluoromethoxy, trifluoromethyl, azido, hydroxy, $C_3$-$C_8$ cyclic alkyl, $C_1$-$C_6$ alkoxy, $C_1$-$C_6$ amino, $C_1$-$C_{10}$ alkyl, $C_2$-$C_6$ alkenyl, $C_2$-$C_6$ alkynyl, —C(O)R¹, —C(O)OR¹, —OC(O)R¹, —NR¹C(O)R², —NR¹SO₂NR²R¹, —NR¹C(O)NR¹R², —NR¹C(O)OR², —C(O)NR¹R², —NR¹R², —SO₂NR¹R², —S(O)$_j$($C_1$-$C_6$ alkyl) wherein j is an integer from 0 to 2, —(CR¹R²)$_t$($C_6$-$C_{10}$ aryl), —(CR¹R²)$_t$(4 to 10 membered heterocyclic), —(CR¹R²)$_q$(C(O))(CR¹R²)$_t$($C_6C_{10}$ aryl), —(CR¹R²)$_q$C(O)(CR¹R²)$_t$(4 to 10 membered heterocyclic), —(CR¹R²)$_t$O(CR¹R²)$_q$($C_6$-$C_{10}$ aryl), —(CR¹R²)$_t$O(CR¹R²)$_q$(4 to 10 membered heterocyclic), —(CR¹R²)$_q$S(O)$_j$(CR¹R²)$_t$($C_6$-$C_{10}$ aryl), and —(CR¹R²)$_q$S(O)$_j$(CR¹R²)$_t$(4 to 10 membered heterocyclic), wherein j is 0, 1 or 2, q and t are each independently an integer from 0 to 5, 1 or 2 ring carbon atoms of the heterocyclic moieties of the foregoing R¹⁰ groups are optionally substituted with an oxo (=O) moiety, and the alkyl, alkenyl, alkynyl, aryl and heterocyclic moieties of the foregoing R¹⁰ groups are optionally substituted with 1 to 3 R¹ substituents;

each R¹¹ is independently selected from the substituents provided in the definition of R⁸ except R¹¹ is not azido;

R¹² is R⁶, —OR⁶, —OC(O)R⁶, —OC(O)NR⁶R⁷, —OCO₂R⁶, —S(O)$_j$R⁶, —S(O)$_j$NR⁶R⁷, —NR⁶R⁷, —NR⁶C(O)R⁷, —NR⁶SO₂R⁷, —NR⁶C(O)NR⁶ᵃR⁷, —NR⁶SO₂NR⁶ᵃR⁷, —NR⁶CO₂R⁷, CN, —C(O)R⁶, or halo, wherein j is an integer from 0 to 2;

R¹⁴ H, R¹⁵, —C(O)R¹⁵, —SO₂R¹⁵, —C(O)NR¹R¹⁰, —SO₂NR¹R¹⁰, —C(O)NR¹⁶R¹⁷, —SO₂NR¹⁶R¹⁷, or —CO₂R¹⁵;

R¹⁵ is R¹⁸, —(CR¹R²)$_t$($C_6$-$C_{10}$ aryl), —(CR¹R²)$_t$(4 to 10 membered heterocyclic), wherein t is an integer from 0 to 5, 1 or 2 ring carbon atoms of the heterocyclic group are optionally substituted with an oxo (=O) moiety, and the aryl and heterocyclic moieties of the foregoing R¹⁵ groups are optionally substituted with 1 to 3 R¹⁰ substituents;

R¹⁶ and R¹⁷ in addition to the nitrogen to which said R¹⁶ and R¹⁷ are attached form a 4 to 10 membered heterocyclic ring which may include 1 to 3 additional hetero moieties, selected from N, N(R¹), O, and S, provided two O atoms, two S atoms or an O and S atom are not attached directly to each other, and the 4 to 10 membered heterocyclic ring is optionally substituted with 1 to 5 substituents independently selected from halo, cyano, nitro, —NR¹R², trifluoromethyl, trifluoromethoxy, $C_1$-$C_6$ alkyl, $C_2$-$C_6$ alkenyl, $C_2$-$C_6$ alkynyl, hydroxy, and $C_1$-$C_6$ alkoxy;

R¹⁸ is $C_1$-$C_6$ alkyl wherein each carbon not bound to a N or O atom, or to S(O)$_j$, wherein j is an integer from 0 to 2, is optionally substituted with R¹⁰;

and wherein any of the above-mentioned substituents comprising a CH₃ (methyl), CH₂ (methylene), or CH (methine) group, which is not attached to a halogen, SO or SO₂ group or to a N, O or S atom, is optionally substituted with a group selected from hydroxy, halo, $C_1$-$C_4$ alkyl, $C_1$-$C_4$ alkoxy and —NR¹R².

2. The compound of claim 1, wherein R³ is

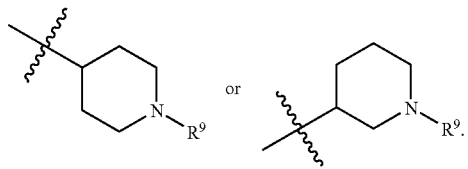

3. The compound of claim 2 wherein R⁹ independently selected from —C(O)R⁶, or —C(O)NR⁶R⁷, p is 1, and R¹¹ is selected from the group consisting of OMe, F, Cl, Br, and Me.

4. The compound of claim 3 wherein R⁶ and R⁷ are independently selected from $C_5$-$C_{10}$ alkyl, —(CR¹R²)$_t$($C_6$-$C_{10}$ aryl), and —(CR¹R²)$_h$(4 to 10 membered heterocyclic), wherein t is an integer from 0 to 2, and h is an integer from 1 to 3; or R⁶ and R⁷ in addition to the nitrogen to which the R⁶ and R⁷ are attached form a 5 to 10 membered heterocyclic ring.

5. The compound of claim 1, wherein R⁴ is —X(CR¹R²)$_r$R⁵ wherein r is an integer from 0 to 5, X can be absent or represents —N(R¹⁴)—, —NH—, O, CO, —N(R¹⁴)CO—, —CON(R¹⁴)—, —N(R¹⁴)C(O)N(R¹⁴)—, —N(R¹⁴)S(O)$_j$—, wherein j is an integer from 0 to 2, and R⁵ represents NR⁶R⁷, —OR⁶, —OC(O)R⁶, —OC(O)NR⁶R⁷, —OCO₂R⁶, —S(O)$_j$R⁶, —S(O)$_j$NR⁶R⁷, —NR⁶R⁷, —NR⁶C(O)R⁷, —NR⁶SO₂R⁷, —NR⁶C(O)NR⁶ᵃR⁷, —NR⁶SO₂NR⁶ᵃR⁷, —NR⁶CO₂R⁷, CN, —C(O)R⁶, wherein j is an integer from 0 to 2, $C_1$-$C_{10}$ alkyl, or $C_3$-$C_8$ cycloalkyl, and further wherein R⁵ represents NR¹(R¹⁴), C(O)N(R¹)(R¹⁴), —N(R¹⁴)C(O)N(R¹)(R¹⁴), —N(R¹)(R¹⁴)S(O)$_j$R¹, wherein j is an integer from 0 to 2.

6. The compound of claim 1 wherein m is an integer between 1 and 2.

7. The compound of claim 6 wherein R⁴ is optionally located at the 6 or 7 position.

8. The compound of claim 7 wherein R⁴ is —X(CR¹R²)$_r$R⁵ wherein r is an integer from 0 to 5, X can be absent or represents —N(R¹⁴)—, —NH—, O, CO, —N(R¹⁴)CO—, —CON(R¹⁴)—, —N(R¹⁴)C(O)N(R¹⁴)—, —N(R¹⁴)S(O)$_j$—, wherein j is an integer from 0 to 2, and R⁵ represents —NR⁶R⁷, —OR⁶, —OC(O)R⁶, —OC(O)NR⁶R⁷, —OCO₂R⁶, —S(O)$_j$R⁶, —S(O)$_j$NR⁶R⁷, —NR⁶R⁷, —NR⁶C(O)R⁷, —NR⁶SO₂R⁷, —NR⁶C(O)NR⁶ᵃ, R⁷, —NR⁶SO₂NR⁶ᵃR⁷, —NR⁶CO₂R⁷, CN, —C(O)R⁶, wherein j is an integer from 0 to 2, $C_1$-$C_{10}$ alkyl, or $C_3$-$C_8$ cycloalkyl, and further wherein R⁵ represents NR¹(R¹⁴), C(O)N(R¹)(R¹⁴), —N(R¹⁴)C(O)N(R¹)(R¹⁴), —N(R¹)(R¹⁴)S(O)$_j$R¹, wherein j is an integer from 0 to 2.

9. The compound of claim 8 wherein p is 1, and R¹¹ is selected from the group consisting of OMe, F, Cl, Br, and Me.

10. The compound of claim 9 wherein R⁹ is independently selected from the group consisting of —C(O)R⁶, —C(O)OR⁶, —C(O)NR⁶R⁷, and —SO₂NR⁶R⁷.

11. The compound of claim 10 wherein R⁶ and R⁷ is independently selected from $C_5$-$C_{10}$ alkyl, —(CR¹R²)$_t$($C_6$-$C_{10}$ aryl), and —(CR¹R²)$_h$(4 to 10 membered heterocyclic) and h is an integer from 1 to 5; or R⁶ and R⁷ in addition to the nitrogen to which the R⁶ and R⁷ are attached form a 5 to 10 membered heterocyclic ring.

12. A compound according to claim 1 selected from the group consisting of:

Cyclobutyl-{4-[4-(6-methoxy-quinazolin-4-ylamino)-2-methyl-phenoxy]-piperidin-1-yl}-methanone;

4-[4-(6-Methoxy-quinazolin-4-ylamino)-2-methyl-phenoxy]-piperidine-1-carboxylic acid (2,6-difluoro-phenyl)-amide;

1-{4-[4-(6-Methoxy-quinazolin-4-ylamino)-2-methyl-phenoxy]-piperidin-1-yl}-3,3-dimethyl- butan-1-one;

2-Cyclopropyl-1-{4-[4-(6-methoxy-quinazolin-4-ylamino)-2-methyl-phenoxy]-piperidin-1-yl}-ethanone;

4-[4-(6-Methoxy-quinazolin-4-ylamino)-2-methyl-phenoxy]-piperidine-1-carboxylic acid tert-butyl-amide;

4-[4-(6-Methoxy-quinazolin-4-ylamino)-2-methyl-phenoxy]-piperidine-1-carboxylic acid cyclopentylamide;

4-[4-(6-Methoxy-quinazolin-4-ylamino)-2-methyl-phenoxy]-piperidine-1-carboxylic acid (4-methoxy-phenyl)-amide;

4-[4-(6,7-Dimethoxy-quinazolin-4-ylamino)-2-methyl-phenoxy]-piperidine-1-carboxylic acid (2,6-difluoro-phenyl)-amide;

4-[4-(6,7-Dimethoxy-quinazolin-4-ylamino)-2-methyl-phenoxy]-piperidine-1-carboxylic acid (4-methoxy-phenyl)-amide;

{4-[4-(6,7-Dimethoxy-quinazolin-4-ylamino)-2-methyl-phenoxy]-piperidin-1-yl}-morpholin-4-yl-methanone;

4-[4-(6,7-Dimethoxy-quinazolin-4-ylamino)-2-methyl-phenoxy]-piperidine-1-carboxylic acid (2,5-difluoro-phenyl)-amide;

4-[4-(6,7-Dimethoxy-quinazolin-4-ylamino)-2-methyl-phenoxy]-piperidine-1-carboxylic acid cyclopentylamide;

1-{4-[4-(6,7-Dimethoxy-quinazolin-4-ylamino)-2-methyl-phenoxy]-piperidin-1-yl}-3,3-dimethyl-butan-1-one;

{4-[4-(6,7-Dimethoxy-quinazolin-4-ylamino)-2-phenoxy]-piperidin-1-yl}-(3-methoxy-phenyl)-methanone;

Cyclopentyl-{4-[4-(6,7-dimethoxy-quinazolin-4-ylamino)-2-methyl-phenoxy]-piperidin-1-yl}-methanone;

2-Cyclopentyl-1-{4-[4-(6,7-dimethoxy-quinazolin-4-ylamino)-2-methyl-phenoxy]-piperidin-1-yl}-ethanone;

{4-[4-(6,7-Dimethoxy-quinazolin-4-ylamino)-2-methyl-phenoxy]-piperidin-1-yl}-(tetrahydro-furan-2-yl)-methanone;

4-[4-(6,7-Dimethoxy-quinazolin-4-ylamino)-2-methyl-phenoxy]-piperidine-1-carboxylic acid o-tolyl-amide;

4-[4-(6,7-Dimethoxy-quinazolin-4-ylamino)-2-methyl-phenoxy]-piperidine-1-carboxylic acid (4-chloro-phenyl)-amide;

4-[4-(6,7-Dimethoxy-quinazolin-4-ylamino)-2-methyl-phenoxy]-piperidine-1-carboxylic acid (2-chloro-phenyl)-amide;

4-[4-(6,7-Dimethoxy-quinazolin-4-ylamino)-2-methyl-phenoxy]-piperidine-1-carboxylic acid (2-methoxy-phenyl)-amide;

4-[4-(6,7-Dimethoxy-quinazolin-4-ylamino)-2-methyl-phenoxy]-piperidine-1-carboxylic acid (2-fluoro-phenyl)-amide;

4-[4-(6,7-Dimethoxy-quinazolin-4-ylamino)-2-methyl-phenoxy]-piperidine-1-carboxylic acid (4-fluoro-phenyl)-amide;

4-[4-(6,7-Dimethoxy-quinazolin-4-ylamino)-2-methyl-phenoxy]-piperidine-1-carboxylic acid (3-trifluoromethyl-phenyl)-amide;

4-[4-(6,7-Dimethoxy-quinazolin-4-ylamino)-2-methyl-phenoxy]-piperidine-1-carboxylic acid (2,5-difluoro-phenyl)-amide;

4-[4-(6,7-Dimethoxy-quinazolin-4-ylamino)-2-methyl-phenoxy]-piperidine-1-carboxylic acid (3-fluoro-phenyl)-amide;

4-[4-(6,7-Dimethoxy-quinazolin-4-ylamino)-2-methyl-phenoxy]-piperidine-1-carboxylic acid (2-trifluoromethyl-phenyl)-amide;

4-[4-(6,7-Dimethoxy-quinazolin-4-ylamino)-2-methyl-phenoxy]-piperidine-1-carboxylic acid (2,6-dichloro-phenyl)-amide;

4-[4-(6,7-Dimethoxy-quinazolin-4-ylamino)-2-methyl-phenoxy]-piperidine-1-carboxylic acid (4-trifluoromethyl-phenyl)-amide;

4-[4-(6,7-Dimethoxy-quinazolin-4-ylamino)-2-methyl-phenoxy]-piperidine-1-carboxylic acid (2,6-dimethyl-phenyl)-amide;

4-[4-(6,7-Dimethoxy-quinazolin-4-ylamino)-2-methyl-phenoxy]-piperidine-1-carboxylic acid (4-dimethylamino-phenyl)-amide;

4-[4-(6,7-Dimethoxy-quinazolin-4-ylamino)-2-methyl-phenoxy]-piperidine-1-carboxylic acid (3,5-difluoro-phenyl)-amide;

and the pharmaceutically acceptable salts of the foregoing compounds.

13. A compound according to claim 1 selected from the group consisting of:

Cyclobutyl-{4-[4-(6-dimethylamino-quinazolin-4-ylamino)-2-methyl-phenoxy]-piperidin-1-yl}-methanone;

Cyclobutyl-{4-[4-(6-{5-[(2-methanesulfonyl-ethylamino)-methyl]-furan-2-yl}-quinazolin-4-ylamino)-2-methyl-phenoxy]-piperidin-1yl}-methanone;

N-{4-[4-(1-Cyclobutanecarbonyl-piperidin-4-yloxy)-3-methyl-phenylamino]-quinazolin -6-yl}-acrylamide;

Cyclobutyl-{4-[2-methyl-4-(6-morpholin-4-yl-quinazolin-4-ylamino)-phenoxy]-piperidin-1-yl}-methanone;

4-[4-(6-Dimethylamino-quinazolin-4-ylamino)-2-methyl-phenoxyl]-piperidine-1-carboxylic acid (2,6-difluoro-phenyl)-amide;

4-[4-(6-{5-[(2-Methanesulfonyl-ethylamino)-methyl]-furan-2-yl}-quinazolin-4-ylamino)-2-methyl-phenoxy]-piperidine-1-carboxylic acid (2,6-difluoro-phenoxy)-amide;

4-[4-(6-Acryloylamino-quinazolin-4-ylamino)-2-methyl-phenoxy]-piperidine-1-carboxylic acid (2,6-difluoro-phenyl)-amide;

4-[2-Methyl-4-(6-morpholin-4-yl-quinazolin4-ylamino)-phenoxy-phenoxy]-piperidine-1carboxylic acid (2,6-difluoro-phenyl)-amide;

4-[2-Chloro-4-(6-dimethylamino-quinazolin-4ylamino)-phenoxy]-piperidine-1-carboxylic acid (2,6-difluoro-phenyl)-amide;

4-[2-Chloro-4-(6-{5-[(2-methanesulfonyl-ethylamino)-methyl]-furan-2-yl}-quinazolin-4-ylamino)-phenoxy]-piperidine-1-carboxylic acid (2,6-difluoro-phenyl)-amide;

4-[4-(6-Acryloylamino-quinazolin-4-ylamino)-2-chloro-phenoxy]-piperidine-1-carboxylic acid (2,6-difluoro-phenyl)-amide;

4-[2-Chloro-4-(6-morpholin-4-yl-quinazolin-4-ylamino)-phenoxy]-piperidine-1-carboxylic acid (2,6-difluoro-phenyl)-amide;

4-[2-Chloro-4-(6,7-dimethoxy-quinazolin-4-ylamino)-phenoxy]-piperidine-1-carboxylic acid (2,6-difluoro-phenyl)-amide;

(4-{4-[6,7-Bis-(2-methoxy-ethoxy)-quinazolin-4-ylamino]-2-methyl-phenoxy}-piperidin-1-yl)-cyclobutyl-methanone;

4-{4-[6,7-Bis-(2-methoxy-ethoxy)-quinazolin-4-ylamino]-2-methyl-phenoxy}-piperidine-1-carboxylic acid (2,6-difluoro-phenyl)-amide;

4-{4-[6,7-Bis-(2-methoxy-ethoxy)-quinazolin-4-ylamino]-2-chloro-phenoxy}-piperidine-1-carboxylic acid (2,6-difluoro-phenyl)-amide;

Cyclobutyl-(4-{4-[7-methoxy-6-(3-morpholin-4-yl-propoxy)-quinazolin-4-ylamino]-2-methyl-phenoxy}-piperidin-1-yl)-methanone;

4-{4-[7-Methoxy-6-(3-morpholin-4-yl-propoxy)-quinazolin-4-ylamino]-2-methyl-phenoxy)}-piperidine-1-carboxylic acid (2,6-difluoro-phenyl)-amide;

4-{2-Chloro-4-[7-methoxy-6-(3-morpholin-4-yl-propoxy)-quinazolin-4-ylamino]-phenoxy}-piperidine-1-carboxylic acid (2,6-difluoro-phenyl)-amide;

and the pharmaceutically acceptable salts of the foregoing compounds.

14. A compound according to claim 1 selected from the group consisting of

4-[4-(6,7-Dimethoxy-quinazolin-4-ylamino)-2-methyl-phenoxy]-piperidine-1-carboxylic acid (2,6-difluoro-phenyl)-amide;

4-[4-(6-Methoxy-quinazolin-4-ylamino)-2-methyl-phenoxy]-piperidine-1-carboxylic acid cyclopentylamide;

and the pharmaceutically acceptable salts of the foregoing compounds.

15. A pharmaceutical composition for the treatment of abnormal cell growth in a mammal comprising an amount of a compound of claim 1 that is effective in treating abnormal cell growth, and a pharmaceutically acceptable carrier.

* * * * *